(12) United States Patent
Kawanishi et al.

(10) Patent No.: US 7,195,865 B2
(45) Date of Patent: Mar. 27, 2007

(54) METHOD AND APPARATUS FOR PREPARING GRAINS OF SILVER SALT OF ORGANIC AND METHOD FOR PRODUCING THERMALLY PROCESSED IMAGE RECORDING MATERIAL

(75) Inventors: Naoyuki Kawanishi, Kanagawa (JP); Takashi Ando, Kanagawa (JP); Yoichi Nagai, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/815,957

(22) Filed: Apr. 2, 2004

(65) Prior Publication Data

US 2004/0185395 A1    Sep. 23, 2004

Related U.S. Application Data

(62) Division of application No. 09/893,750, filed on Jun. 29, 2001, now Pat. No. 6,737,231.

(30) Foreign Application Priority Data

| Jun. 29, 2000 | (JP) | ............................. 2000-195621 |
| Jul. 14, 2000 | (JP) | ............................. 2000-213813 |
| Aug. 3, 2000 | (JP) | ............................. 2000-236044 |
| Aug. 7, 2000 | (JP) | ............................. 2000-237897 |

(51) Int. Cl.
*G03C 1/00*    (2006.01)

(52) U.S. Cl. ...................... 430/620; 430/617; 430/631; 430/935

(58) Field of Classification Search ................ 430/620, 430/617, 569, 631, 935; 516/98, 99; 210/650
See application file for complete search history.

(56) References Cited

U.S. PATENT DOCUMENTS 6,472,546 B1    10/2002    Kawanishi et al.
6,783,925 B1 *    8/2004    Yasuda ........................ 430/619

FOREIGN PATENT DOCUMENTS

| EP | 0 962 812 A1 | 12/1999 |
| EP | 1 063 556 A2 | 12/2000 |
| EP | 1 063 566 A1 | 12/2000 |
| EP | 1 069 468 A1 | 1/2001 |

* cited by examiner

*Primary Examiner*—Thorl Chea
(74) *Attorney, Agent, or Firm*—Sughrue Mion, PLLC

(57) ABSTRACT

Disclosed are a method for preparing grains of silver salt of an organic acid by reacting a solution containing silver ions and a solution containing an alkali metal salt of an organic acid, in which the reaction is performed in sealed mixing means and which comprises steps of supplying the solution containing silver ions into a reaction field solution before introduced into the sealed mixing means, and supplying the solution containing an alkali metal salt of an organic acid into the reaction field solution or sealed mixing means to which the solution containing silver ions has been supplied, etc. According to the present invention, high quality grains of silver salt of an organic acid can be efficiently produced at low cost.

20 Claims, 12 Drawing Sheets

METHOD AND APPARATUS FOR PREPARING GRAINS OF SILVER SALT OF ORGANIC AND METHOD FOR PRODUCING THERMALLY PROCESSED IMAGE RECORDING MATERIAL

CROSS-REFERENCE TO RELATED APPLICATIONS

This application is a divisional of U.S. application Ser. No. 09/893,750 filed Jun. 29, 2001 now U.S. Pat. No. 6,737,231, the disclosure of which is incorporated herein by reference.

FIELD OF THE INVENTION

The present invention relates to methods for efficiently preparing grains of silver salt of an organic acid by reacting a solution containing silver ions and a solution containing an alkali metal salt of an organic acid. The present invention also relates to apparatuses for preparing grains of silver salt of an organic acid that require low facility cost and show high productivity. The present invention further relates to a method for producing a thermally processed image recording material that utilizes the methods for preparing grains of silver salt of an organic acid.

BACKGROUND OF THE INVENTION

In recent years, reduction of amount of waste processing solutions is strongly desired in the field of medical diagnosis from the standpoints of environmental protection and space savings. Therefore, techniques relating to photothermographic materials for use in photographic-art processes and medical diagnosis are required which enables efficient exposure by a laser image setter or laser imager and formation of a clear black image having high resolution and sharpness. Such photothermographic materials can provide users with a simple and non-polluting heat development processing system that eliminates the use of solution-type processing chemicals.

The same is demanded in the field of ordinary image-forming materials. However, photo-images for medical use, in particular, require high image quality excellent in sharpness and graininess as they need very fine images. In addition, for easy diagnosis, cold monochromatic images are preferred. At present, various types of hard copy systems using pigment and dye, for example, ink jet printers and electrophotographic systems are available as ordinary imaging systems. However, no satisfactory image-forming system is available for medical use.

Meanwhile, methods for forming an image by heat development are described in, for example, U.S. Pat. Nos. 3,152,904 and 3,457,075 and D. Klosterboer, "Thermally Processed Silver Systems", Imaging Processes and Materials, Neblette, 8th ed., compiled by J. Sturge, V. Walworthand A. Shepp, Chapter 9, p. 279, (1989). Among these, the photothermographic material generally contains a photocatalyst (e.g., silver halide) in a catalytically active amount, a reducing agent, a reducible silver salt (e.g., organic acid silver salt), and optionally a toning agent for controlling silver color tone, which are usually dispersed in an organic binder matrix. In this photothermographic material when the material is heated at a high temperature (e.g., 80° C. or higher) after light exposure, black silver images are produced through an oxidation-reduction reaction between the silver halide or reducible silver salt (which functions as an oxidizing agent) and the reducing agent. The oxidation-reduction reaction is accelerated by catalytic action of a latent image of the silver halide generated upon exposure. Therefore, the monochromatic silver images are formed in exposed areas of the materials (U.S. Pat. No. 2,910,377, Japanese Patent Publication (Kokoku, hereinafter referred to as JP-B) 43-4924 etc.). These thermal image-forming systems utilizing silver salts of organic acids can achieve image quality and color tone required for images for medical use.

The silver source used in these systems is generally a silver salt of an organic acid, and various methods for producing it have been known. For example, there can be mentioned the method of preparing a silver salt of an organic acid under coexistence of water and a hardly water-soluble solvent as disclosed in Japanese Patent Laid-open Publication (Kokai, hereinafter referred to as JP-A) 49-93310, JP-A-49-94619 and JP-A-53-68702, the method of preparing a silver salt of an organic acid in an aqueous solution as disclosed in JP-A-53-31611, JP-A-54-4117 and JP-A-54-46709, the method of preparing a silver salt of an organic acid in an organic solvent as disclosed in JP-A-57-186745, JP-A-47-9432 and U.S. Pat. No. 3,700,458 and so forth. Basically, the preparation is carried out by heating an organic acid to a temperature higher than its melting point to melt it in water, adding sodium hydroxide or an alkali metal salt with vigorous stirring, and then adding a solution containing silver ions in order to convert the alkali soap into silver soap.

Such alkali soap forms micelles in an aqueous solution, and gives a solution of whitely turbid appearance. The reaction from such a micelle state to the silver soap often suffers from problems concerning production stability. Therefore, as a method for obtaining the alkali soap as a uniform solution, a method of using a mixed solution of water and alcohol as the solvent is disclosed in JP-A-55-40607.

Further, since alkali soap presents alkalinity, the silver soap will be prepared under a high pH condition in the above case. However, addition of a solution containing silver ions into an alkaline solution produces silver oxide as a by-product. Further, it also generates unintended silver nuclei produced by a trace amount of reducing contaminants, which are unavoidable in view of production process and exhibit high reducing property due to the high pH. Such by-products are extremely disadvantageous from the viewpoint that they degrade performance of photothermographic materials, in particular, they cause undesired fog. In this respect, the aforementioned problems are not solved even in the method disclosed in JP-A-55-40607, which aims at obtaining a uniform solution in order to suppress the generation of the by-products.

Further, JP-A-9-127643 discloses a method for producing a silver salt by simultaneous addition of measured amounts of an alkali metal salt solution and a silver nitrate solution, and refers to simultaneous addition of a solution of sodium behenate in a mixture of water and isopropyl alcohol and a solution of silver nitrate. This method can at least shift the pH of the reaction from the high pH region to a neutral region, and thus it is a preferred method for reducing the generation amount of silver oxide. However, isopropyl alcohol shows weak reducing property, and this makes the method insufficient as a method for completely solving the problem of fog.

Further, JP-A-9-127643 discloses a method for producing a silver salt by simultaneous addition of measured amounts of an alkali metal salt solution and a silver nitrate solution, and refers to simultaneous addition of a solution of sodium behenate in a mixture of water and isopropyl alcohol and a solution of silver nitrate. This method can at least shift the pH of the reaction from the high pH region to a neutral region, and thus it is a preferred method for reducing the generation amount of silver oxide. However, isopropyl alcohol shows weak reducing property, and this makes the method insufficient as a method for completely solving the problem of fog.

Moreover, the silver behenate grains formed by this method are two-dimensionally and anisotropically grown acicular grains having a size of 0.04 μm to 0.05 μm, and no description is found concerning control of the grain size or grain morphology.

JP-A-11-349325 disclose a method for forming scaly grains, which show morphology different from that of the conventional acicular grains, by using a low temperature in a reaction field for the simultaneous addition of measured amounts of alkali metal salt solution and solution containing silver ions. In this method, scaly grains can be obtained in a low temperature region, and acicular grains can be obtained in a high temperature region by controlling the temperature of the reaction field. However, this method still cannot provide such high degree of freedom that the grain morphology and grain size can be independently controlled.

In order to obtain a uniform dispersion practically usable as a coating solution containing a silver salt of an organic acid, it is necessary to obtain a state that the silver salt of an organic acid is finely dispersed in a solvent without aggregation. For this reason, it is necessary to develop a method for dispersing the silver salt of an organic acid as fine grains. Usually used is a method comprising separating the formed hydrophobic grains of silver salt of an organic acid as solid by filtration, mixing a dispersing agent with the solid, and dispersing the mixture again, as described in Imaging Processes and Materials, supra.

As the method for dispersing a silver salt of an organic acid as fine grains, the method of mechanically dispersing it in the presence of a dispersing aid by means of known pulverization mean (e.g., high-speedmixer, homogenizer, high-speed impact mill, Banbary mixer, homomixer, kneader, ball mill, vibrating ball mill, planetary ball mill, attriter, sand mill, bead mill, colloid mill, jet mill, roller mill, trone mill and high-speed stone mill). However, this method not only produces only a coating solution containing a lot of aggregated particles, i.e., a coating solution that gives bad coated surface quality, but also suffers from a problem that, because the method highly possibly grinds primary grains of a silver salt of an organic salt originally crystallized as a hardly wafer-soluble salt without any selectivity, silver nuclei are formed at crystal cleavage surfaces and causes increase of fog.

Then, several methods have been proposed, wherein the primary grains obtained during the reaction of a solution of alkali metal salt and a solution containing silver ions are utilized as they are, not separating the silver salt of an organic acid as solid and finely dispersing it.

For example, JP-A-8-234358 discloses a method of adding silver nitrate to an aqueous dispersion in which fine grains of an alkali salt of an organic acid are dispersed, and desalting the obtained dispersion of a silver salt of an organic acid by ultrafiltration. The above reference further refers to enhancement of the dispersion stability by carrying out the ultrafiltration for a dispersion preliminarily containing water-soluble protective colloids such as polyvinyl alcohol and gelatin.

However, the shape of the silver salt of an organic acid obtained by this method is limited to an acicular shape, and in addition, it is difficult to control the grain size in this method. Therefore, it is still insufficient for stably obtaining performance of low fog, high blackening concentration and low haze, which are desired for photothermographic materials.

Further, JP-A-9-127643 discloses a method of directly desalting a dispersion of a silver salt of an organic acid obtained by simultaneous addition of measured amounts of a solution of an alkali metal salt and a silver nitrate solution by means of dialysis or ultrafiltration. By this method, at least the primary grains obtained during the crystallization of the silver salt of an organic acid can be introduced into a photosensitive layer as they are without degrading the grains. However, problems concerning aggregation of grains under a high salt concentration circumstance, increase of viscosity upon concentration of the dispersion and so forth are not solved, and thus this method is still insufficient as practical means for obtaining a uniform dispersion.

Furthermore, JP-A-9-127643 discloses a method using a dispersing agent together, like JP-A-8-234358, but it does not refer to the kind of preferred dispersing agents. This method is not a method providing superior dispersion stability, in which the grain morphology and the grain size are controlled at a high salt concentration during the generation of grains of silver salt of an organic acid in the presence of an organic solvent such as isopropyl alcohol.

In order to obtain monodispersed grains of a silver salt of an organic acid as fine grains, vigorous stirring is required during the addition of an alkali metal salt solution and a solution containing silver ions. In particular, the solution of an organic acid alkali metal salt dissolved at a high temperature suffers from temperature decrease and shows precipitation upon addition thereof, and therefore large grains may grow if dilution rate or fluidization is slow or weak. However, when they are added to a tank in which a gas/liquid interface is present, and the stirring speed is increased, entrainment of air is caused. The grains of silver salt of organic acid are highly hydrophobic, and therefore not only the grains are adsorbed on the surfaces of the entrained bubbles to stabilize the bubbles and prevent breakage of them, but also the adjacent grains on the bubbles cause aggregation. The liquid containing air entrained in such a manner becomes a highly viscous whipped cream-like liquid, and disturbs uniform reaction.

Further, when such a liquid containing bubbles and aggregated grains is subjected to ultrafiltration operation, it suffers from problems of reduction of filtration speed due to adhesion to a membrane surface, increase of filtration pressure due to increased viscosity and so forth. Furthermore, when a hollow-fiber type membrane filter is used, it suffers from problems of blocking of pipelines due to progress of aggregation of grains and so forth. These problems constitute obstacles to the application of the methods to practical production facilities.

As described above, any method that enables independent control of the grain size and the grain morphology and stably produces monodispersed silver salt of an organic acid providing low fog has not been found yet. That is, any method has not been found yet, in which organic acid silver salt grains are formed by adding and vigorously stirring a solution containing organic acid alkali metal salt and a solution containing silver ions without causing entrainment of air or aggregation of grains, and the obtained primary grains are utilized as they are without preliminarily separating the produced organic acid silver salt as solid content.

In view of these problems of the prior art, an object of the present invention is to provide an efficient method for producing grains of silver salt of an organic acid, which enables purification of the organic acid silver salt grains produced by mixing an alkali metal salt solution and a solution containing silver ions without separating the organic acid silver salt grains as a solid content. Another object of the present invention is to provide a method and apparatus for preparing grains of silver salt of an organic acid that require low facility cost and small facility space and show high productivity.

SUMMARY OF THE INVENTION

These objects were achieved by the present invention providing the followings.

The present invention provides a method for preparing grains of silver salt of an organic acid by reacting a solution containing silver ions and a solution containing an alkali metal salt of an organic acid, which comprises steps of mixing the solution containing silver ions and the solution containing an alkali metal salt of an organic acid to conduct a reaction in sealed mixing means and removing by-product salts contained in the reaction mixture by filtration through an ultrafiltration membrane during or after the reaction (first preparation method). Preferred embodiments of this preparation method include embodiments in which at least a part of a mixture obtained after the reaction of the solution containing silver ions and the solution containing an alkali metal salt of an organic acid mixed in the sealed mixing means is circulated and added to the sealed mixing means; at least one kind of dispersing agent is added before starting the reaction or before finishing the purification utilizing an ultrafiltration membrane; at least a nonionic macromolecular dispersing agent having a molecular weight 5–50 times larger than a fractional molecular weight of the ultrafiltration membrane is used as the dispersing agent; the nonionic macromolecular dispersing agent is used at a concentration of 0.1–30 weight % of the solid content of the silver salt of an organic acid; at least one of polyvinyl alcohol, polyvinylpyrrolidone, hydroxyethyl cellulose and hydroxypropyl cellulose is used as the dispersing agent; and the by-product salts are removed by ultrafiltration in which 2- to 20-fold constant volume dilution is attained, and then the dispersion is concentrated to a concentration of 10–50 weight %.

The present invention also provides a method for preparing grains of silver salt of an organic acid by reacting a solution containing silver ions and a solution containing an alkali metal salt of an organic acid, in which the reaction is performed in sealed mixing means and which comprises steps of supplying the solution containing silver ions into a reaction field solution before introduced into the sealed mixing means, and supplying the solution containing an alkali metal salt of an organic acid into the reaction field solution or sealed mixing means to which the solution containing silver ions has been supplied (second preparation method). The Reynolds number of the solution containing silver ions is preferably in the range of 500–20000 when the solution containing silver ions is supplied to the reaction field solution.

The present invention further provides a method for preparing an aqueous dispersion of grains of silver salt of an organic acid, wherein grains of silver salt of an organic acid are prepared by reacting a solution containing silver ions and a solution containing an alkali metal salt of an organic acid, then dispersion operation is performed by a high pressure homogenizer or high speed rotary homomixer in the presence of a dispersing agent, and by-product salts are removed by ultrafiltration after or during the dispersion operation (third preparation method). Preferred embodiments of this preparation method include embodiments in which the dispersing agent is used at a concentration of 1–30 weight % of dispersoid; concentration of the silver salt of an organic acid is 1–10 weight % immediately after the reaction; after the by-product salts are removed by the ultrafiltration, concentration operation is performed by the ultrafiltration; and after electric conductivity reached a value not less than 20 µS/cm but less than 300 µS/cm as a result of the removal of the by-product salts by the ultrafiltration, the dispersion is concentrated to a concentration of 10–70 weight % by the ultrafiltration.

The present invention also provides an apparatus for preparing grains of silver salt of an organic acid, which comprises first supplying means for supplying a solution containing silver ions to sealed mixing means; second supplying means for supplying a solution containing an alkali metal salt of an organic acid to the sealed mixing means; third supplying means for supplying a reaction field solution to the sealed mixing means; the sealed mixing means for mixing materials supplied from the first, second and third supplying means to form a dispersion containing grains of silver salt of an organic acid; storage means for the formed dispersion containing grains of silver salt of an organic acid from the sealed mixing means; fourth supplying means for supplying the dispersion containing grains of silver salt of an organic acid in the storage means from the storage means to an ultrafiltration process; and purification means for removing by-product salts form the dispersion containing grains of silver salt of an organic acid by ultrafiltration (first preparation apparatus).

The present invention also provides an apparatus for preparing grains of silver salt of an organic acid, which comprises first supplying means for supplying a solution containing silver ions to sealed mixing means; second supplying means for supplying a solution containing an alkali metal salt of an organic acid to the sealed mixing means; the sealed mixing means for mixing materials supplied from the first and second supplying means and third supplying means mentioned below to form a dispersion containing grains of silver salt of an organic acid; storage means for the formed dispersion containing grains of silver salt of an organic acid from the sealed mixing means; third supplying means for supplying at least a part of the formed dispersion containing grains of silver salt of an organic acid to the sealed mixing means again; fourth supplying means for supplying the dispersion containing grains of silver salt of an organic acid in the storage means from the storage means to an ultrafiltration process; and purification means for removing by-product salts form the dispersion containing grains of silver salt of an organic acid by ultrafiltration (second preparation apparatus).

The present invention also provides an apparatus for preparing grains of silver salt of an organic acid, which comprises a pipeline for supplying a solution containing silver ions, a pipeline for supplying a solution containing an alkali metal salt of an organic acid, sealed mixing means and a pipeline for supplying a reaction field solution to the sealed mixing means, wherein the pipeline for supplying a solution containing silver ions is connected to the pipeline for supplying a reaction field solution, and the pipeline for supplying a solution containing an alkali metal salt of an organic acid is connected to the sealed mixing means or the pipeline for supplying a reaction field solution at a position between a position at which the pipeline for supplying a solution containing silver ions is connected and the sealed mixing means (third preparation apparatus).

The present invention also provides an apparatus for preparing grains of silver salt of an organic acid, which comprises a pipeline for supplying a solution containing silver ions, a pipeline for supplying a solution containing an alkali metal salt of an organic acid, first sealed mixing means, second sealed mixing means, a pipeline for connecting the first sealed mixing means and the second sealed mixing means and a pipeline for supplying a reaction field solution to the first sealed mixing means, wherein the pipeline for supplying a solution containing silver ions is connected to the pipeline for supplying a reaction field solution to the first sealed mixing means or the first sealed mixing means, and the pipeline for supplying a solution containing an alkali metal salt of an organic acid is connected to the pipeline for connecting the first sealed mixing means and second sealed mixing means or the second sealed mixing means (fourth preparation apparatus).

The present invention further provides a method for producing a thermally processed image recording material comprising a silver salt of an organic acid, a reducing agent for silver ions and a binder on at least one surface of a support, which comprises a step of applying a coating solution for image-forming layer containing an aqueous dispersion of grains of silver salt of an organic acid prepared by any one of the aforementioned preparation methods. The coating solution for image-forming layer preferably contains a photosensitive silver halide and a polymer showing an equilibrated moisture content of 2 weight % or less at 25° C. and relative humidity of 60% in the form of latex as the binder, and 30 weight % or more of the solvent of the coating solution preferably consists of water.

PREFERRED EMBODIMENT OF THE INVENTION

Figure 1:
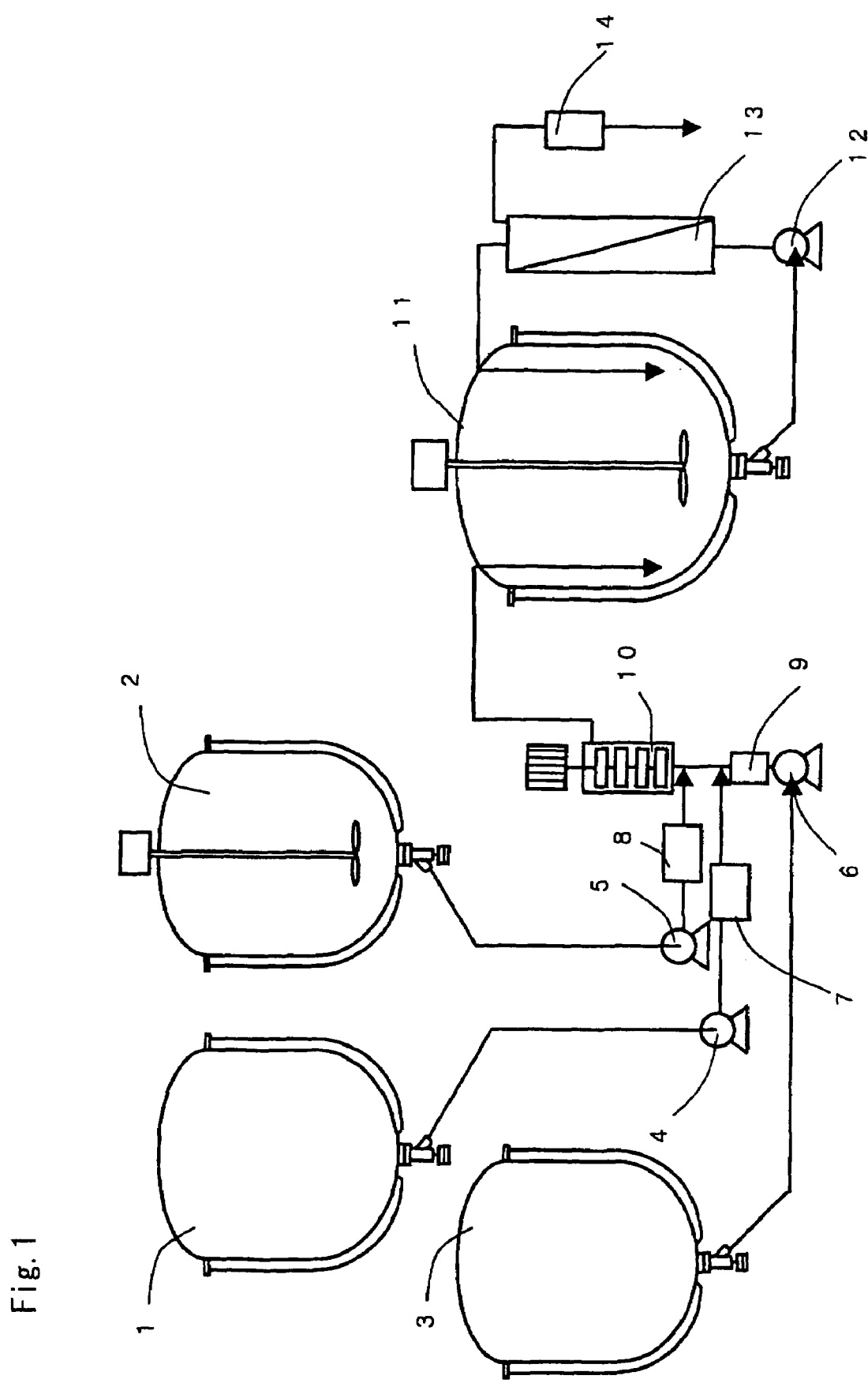
FIG. 1 is a schematic view showing an exemplary structure of an apparatus used for the preparation of organic acid silver salt grains according to the present invention.

Hereafter, the methods for producing grains of silver salt of an organic acid, preparation apparatuses and method for preparing a thermally processed image recording material of the present invention will be explained in detail.

The methods for producing grains of silver salt of an organic acid of the present invention comprise a step of reacting a solution containing silver ions and a solution containing an alkali metal salt of an organic acid.

The "solution containing silver ions" used in the present invention means a solution containing silver ions in water or a mixture of water and an organic solvent. As the ion source of the solution containing silver ions, a water-soluble silver salt can be used. As the water-soluble silver salt, silver nitrate is preferably used. The concentration of the silver salt in the solution containing silver ions is preferably 0.03–6.5 mol/L, more preferably 0.1–5 mol/L. The pH of the solution containing silver ions is preferably 2–6, more preferably 3.5–6. For the pH adjustment, acids and alkalines usually used for pH adjustment may be added to the solution containing silver ions. The solution containing silver ions preferably has a Reynolds number in the range of 500–20,000, when the solution containing silver ions is supplied.

As the solvent of the solution containing silver ions used for the present invention, either water or a mixture of water and an organic solvent is used. The organic solvent used for the solution containing silver ions is not particularly limited so long as it is miscible with water. However, those degrading photographic performance are not preferred. While preferred solvents are water-miscible alcohols and acetone, a tertiary alcohol having 4–6 carbon atoms is preferably used. When a tertiary alcohol having 4–6 carbon atoms is used, the tertiary alcohol constitute 70 volume % or less, preferably 50 volume % or less, of the total volume of the solution containing silver ions. Temperature of the solution containing silver ions is preferably 0–50° C., more preferably 5–30° C. When a solution containing silver ions and an aqueous tertiary alcohol solution of organic acid alkali metal salt are simultaneously added as described below, the temperature is most preferably 5–15° C.

The "solution containing an alkali metal salt of an organic acid" means a solution or suspension containing an alkali metal salt of an organic acid in water, organic solvent or a mixture of water and an organic solvent. The organic acid moiety for the alkali metal salt of an organic acid is selected from those stable to light at an ambient temperature as a silver salt, but when its silver salt is heated at 80° C. or higher in the presence of a light exposed photocatalyst (e.g., latent images of photosensitive silver halide) and a reducing agent, it produces a silver image. The organic acid is preferably a long chain aliphatic carboxylic acid containing 10–30 carbon atoms, more preferably 15–28 carbon atoms. Preferred examples of the aliphatic carboxylic acid include cerotic acid, lignoceric acid, behenic acid, erucic acid, arachidic acid, stearic acid, oleic acid, lauric acid, caproic acid, myristic acid, palmitic acid, maleic acid, fumaric acid, tartaric acid, linolic acid, butyric acid, camphoric acid and mixtures thereof. More preferred are behenic acid, arachidic acid, stearic acid, oleic acid, lauric acid, caproic acid, myristic acid, palmitic acid, and mixtures thereof.

As the alkali metal moiety for the alkali metal salt of an organic acid, sodium, potassium and so forth can be mentioned. An alkali metal salt of an organic acid can be prepared by adding sodium hydroxide, potassium hydroxide or the like to an organic acid. In this treatment, it is preferable to use the alkali in an amount less than the equivalent of the organic acid to remain unreacted organic acid. In this case, the amount of the remaining organic acid is preferably 3–50 mole %, more preferably 3–30 mole %, with respect to the total organic acid. Further, it may be prepared by adding an alkali in an amount exceeding the desired amount, and then adding an acid such as nitric acid and sulfuric acid to neutralize excessive alkali substance.

The concentration of the alkali metal salt of an organic acid in the solution containing an alkali metal salt of an organic acid used for the present invention is preferably 5–50 weight %, more preferably 7–45 weight %, further preferably 10–40 weight %. The solvent used for the solution containing an alkali metal salt of an organic acid used for the present invention may be any one of water, an organic solvent and a mixture of water and an organic solvent. When a mixture of water and an organic solvent is used, the amount of the organic solvent is preferably 3–70 volume %, more preferably 5–50 volume %, with respect to the volume of water. In this case, since the optimum solvent volume varies depending on the reaction temperature, the optimum amount is desirably determined trial-and-error basis.

In the present invention, a mixed solvent of water and a tertiary alcohol having preferably not more than 15 carbon atoms, more preferably not more than 10 carbon atoms, particularly preferably 4 to 6 carbon atoms, is preferably used as the solvent of the solution containing an alkali metal salt of an organic acid for ensuring uniformity of the solution. Tertiary alcohols in which the number of carbon atoms exceeds 6 may not be preferred since their miscibility with water becomes poor. Among the tertiary alcohols having 4 to 6 carbon atoms, most preferred is tert-butanol as its miscibility with water is the highest of all. Alcohols other than such tertiary alcohols may also be unfavorable since they have a reducing property and adversely affect the process of forming the silver salt of an organic acid.

Temperature of the solution containing an alkali metal salt of an organic acid, which is added for the reaction, is preferably maintained at a temperature required for avoiding crystallization or solidification of the alkali metal salt of an organic acid. Specifically, it is preferably 50–90° C., more preferably 60–85° C., most preferably 65–85° C. Further, the temperature is preferably controlled to be a constant temperature within the aforementioned range in order to control the reaction temperature to be constant. For the pH adjustment, acids and alkalines usually used for pH adjustment may be added to the solution containing an alkali metal salt of an organic acid.

The solution containing silver ions and the solution containing an alkali metal salt of an organic acid used for the present invention may be added with compounds of the formula (1) described in JP-A-62-65035, water-soluble group-containing N-heterocyclic compounds such as those described in JP-A-62-150240, inorganic peroxides such as those described in JP-A-50-101019, sulfur compounds such as those described in JP-A-51-78319, disulfide compounds such as those described in JP-A-57-643, hydrogen peroxide and so forth.

The "reaction field solution" used for the present invention consists of water or a mixed aqueous solution of water and an organic solvent. The reaction field solution may contain a dispersing agent and so forth, and it may be a recycled portion of the organic acid silver salt solution obtained in the reaction.

In the present invention, the silver salt of an organic acid is prepared by reacting a solution containing silver ions and a solution containing an alkali metal salt of an organic acid in mixing means. Since sealed mixing means is preferably used as the mixing means, the present invention will be explained by referring to a case utilizing sealed mixing means.

The method for preparing a silver salt of an organic acid by reacting a solution containing silver ions and a solution containing an alkali metal salt of an organic acid may be any one of a method of gradually or rapidly adding a solution containing silver ions into sealed mixing means containing a solution containing an alkali metal salt of an organic acid, a method of gradually or rapidly adding a preliminarily prepared solution containing an alkali metal salt of an organic acid into sealed mixing means containing a solution containing silver ions, and a method of simultaneously adding preliminarily prepared solution containing an alkali metal salt of an organic acid and solution containing silver ions into sealed mixing means. The addition rate may be constant, or it may vary as a function of time. When it varies as a function of time, accelerative addition method, deaccelerative addition method or combination thereof may be used.

A preferred method is a method in which the process contains a period where the solution containing silver ions and the solution containing an alkali metal salt of an organic acid are simultaneously added to sealed mixing means (simultaneous addition method). According to the simultaneous addition method, mean grain size of the silver salt of an organic acid can be controlled to achieve narrow grain size distribution. In the simultaneous addition method, it is desirable that 10–100 volume %, more preferably 30–100 volume %, particularly preferably 50–100 volume %, of the total volume to be added is simultaneously added. It is preferable to simultaneously add the solution containing silver ions and the solution containing an alkali metal salt of an organic acid in substantially equimolar amounts. In a case where either one is added in advance, it is desirable that the solution containing silver ions is added first. The amount added in advance is preferably from 0–50 volume %, more preferably from 0–25 volume %, of the total amount to be added. Furthermore, a method described in JP-A-9-127643 wherein pH or silver potential of the reaction mixture is controlled during the reaction may be preferably used.

In the second preparation method of the present invention, the solution containing silver ions is supplied to the reaction field solution at a stage before the sealed mixing means, and then the solution containing an alkali metal salt of an organic acid is supplied to the reaction field solution or the sealed mixing means. When the solution containing an alkali metal salt of an organic acid is supplied and mixed with the solution containing silver ions, silver ions constituting the silver salt of an organic acid must be already present in the reaction field. By using the second preparation method, the organic acid alkali metal salt is effectively prevented from being deposited as they are as coarse grains.

In the preparation methods of the present invention, as for the silver/alkali metal ratio after the reaction of the solution containing silver ions and the solution containing an alkali metal salt of an organic acid, it is preferred that the alkali should be excessive by 1–20 mole %, more preferably 1–10 mole %. Further, the concentration of the grains of organic acid silver salt immediately after the reaction is preferably 1–20 weight %, more preferably 1–10 weight %.

Other than the above, there are various approaches as the method for forming organic acid silver salt grains. To obtain organic acid silver salt grains, it is generally preferable to make solubility of the organic acid silver salt in the reaction field small. Further, according to the study of the inventors of the present invention, it has been revealed that the size of the formed organic acid silver salt grains becomes smaller as the addition time of the solution containing silver ions or the solution containing organic acid alkali metal salt becomes longer. In order to obtain organic acid silver salt grains in a desired size, the reaction time must be determined by try and error. Further, in the present invention, the reaction conditions are preferably controlled so that the concentration of the organic acid silver salt grains immediately after the reaction should become 1–10 weight %.

In the sealed mixing means, a solvent (reaction field solution) can be placed beforehand prior to the addition of the solution containing silver ions or the solution containing organic acid alkali metal salt. While wafer is usually used as the solvent placed beforehand, a mixed solution with the organic solvent used for the solution containing silver ions and the solution containing organic acid alkali metal salt may also be used. In addition, in order to produce organic acid salt grains, it is preferable to add an organic solvent to at least one of the solution containing silver ions, the solution containing organic acid alkali metal salt and the solution prepared in the reaction field beforehand in such an amount that the alkali metal salt of an organic acid can be present so as to form a substantially transparent solution without forming linear aggregates or micelles. Further, water and a tertiary alcohol preferably exist in the reaction mixture when the solution containing silver ions and the solution containing an organic acid alkali metal salt are added. In this case, the carbon number of the tertiary alcohol is preferably 15 or less, more preferably 10 or less, particularly preferably 4–6. Further, the ratio of the tertiary alcohol to wafer is preferably 0.01–10, more preferably 0.03–1.

Temperature of the liquid contained in the sealed mixing means is preferably 5° C. to 75° C., more preferably 6° C. to 60° C., most preferably 10° C. to 50° C., in order to improve performance as a photographic photosensitive material. Throughout the entire process of the reaction, the reaction temperature is preferably controlled to be a constant temperature selected from the above-defined range. As the case may be, however, the reaction temperature may be controlled in some temperature profiles varying within the above-defined range.

The temperature difference between the solution containing an alkali metal salt of an organic acid and the liquid in the sealed mixing means is preferably 20° C. to 85° C., more preferably 30° C. to 80° C. In this case, it is desirable that the temperature of the solution containing an alkali metal salt of an organic acid should be higher than that of the liquid contained in the sealed mixing means. By performing the process as described above, the rate at which the solution containing an alkali metal salt of an organic acid having a higher temperature is rapidly cooled by the reaction vessel and precipitated to give fine crystals, and the rate at which an organic acid silver salt is formed by the reaction with the water-soluble silver salt are both favorably controlled, and thereby the crystal morphology, crystal size and crystal size distribution of the organic acid silver salt can be favorably controlled. In addition, the properties of the thermally processed image recording material, in particular, photothermographic image recording material, can also be improved simultaneously.

In order to prepare scaly silver salt of an organic acid preferred for the present invention, for example, when a solution containing silver ions is reacted with a tertiary alcohol aqueous solution containing an alkali metal salt of an organic acid in sealed mixing means (the method includes a step of adding the aqueous tertiary alcohol solution containing an alkali metal salt of an organic acid into a liquid contained in sealed mixing means), the temperature difference between the liquid already existing in the sealed mixing means and the aqueous tertiary alcohol solution of an alkali metal salt of an organic acid to be added thereto is controlled to be between 20° C. and 85° C., wherein the liquid in the reaction vessel is a solution containing silver ions put into the reaction vessel in advance, or alternatively, the liquid is water or a mixed solvent of water and a tertiary alcohol in a case where the solution containing silver ions is not put into the reaction vessel in advance but is added from the beginning simultaneously with an aqueous solution of an alkali metal salt of an organic acid in a tertiary alcohol, and when the solution containing silver ions is put into the reaction vessel in advance, water or a mixed solvent of water and a tertiary alcohol may be placed in advance.

By maintaining the temperature difference during the addition of the aqueous tertiary alcohol solution containing an alkali metal salt of an organic acid, the crystal morphology of the silver salt of an organic acid or the like can be favorably controlled. The tertiary alcohol may be added in any timing during the preparation of the organic acid silver salt. However, the tertiary alcohol is preferably added at the time of preparation of the organic acid alkali metal salt to dissolve the organic alkali metal salt. The tertiary alcohol may be added in any amount of from 0.01 to 10 as weight ratio based on the weight of water used as a solvent for the preparation of the organic acid silver salt, and preferably added in an amount of from 0.03 to 1.

In order to rapidly lower the liquid temperature of the reaction mixture after the reaction of the solution containing silver ions and the solution containing organic acid alkali metal salt, the solution containing silver ions and the solution containing organic acid alkali metal salt supplied to the sealed mixing means may be cooled beforehand. Further, cooling may be attained by providing a heat exchanger for the sealed mixture means itself or between the sealed mixing means and a tank or a position before the sealed mixing means. The liquid temperature after the reaction of the solution containing silver ions and the solution containing organic acid alkali metal salt is preferably 5–70° C., more preferably 10–50° C., particularly preferably 20–45° C. Further, the as for the cooling rate, performance as a photosensitive material can further be improved, if the temperature reached a desired temperature within 0.05–10 seconds, preferably 0.05–5 second, further preferably 0.05–1 second, after the reaction solutions are brought into contact with each other.

In the methods of the present invention, a dispersing agent is preferably added to the system before the start of the reaction of the solution containing silver ions and the solution containing organic acid alkali metal salt or before completion of the purification using an ultrafiltration membrane. The addition method is not particularly limited. For example, the dispersing agent may be contained in one to three kinds among the solution containing silver ions, the solution containing organic acid alkali metal salt and the solution put into the reaction vessel beforehand. The dispersing agent may also be added separately as a dispersing agent, or added as an additive comprising the dispersing agent and other components. When such a dispersing agent or additive is added, any one of water, organic solvent and mixture of water and an organic solvent may be used as a solvent. These addition methods may be used in any combination.

The type of the dispersing agent used for the present invention is not particularly limited. For example, dispersing agents having a molecular weight of more than 3000 can be used. Such a dispersing agent can suitably be selected for use from known polymers, for example, synthetic anionic polymers such as polyacrylic acid, naphthalenesulfonic acid polymers, copolymers of acrylic acid, maleic acid copolymers, maleic acid monoester copolymers and copolymers of acryloylmethylpropane-sulfonic acid; semi-synthetic anionic polymers such as carboxymethyl starch and carboxymethyl cellulose; anionic polymers such as alginic acid and pectic acid; other polymers including polyvinyl alcohol (e.g., PVA-217 (trade name), mean polymerization degree: about 1700), polyvinylpyrrolidone, carboxymethyl cellulose, hydroxypropyl cellulose, hydroxy-propylmethyl cellulose etc., naturally occurring macromolecular compounds such as gelatin and so forth.

In the present invention, a nonionic macromolecular dispersing agent is preferably used. More preferred is a nonionic macromolecular dispersing agent soluble in an aqueous reaction medium, which can disperse a silver salt of an organic acid and has a molecular weight of 5 times to 10 times the fractional molecular weight of an ultrafiltration membrane used for the desalting of the by-product salts produced from the reaction of the solution containing silver ions and the solution containing an alkali metal salt of an organic acid. As such a dispersing agent, polyvinyl alcohol, polyvinylpyrrolidone; hydroxyethyl cellulose and hydroxypropyl cellulose can preferably be used.

The concentration of the dispersing agent used in the present invention is preferably 0.1–30 weight %, particularly preferably 0.5–30 weight %, of the silver salt of an organic acid. While the addition time of the dispersing agent is not particularly limited, it is preferably added after completion of the reaction of the silver salt of an organic acid and before completion of the ultrafiltration operation in order to prevent inhibition of the reaction of the silver salt of an organic acid.

The organic acid silver salt is extremely hydrophobic, and therefore, if the system does not contain a dispersing agent, crosslinking of the grains proceeds with time, and aggregation may remarkably advance by a certain shearing field or pressure field during feeding operation or filtration through an ultrafiltration membrane described later. Further, in a strong ion strength environment before the desalting operation, surface charge of the organic acid silver salt grains is shielded, and hence they may be brought into a condition under which they are further likely to aggregate. In order to ameliorate this condition, it is desirable that pH is selected to be high so that dissociation of the species present on the grain surfaces should be accelerated. However, if the alkalinity in the environment becomes unduly high, the actions of silver oxide or reducing agent as impurity will be increased, and thus they cause fog. Therefore, in order to prevent the aggregation, pH of the dispersion must be maintained to be 6 or higher, preferably 6–8, until the electric conductivity reaches a level less than 2,000 $\mu$S/cm and not less than 500 $\mu$S/cm in the desalting operation by ultrafiltration. Even though a dispersing agent is used, pH of the dispersion is preferably controlled within this range.

In the methods of the present invention, the organic acid silver salt dispersion may be subjected to mechanical dispersion process using a dispersing machine within such a degree that the photographic performance should not be degraded. The dispersing method is preferably one comprising preparing a dispersion of the silver salt of an organic acid, forming a high-pressure and high-speed flow of the dispersion, and re-dispersing the salt by lowering the pressure to form a fine aqueous dispersion of the salt. In this case, the dispersion medium preferably consists of water alone, but may contain an organic solvent so long as it is in an amount of 20 weight % or less of the dispersion medium.

The dispersing machines and techniques used for performing the above-described re-dispersion method are described in detail, for example, in Toshio Kajiuchi and Hiromoto Usui, Bunsan-kei Rheology to Bunsanka Gijutsu (Rheology of Dispersion System and Dispersion Technology), pp. 357–403, Shinzan Sha Shuppan (1991), and Kagaku Kogaku no Shinpo (Progress of Chemical Engineering), vol. 24, pp. 184–185, compiled by Corporation Kagaku Kogakukai Tokai Shibu, Maki Shoten (1990), JP-A-59-49832, U.S. Pat. No. 4,533,254, JP-A-8-137044, JP-A-8-238848, JP-A-2-261525, JP-A-1-94933 and so forth. The re-dispersion method used in the present invention comprises at least the steps of supplying an aqueous dispersion containing a silver salt of an organic acid into a pipeline under a positive pressure by means of a high-pressure pump or the like, passing the dispersion through a narrow slit provided inside the pipeline, and then subjecting the dispersion to rapid pressure release to perform fine dispersion.

In the third preparation method of the present invention, the organic acid silver salt is dispersed as fine grains in the presence of a dispersing agent by using pulverization means. Examples of the pulverization means include high-speed mixer, homogenizer, high-speed impact mill, Banbary mixer, homomixer, kneader, ball mill, vibrating ball mill, planetary ball mill, attriter, sand mill, bead mill, colloid mill, jet mill, roller mill, trone mill, high-speed stone mill, high-pressure homogenizer, ultrasonic dispersing machine and so forth. In the third preparation method of the present invention, at least high-pressure homogenizer or high-speed rotary type homomixer is used for dispersion.

The high-pressure homogenizer is an apparatus for dispersing a dispersion system at a high pressure and high speed, in which large shearing force is applied to the dispersion system. Dispersion is attained with high pressure and high speed in a high pressure grinding section provided in the way of dispersion route, dispersion, emulsification and grinding are attained by passing a dispersion through a narrowed part of dispersion route at high pressure and high speed, or dispersions are collided with each other in a dispersion route.

As for the high-pressure homogenizer, it is generally considered that fine and uniform dispersion can be efficiently achieved therein by enhancing (a) "shear force" to be generated at the passage of a dispersoid through a narrow slit (75 $\mu$m to 350 $\mu$m or so) under high pressure at high speed and (b) "cavitation force" to be generated by the pressure releasing, but without changing the preceding impact force resulting from the liquid-liquid collision or the liquid-wall collision in the high-pressure narrow space. One old example of the dispersion apparatus of this type is a Golline homogenizer. In this apparatus, a liquid to be dispersed introduced under high pressure is converted into a high-speed flow when it is passed through a narrow gap formed on the wall of a cylindrical surface. Then, the flow collides against a surrounding wall with its own force, and is emulsified and dispersed by the impact force. For the liquid-liquid collision mentioned above, for example, there can be mentioned a Y-type chamber of Microfluidizer, a spherical chamber utilizing a spherical check valve such as that described in JP-A-8-103642 and so forth. For the liquid-wall collision, there can be mentioned a Z-type chamber of Microfluidizer and so forth. The pressure is generally 100 to 600 kg/cm$^2$, and the flow rate is generally a few meters/sec to 30 meters/sec. In order to increase the dispersion efficiency, some apparatuses are designed wherein the high flow rate area is so modified as to have a serrated configuration, thereby increasing the frequency of collision. Typical examples of such apparatuses are Golline homogenizer (15MR-8TA produced by Golline, produced by APV), High pressure homogenizer (produced by Izumi Food Machinery Co., Ltd.), Microfluidizer produced by Microfluidex International Corporation, Microfluidizer from Mizuho Kogyo Co. Ltd., Nanomizer from Tokushu Kika Kogyo Co., Ltd, Nanomizer LA53 produced by Nanomizer Co., Ltd., Nanomizer produced by Cosmo Keiso Co., Ltd, high pressure homogenizer such as Genus PY produced by Genus Co., Ltd. and so forth. Other examples of such apparatuses are described in JP-A-8-238848, JP-A-8-103642 and U.S. Pat. No. 4,533,254.

In dispersing process of the organic acid silver salt, dispersion having a desired grain size may be obtained by controlling the flow rate, the difference in the pressure before and after at the pressure releasing and the frequency of the processing. The flow rate is preferably from 100 to 600 m/sec and the difference in pressure at the pressure releasing is preferably from 200 to 3,000 kg/cm$^2$.

Examples of high speed rotary type homomixer include high-speed shearing mixer produced by Tokushu Kika Kogyo Co., Ltd. (trade name: TK Homomixer), Milder MDN 303V produced by Ebara Corp. and so forth. While the rotation number may vary depending on capacity of dispersing machine, size of impellers and so forth, it is preferably about 1000–30000 rpm.

It is not preferable to expose such an aqueous dispersion to a high temperature under a high pressure in view of dispersibility and photographic performance. At a high temperature above 90° C., a grain size may readily become large and fog may be increased. Accordingly, the water dispersion is preferably kept at a temperature of from 5° C. to 90° C., more preferably from 5° C. to 80° C., particularly preferably from 5° C. to 65° C., by a cooling step using a cooling apparatus during or after the dispersion in a high-pressure homogenizer or high-pressure rotary homomixer. The cooling apparatus may be appropriately selected from a double pipe or triple pipe with a static mixer, a multi-tubular heat exchanger, a coiled heat exchanger and so forth depending on an amount of heat exchange to be required. The size, wall thickness or material of pipes may be appropriately selected to increase heat exchange efficiency depending on an applied pressure. In addition, depending on an amount of heat exchange, a refrigerant used in the cooling apparatus may be a well water at 20° C. or a chilled water at from 5 to 10° C. cooled by a refrigerator, and if desired, a refrigerant such as ethylene glycol/water at −30° C. may also be used.

When a photosensitive silver halide salt coexists at the time of dispersing process of the silver salt of an organic acid, fog may increase and sensitivity may markedly decrease. Therefore, the dispersion during the dispersing process preferably contains substantially no photosensitive silver halide salt. The amount of photosensitive silver halide salt in the aqueous dispersion during the dispersing operation is desirably 0.1 mole % or less per 1 mole of silver salt of an organic acid in the dispersion, and it is desirable not to intentionally add photosensitive silver halide salt.

Other than the mechanical dispersion, the silver salt of an organic salt can be made into grains by roughly dispersing the salt in a solvent through pH control, and then changing the pH in the presence of a dispersing aid. For the operation, an organic solvent may be used as a solvent for the rough dispersion, and such organic solvent is usually removed after the formation of grains.

In the preparation methods of the present invention, the by-product salts contained in the reaction mixture is preferably removed by ultrafiltration during the reaction of silver ions and organic acid alkali metal salt or after completion of the reaction. Further, in the third preparation method of the present invention, ultrafiltration is performed after or during the aforementioned dispersion operation.

As the method for ultrafiltration performed in the present invention, methods used for desalting and concentration of silver halide emulsion, and for example, those methods described in Research Disclosure, No. 10208 (1972), No. 13122 (1975), No. 16351 (1977) etc. can be used. While pressure difference and flow rate, which are important as the operational conditions, can be selected by referring to the characteristic curves mentioned in Haruhiko Oya, "Maku Riyo Gijutsu Handbook (Membrane Utilization Technique Handbook)", published by Saiwai Shobo (1978), p. 275, it is necessary to find out optimum conditions for treating an organic acid silver salt dispersion of interest in order to suppress aggregation of grains, fog and so forth.

As an ultrafiltration membrane, modules of plate type, spiral type, cylinder type, hollow yarn type, hollow fiber type and so forth, in which a membrane is already incorporated, are commercially available from Asahi Chemical Industry Co., Ltd., Daicel Chemical Industries, Ltd., Toray Industries, Inc., NITTO DENKO CORP. and so forth. In view of the total membrane area, washability and so forth, those of hollow yarn type and spiral type are preferred.

Examples of the material of ultrafiltration membrane include polysulphone, polyphenyl sulphone, polyether sulphone, polyacrylonitrile and so forth, and examples of module type include flat membrane, hollow yarn membrane, tubular membrane and so forth. The fractional molecular weight, which is an index of a threshold for substances that can permeate a membrane, must be determined based on the molecular weight of the used dispersing agent. In the present invention, those having a fractional molecular weight of 1,500–50,000, more preferably 4,000–50,000, are preferably used.

In the present invention, it is preferable to perform the desalting treatment after the organic acid silver salt grains immediately after the reaction is concentrated to a concentration of 15–40 weight %, preferably 15–25 weight %. Further, the liquid temperature after the grain formation is preferably kept low until the desalting operation proceeds. This is because silver nuclei are likely to be formed by the shearing force field and the pressure field during the feeding of dispersion or passage through an ultrafiltration membrane under a condition that the solvent used for dissolving the alkali metal salt of an organic acid permeates in the produced organic acid silver salt grains. For this reason, in the present invention, the ultrafiltration operation is desirably performed while the temperature of the organic acid silver salt grain dispersion is kept at 1–30° C., preferably at 5–25° C.

As a method for supplementing the solvent lost due to passage through the membrane, there may be employed either the constant volume method where the solvent is continuously supplemented, or the batch method where the solvent is intermittently added. The constant volume method is preferred in the present invention because of its relatively shorter desalting treatment time. The solvent to be supplemented as described above comprises pure wafer obtained by ion exchange or distillation, which may contain a pH modifier. However, if the desalting operation is performed by dilution with pure water during the ultrafiltration operation, the concentration of the dispersing agent is reduced and hence aggregation may be caused. Therefore, a surfactant is preferably supplemented in order to maintain a certain level of surfactant concentration to prevent the aggregation. In particular, because the organic acid silver salt grains are in a state that they are likely to aggregate in the high salt concentration circumstance of the early stage of the desalting operation with the presence of an organic solvent such as tertiary alcohol, the concentration of anionic surfactant, for example, is preferably maintained at a level 5 to 100 times as high as the critical micelle concentration. Specifically, while the concentration of leaking surfactant is quantified by spectrophotometry or liquid chromatography, a solution having the same concentration as the measured concentration may be continuously added as a replenisher, or a solution having a concentration higher than that may be added intermittently.

Further, since the silver salt of an organic acid is extremely hydrophobic, aggregation may markedly proceed under a shearing field or pressure field during the feeding operation and passage through an ultrafiltration membrane. Furthermore, in a high ionic strength circumstance in early stages of the desalting operation, the surface charge of the organic acid silver salt grains is shielded, and hence they become more likely to aggregate. In order to ameliorate this condition, when an anionic surfactant is added in advance, another ionic surfactant having anionic nature and a hydrophobic group with 8–40 carbon atoms different from the anionic surfactant added beforehand may be added during the desalting operation. As for the addition method, while the concentration of leaking surfactant is quantified by spectrophotometry or liquid chromatography, a solution having the same concentration as the measured concentration may be continuously added, or a solution having a concentration higher than that may be added intermittently, as described above.

If the fractional molecular weight of an ultrafiltration membrane is unknown, its rejection can be obtained by filtering a solution of a dispersing agent to be used, and calculating the rejection from the concentration of the surfactant leaked into the filtrate. When a surfactant is used, the rejection R of an ultrafiltration membrane is defined by the following equation:

$$R = (C_i - C_o)/C_i \times 100 \, [\%]$$

wherein $C_i$ represent a concentration in original dispersion, and $C_o$ represents a leaked concentration in the filtrate.

The rejection is preferably less than 50% for the methods of the present invention.

In a preferred embodiment, a nonionic macromolecular dispersing agent, for example, may be added after the desalting is performed by ultrafiltration and thus electric conductivity of the organic acid silver salt dispersion is lowered, but before completion of the desalting operation. At this time, the conductivity is preferably 2000 μS/cm or less. In this case, in order to remove anionic surfactant and replace it with a nonionic macromolecular dispersing agent, there is preferably performed an operation of adding pure water in an amount corresponding to the amount of the anionic surfactant solution passed through the ultra filtration membrane, i.e., the so-called constant volume dilution, in an order of 2- to 20-fold.

In the present invention, it is also possible to carry out the ultrafiltration operation while adding a poor solvent for the dispersing agent used after the conductivity has reached a level below 1,000 μS/cm with the progress of the desalting.

Under a low ionic strength circumstance, aggregation is not caused even if the protection effect of the dispersing agent is reduced, because stabilizing effect is exerted by electric charge on the grain surfaces. In addition, the viscosity of the whole dispersion becomes high due to increase of repulsion between the grains, and therefore the filtration operation becomes difficult. In order to avoid this phenomenon, it is desirable to add the poor solvent for the dispersing agent.

After the removal of by-product salts by ultrafiltration, the dispersion can be further concentrated by ultrafiltration. In particular, after the electric conductivity comes to be 20 μS/cm or more to less than 300 μS/cm due to the removal of by-product salts by the ultrafiltration, the dispersion can be preferably concentrated to a concentration of 10–50 weight %, more preferably 10–30 weight %.

In the present invention, metal ions selected from Ca, Mg, Ce, Al, Zn and Ba are preferably added in the form of a water-soluble metal salt, which is not a halide compound. Specifically, they are preferably added in the form of nitrate or sulfate. Time of the addition of the metal ions selected from Ca, Mg, Ce, Al, Zn and Ba is not particularly limited, and they may be added any time. For example, they may be added to a liquid of organic acid silver salt preparation, preliminarily added to a reaction mixture, added during or immediately after the formation of the organic acid silver salt, or immediately before the coating, i.e., before or after the formation of coating solution. The amount is preferably $10^{-3}$ to $10^{-1}$ mole, particularly preferably $5 \times 10^{-3}$ to $5 \times 10^{-2}$ mole, per one mole of the organic acid silver salt.

The prepared dispersion can be stored with stirring to prevent precipitation of the grains during storage, or stored in a highly viscous state formed by means of hydrophilic colloids (e.g., a jelly state formed with gelatin). Furthermore, the dispersion may contain a preservative in order to prevent proliferation of microorganisms during storage.

The silver salt of an organic acid solid fine grain dispersion used in the present invention comprises at least a silver salt of an organic acid and water. While the ratio of the silver salt of an organic acid to water is not particularly limited, it must be decided based on rheological characteristics for stable coating and production speed determined by dry moisture content in view of efficient formation of coated films. The silver salt of an organic acid preferably accounts for from 10–50 weight %, particularly preferably from 10–30 weight % of the entire dispersion.

The dispersion of organic acid silver salt grains prepared by the preparation methods of the present invention is preferably finely dispersed in an aqueous solvent, and then mixed with an aqueous solution of a photosensitive silver halide salt to provide a coating solution for photosensitive image-forming layer of a photothermographic material. Such a coating solution enables the manufacture of a thermally processed image recording material exhibiting low haze and low fog, and showing high sensitivity. When a photosensitive silver halide salt coexists at the time of finely dispersing the silver salt of an organic acid by converting the dispersion into a high-speed flow under a high pressure, fog may increase and sensitivity may markedly decrease. Therefore, the aqueous dispersion that is dispersed by converting it into a high-speed flow under high pressure preferably contains substantially no photosensitive silver halide salt. Furthermore, when an organic solvent is used as a dispersion medium instead of water, haze and fog may increase and sensitivity may be likely to decrease. On the other hand, when the conversion method where a part of the silver salt of an organic acid in the dispersion is converted into a photosensitive silver halide salt is used instead of the method of mixing an aqueous photosensitive silver halide salt solution, sensitivity may be decreased.

The shape of the silver salt of an organic acid that can be used for a thermally processed image recording material, I particular, photothermographic material, is not particularly limited, and scaly grains, acicular grains, rod-like grains and tabular grains can be mentioned. However, scaly silver salt of an organic acid is preferred. Scaly silver salt of an organic acids are herein defined as follows. A sample of a silver salt of an organic acid to be analyzed is observed with an electronic microscope, and grains of the salt seen in the field are approximated to rectangular parallelepipeds. The three different edges of each rectangular parallelepiped are represented as a, b and c where a is the shortest, c is the longest, and c and b may be the same. From the shorter edges a and b, x is obtained according to the following equation:

$$x=b/a$$

The values of x are obtained for about 200 grains, and an average of them (x (average)) is obtained. Samples that satisfy the requirement of x (average) $\geq 1.5$ are defined to be scaly. Scaly grains preferably satisfy $30 \geq x$ (average) $\geq 1.5$, more preferably $20 \geq x$ (average) $\geq 2.0$. In this connection, acicular (needle-like) grains falls satisfy $1 \leq x$ (average) <1.5.

In scaly grains, it is understood that a corresponds to the thickness of tabular grains of which main planes are defined by the sides of b and c. The average of a is preferably from 0.01 µm to 0.23 µm, more preferably from 0.1 µm to 0.20 µm. The average of c/b is preferably from 1 to 6, more preferably from 1.05 to 4, even more preferably from 1.1 to 3, particularly preferably from 1.1 to 2.

The organic acid silver salt grains prepared by the methods of the present invention and used for the preparation of the thermally processed image recording material preferably have a diameter as sphere of 0.1–0.8 µm, more preferably 0.1–0.6 µm. Further, they preferably have a ratio of long side length/short side length of grains of 1–4, more preferably 1–3, particularly preferably 1–2. Furthermore, the grains preferably have an aspect ratio (grain size for main plane (diameter as circle)/thickness of grain) of 2–30, more preferably 2–15. Further, the grains preferably have a thickness of is 0.01–0.20 µm, more preferably 0.01–0.15 µm. The grains are characterized by containing such grains satisfying the aforementioned requirements in an amount of 30–100%, more preferably 50–100%, particularly preferably 70–100%, in terms of a ratio to the projected area of total grains.

The grain size distribution of the silver salt of an organic acid is preferably monodispersed one as far as possible. When a coefficient of variation is defined as a value 100 times as large as a value obtained by dividing the standard deviation of grain size by the grain size, the coefficient of variation is preferably 20% or less, more preferably 18% or less, further preferably 15% or less. As for the measurement method, for example, the grain size (volume weight average diameter) can be determined by irradiating silver salt of an organic acid dispersed in a liquid with a laser ray and determining an autocorrelation function of the fluctuation of the scattered light on the basis of the change in time (the so-called dynamic light scattering method).

The grain size (volume weight average diameter) in an organic acid silver salt solid dispersion can be obtained form a grain size (volume weight average diameter) determined by, for example, irradiating silver salt of an organic acid dispersed in a liquid with a laser ray and determining an autocorrelation function of the fluctuation of the scattered light on the basis of the change in time. Preferred is a solid fine grain dispersion having a mean grain size of 0.05 to 10.0 µm, more preferably from 0.1 to 5.0 µm, further preferably from 0.1 to 2.0 µm.

Preparation apparatuses suitable for carrying out the preparation methods for organic acid silver salt grains according to the present invention will be specifically explained hereafter. Specific examples of preferred preparation apparatus will be mentioned below.

FIG. 1 shows a specific embodiment of a preparation apparatus suitable for carrying out the first preparation method of the present invention (first preparation apparatus). In the figure, a solution containing silver ions is put into a tank 1 for Additive component 1, a solution containing an alkali metal salt of an organic acid is put into a tank 2 for Additive component 2, and a reaction field solution is put into a tank 3 for Additive component 3. Each solution may be prepared in each tank, or it may be prepared outside the tank and then put into the tank. The solutions were fed into sealed mixing means 10 by pumps 4, 5 and 6, respectively. At this time, flow rates of the solutions are measured by flowmeters 7, 8 and 9, respectively, and controlled. The solutions introduced into the sealed mixing means 10 are mixed in the sealed mixing means and fed to the tank 11 for formed dispersion. The dispersion in the tank for formed dispersion 11 is further fed to an ultrafiltration module 13 by a pump 12 for circulation in ultrafiltration process and subjected to an ultrafiltration process. At this time, permeated water is measured by a flowmeter 14. The dispersion that underwent the ultrafiltration is returned to the tank for formed dispersion 11. The tank for formed dispersion 11 may be provided with a pipeline so that the reaction field solution can be introduced from a tank containing the reaction field solution.

Figure 2:
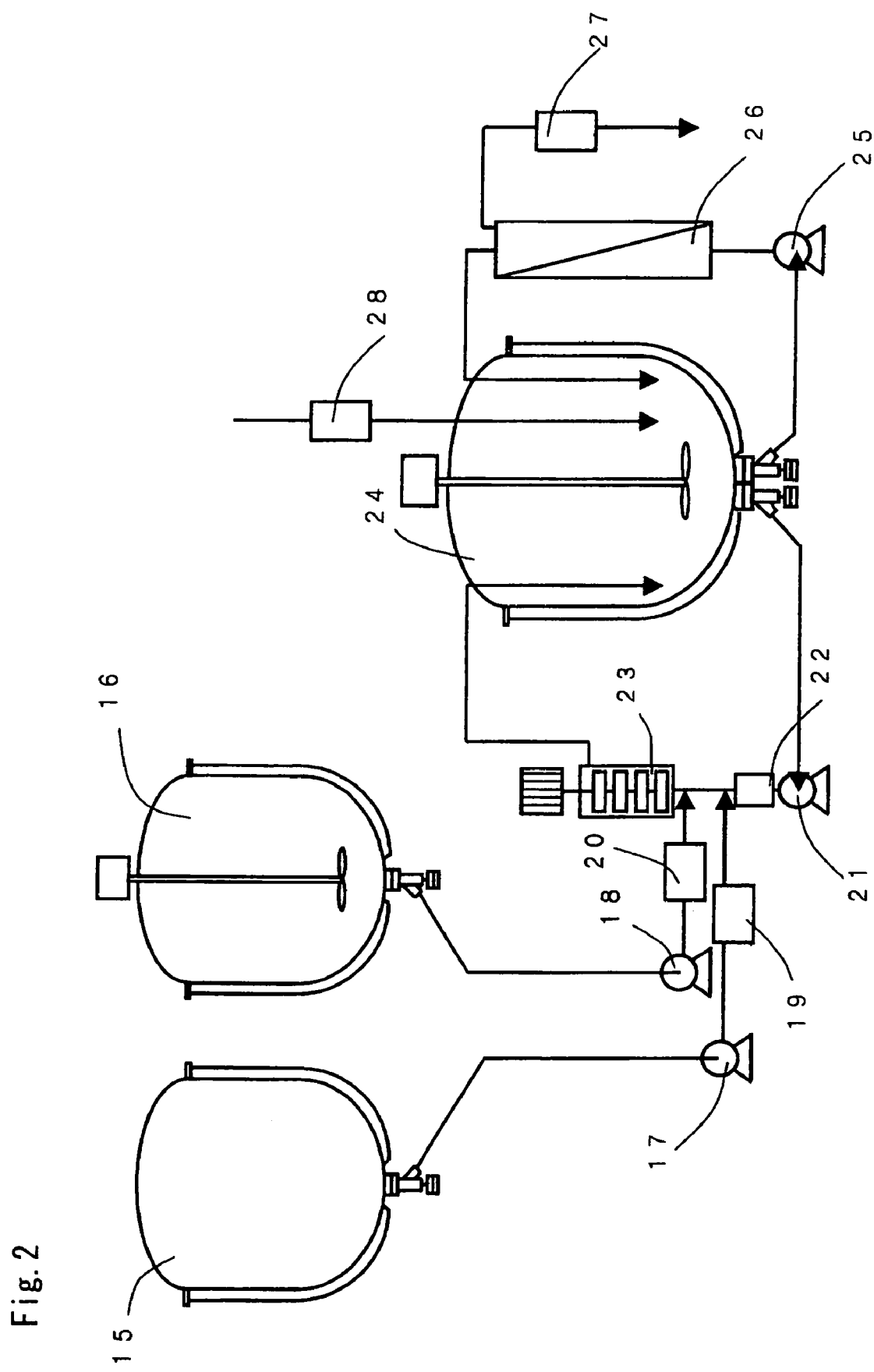
FIG. 2 is a schematic view showing another exemplary structure of an apparatus used for the preparation of organic acid silver salt grains according to the present invention.

FIG. 2 shows a specific embodiment of a preparation apparatus suitable for carrying out the second preparation method of the present invention (second preparation apparatus). In the figure, a solution containing silver ions is put into a tank 15 for Additive component 1, and a solution containing an alkali metal salt of an organic acid is put into a tank 16 for Additive component 2. The solutions were fed into sealed mixing means 23 by pumps 17 and 18, respectively. At this time, flow rates of the solutions are measured by flowmeters 19 and 20, respectively, and controlled. The solutions introduced into the sealed mixing means 23 are mixed in the sealed mixing means and fed to the tank 24 for formed dispersion. A part of the dispersion in the tank 24 for formed dispersion is fed to the sealed mixing means 23 again by a circulation pump 21, and its flow rate is measured by a flowmeter 22. Further, a part of the dispersion in the tank 24 for formed dispersion is introduced into an ultrafiltration module 26 by a pump 25 for circulation in ultrafiltration process and subjected to an ultrafiltration process. At this time, permeated water is measured by a flowmeter 27, and the dispersion that underwent the ultrafiltration is returned to the tank 24 for formed dispersion. Further, pure wafer is supplemented to the tank 24 for formed dispersion, and its flow rate is measured by a flowmeter 28.

Figure 3:
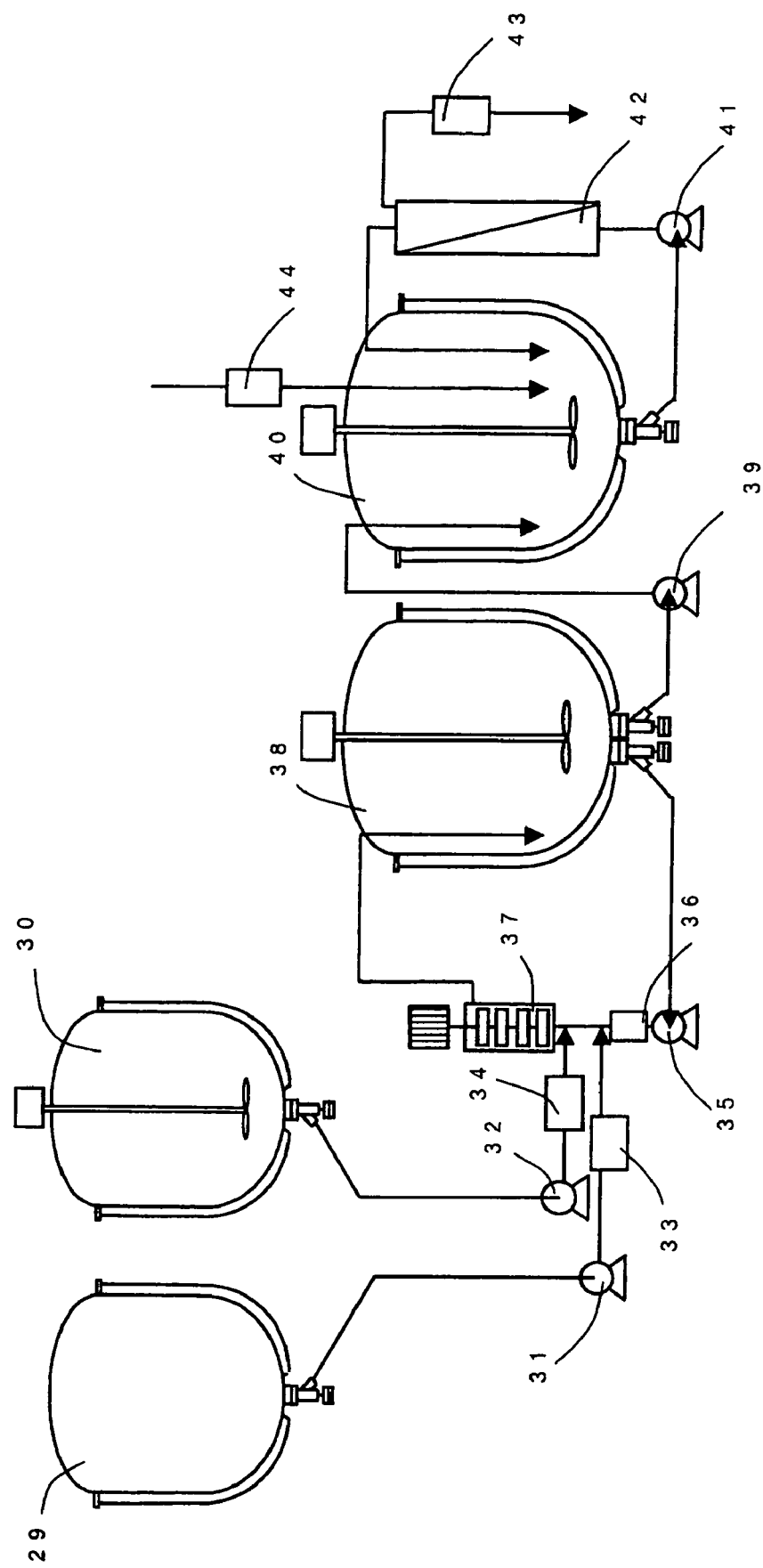
FIG. 3 is a schematic view showing a further exemplary structure of an apparatus used for the preparation of organic acid silver salt grains according to the present invention.

Further, FIG. 3 shows another specific embodiment of the second preparation apparatus. In the figure, a solution containing silver ions is put into a tank 29 for Additive component 1, and a solution containing an alkali metal salt of an organic acid is put into a tank 30 for Additive component 2. The solutions were fed into sealed mixing means 37 by pumps 31 and 32, respectively. At this time., flow rates of the solutions are measured by flowmeters 33 and 34, respectively, and controlled. The solutions introduced into the sealed mixing means 37 are mixed in the sealed mixing means and fed to the tank 38 for formed dispersion. A part of the dispersion in the tank 38 for formed dispersion is fed to the sealed mixing means 37 again by a circulation pump 35, and its flow rate is measured by a flowmeter 36. Further, a part of the dispersion in the tank 38 for formed dispersion is fed to a tank 40 for ultrafiltration process by a pump 39. The dispersion in the tank 40 for ultrafiltration process is fed into an ultrafiltration module 42 by a pump 41 and subjected to an ultrafiltration process. At this time, permeated water is measured by a flowmeter 43, and the dispersion that underwent the ultrafiltration is returned to the tank 40 for ultrafiltration process. Further, pure wafer is supplemented to the tank 40 for ultrafiltration process, and its flow rate is measured by a flowmeter 44.

The reaction mixture discharged from the sealed mixing means is stored in the tank for formed dispersion as storage means, and it may be directly fed to the ultrafiltration unit from the tank as shown in FIGS. 1 and 2, or it may be stored in a tank for ultrafiltration process other than the tank for formed dispersion, and then introduced into an ultrafiltration unit as shown in FIG. 3. By using the structure shown in FIG. 3, the tank for formed dispersion can be used as a preparation tank, and the tank for ultrafiltration process can be used as a ripening tank. This makes it possible to shorten the ripening time by increase of temperature, and it also becomes possible to wash the preparation tank for the subsequent process during the ripening. Thus, productivity can be improved. Further, grinding of the completed grains by high speed stirring is eliminated, and therefore it becomes possible to provide a thermally processed image recording material of high performance in which fog is suppressed. And simultaneously, bubbles are reduced thanks to the elimination of high speed stirring, and thus it is also possible to improve filtration rate in the ultrafiltration.

Figure 4:
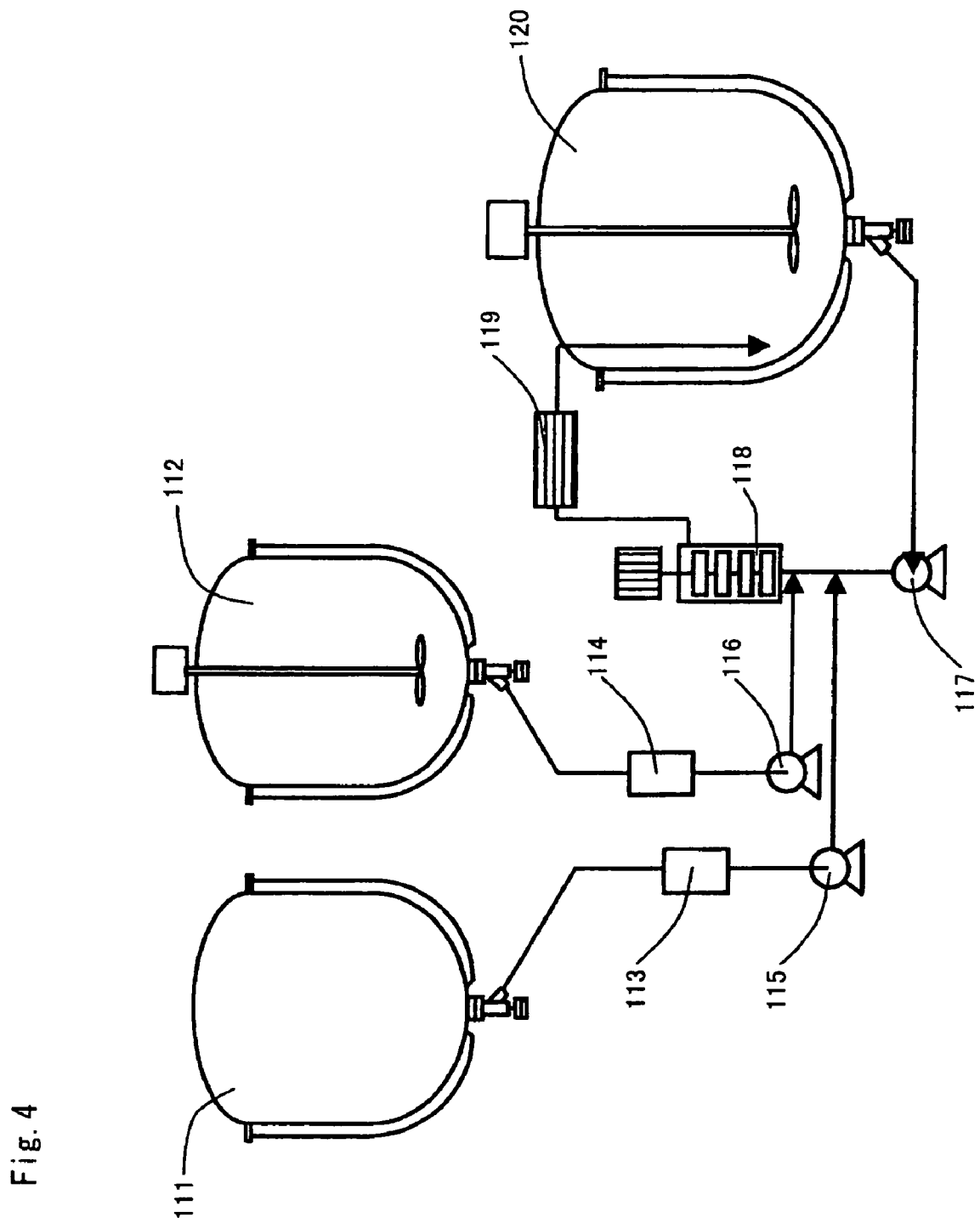
FIG. 4 is a schematic view showing a further exemplary structure of an apparatus used for the preparation of organic acid silver salt grains according to the present invention.

FIG. 4 shows a specific embodiment of the preparation apparatus suitable for carrying out the third preparation method of the present invention (third preparation apparatus). In the figure, a solution containing silver ions is put into a tank 111 for Additive component 1, and a solution containing an alkali metal salt of an organic acid is put into a tank 112 for Additive component 2. The solutions were fed into a pipeline for a reaction field solution and then sealed mixing means 118 by pumps 115 and 116, respectively. In this case, the solution containing silver ions is introduced into the pipeline for a reaction field solution at a position upstream from a position at which the solution containing an alkali metal salt of an organic acid is introduced. Further, flow rates of the solutions are measured by flowmeters 113 and 114, and controlled. The solutions introduced into the sealed mixing means 118 are mixed in the sealed mixing means and fed to the tank 120 for formed dispersion via a heat exchanger 119. A part of the dispersion in the tank 120 for formed dispersion is fed to the sealed mixing means 118 again by a circulation pump 117.

The "sealed mixing means" used in the present specification refers to means for stirring and mixing liquids in which a vessel is filled with liquids to be mixed and contains substantially no air phase and thus the liquids are stirred and mixed under a condition that the so-called gas/liquid interface does not exist. The sealed mixing means used in the present invention may be any such means, and examples thereof include, for example, rotary stirrers and emulsification dispersion machines such as those provided with paddles and propellers, dissolvers and rotary homogenizers, static type mixers such as reciprocal motion type stirrers, static type mixers such as static mixers and through other mixers, combinations thereof and so forth. The sealed mixing means may consist of one vessel or two or more vessels disposed in series or in parallel.

For the mixing of liquids, if stirring force is too small, sufficient mixing cannot be obtained. On the other hand, unduly large stirring force generates heat and causes cavitation. Therefore, a preferred range is defined for the stirring force. In sealed mixing means provided with a rotary impeller, linear velocity at the outermost periphery of the impeller is preferably 1–50 m/second, more preferably 1–30 m/second, and consumptive power for stirring per unit volume of liquid is preferably 0.1–10 kW/L, more preferably 0.5–5 kW/L. As means for suppressing the cavitation, dissolved air in the liquid can be reduced or the pressure can be elevated by about 0.1–2 $kgf/cm^2$ with respect to the atmospheric pressure.

Although the material of the sealed mixing means is not particularly limited so long as it has a suitable mechanical strength, it is preferably a material inert against the silver ion-containing solution, organic acid silver salt solution and organic solvents to be used. Further, since the organic acid alkali metal solution is usually at a high temperature of 50° C. or more, it is also necessary to select a thermally stable material. Examples of materials satisfying these requirements include stainless steel (SUS304, SUS316 etc.), titanium or titanium alloys, metal materials coated with glass lining, ceramics, fluorocarbon resin or the like, composites resins comprising glass fibers, Kevlar or the like, engineering plastics such as polyacetal and modified polyphenylene oxide and so forth.

The sealed mixing means constituting the apparatuses of the present invention may consist of one of the means as in the apparatuses shown in FIGS. 1–4, or two or more of the means may be disposed in parallel. When two or more of the means are disposed in parallel, the solutions may be supplied to each means in an equal amount. As an example of apparatus utilizing two of sealed mixing means, the apparatus shown in FIG. 5 can be exemplified.

Figure 5:
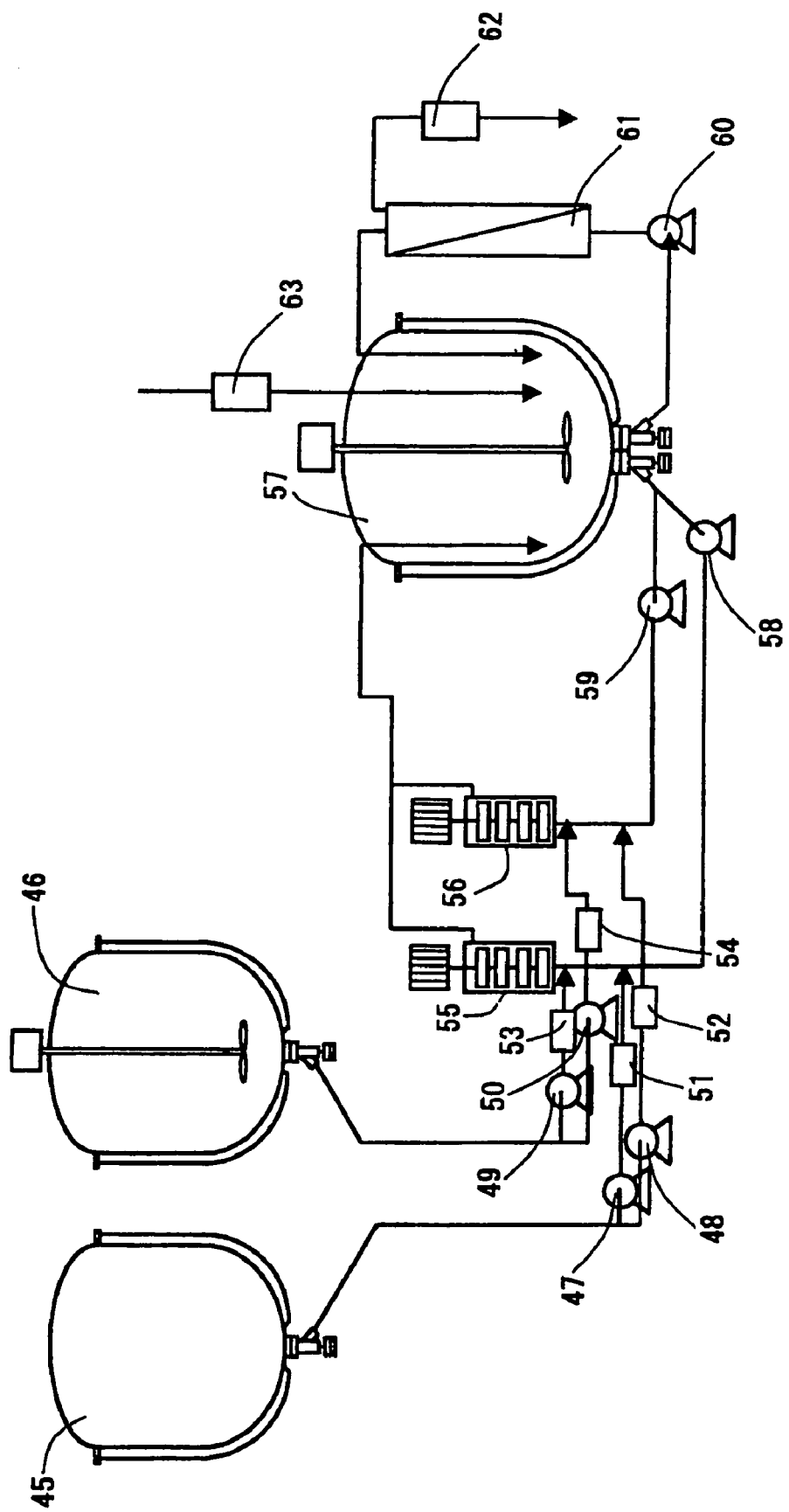
FIG. 5 is a schematic view showing a further exemplary structure of an apparatus used for the preparation of organic acid silver salt grains according to the present invention.

In FIG. 5, a solution containing silver ions is put into a tank 45 for Additive component 1, and a solution containing an alkali metal salt of an organic acid is put into a tank 46 for Additive component 2. The solutions were fed into sealed mixing means 55 and 56 by pumps 47, 48, 49 and 50, respectively. Flow rates of the solutions were measured by flowmeters 51, 52, 53 and 54, respectively, and controlled. The solutions introduced into the sealed mixing means 55 and 56 are mixed in the sealed mixing means and fed to the tank 57 for formed dispersion. A part of the dispersion in the tank 57 for formed dispersion is fed to the sealed mixing means 55 and 56 again by circulation pumps 58 and 59. Further, apart of the dispersion in the tank 57 for formed dispersion is introduced into an ultrafiltration module 61 by a pump 60 for circulation in ultrafiltration process and subjected to an ultrafiltration process. At this time, permeated water is measured by a flowmeter 62, and the dispersion that underwent the ultrafiltration is returned to the tank 57 for formed dispersion. Further, pure wafer is supplemented to the tank 57 for formed dispersion, and its flow rate is measured by a flowmeters 63.

In the apparatuses of the present invention, in order to rapidly lower the temperature of the liquid after the reaction of the solution containing silver ions and the solution containing an alkali metal salt of an organic acid, the solution containing silver ions and the solution containing an alkali metal salt of an organic acid supplied to the sealed mixing means may be cooled beforehand. Further, a heat exchanger may be provided on the sealed mixing means itself, between the sealed mixing means and the tanks, or before the sealed mixing means. The heat exchanger used for cooling is not particularly limited. For example, there can be used a multi-pipe cylinder type heat exchanger, heat pipe type heat exchanger, double pipe type heat exchanger, coiled type heat exchanger, cascade type heat exchanger, plate type heat exchanger, spiral plate type heat exchanger, water-cooled heat exchanger and so forth.

As the flowmeter for the solution containing silver ions, an electromagnetic flowmeter or mass flowmeter showing a measurement error of less than 1% and time coefficient of less than 1 second can be used. As the flowmeter for the solution containing an alkali metal salt of an organic acid, a mass flowmeter showing a measurement error of less than 1% and time coefficient of less than 1 second can be used.

Examples of the pump include pumps in which feedback control is possible based on a measured value obtained by the flowmeter (e.g., rotary pump, sanitary pump, gear pump, mono pump, plunger pump, diaphragm pump etc), pumps providing stable discharge with a quantification error of less than 1% (e.g., gear pump, mono pump, plunger pump, diaphragm pump etc.) and so forth. Those showing a pulsation ratio of less than 5% are preferred.

Hereafter, a thermally processed image recording material in which the organic acid silver salt prepared by the preparation methods of the present invention can be used will be explained.

The thermally processed image recording material preferably has an image-recording layer comprising the aforementioned silver salt of an organic acid as a reducible silver salt and a reducing agent for silver ions in a matrix of a binder. To obtain photosensitivity, a catalytically active amount of photocatalyst (preferably, a photosensitive silver halide) is further used. Further, a toning agent for controlling silver color tone is used as required. The image-recording layer is preferably formed by using a coating solution containing a photosensitive silver halide and a polymer showing an equilibrated moisture content of 2 weight % or less at 25° C. and relative humidity of 60% in the form of latex as the binder, and 30 weight % or more of water in the solvent of the coating solution.

The silver salt of an organic acid may be used in any desired amount. However, it is preferably used in an amount of 0.1–5 g/m$^2$, more preferably 1–3 g/m$^2$, in terms of silver amount.

The thermally processed image recording material utilizing the organic acid silver salt grains prepared by the methods of the present invention preferably contains a reducing agent for the organic acid silver salt. The reducing agent for the organic acid silver salt may be any substance (preferably, organic substance) capable of reducing silver ions into silver. Some examples of the reducing agent are described in JP-A-11-65021, paragraphs 0043 to 0045, EP 0803764A1, from page 7, line 34 to page 18, line 12, Japanese Patent Application Nos. 2000-16661, 2000-208 and 2000-2428.

Especially preferred are bisphenol-type reducing agents, and preferred examples thereof are mentioned below, but not limited to these.

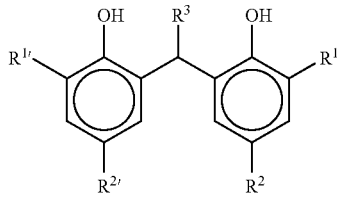

| | R$^1$ | R$^{1'}$ | R$^2$ | R$^{2'}$ | R$^3$ |
|---|---|---|---|---|---|
| I-1 | CH$_3$ | CH$_3$ | CH$_3$ | CH$_3$ | H |
| I-2 | CH$_3$ | CH$_3$ | CH$_3$ | CH$_3$ | CH$_3$ |
| I-3 | CH$_3$ | CH$_3$ | CH$_3$ | CH$_3$ | C$_3$H$_7$ |
| I-4 | CH$_3$ | CH$_3$ | CH$_3$ | CH$_3$ | i-C$_3$H$_7$ |
| I-5 | CH$_3$ | CH$_3$ | CH$_3$ | CH$_3$ | CH(C$_2$H$_5$)C$_4$H$_9$ |
| I-6 | CH$_3$ | CH$_3$ | CH$_3$ | CH$_3$ | CH$_2$CH(CH$_3$)CH$_2$C(CH$_3$)$_3$ |
| I-7 | CH$_3$ | CH$_3$ | C$_2$H$_5$ | C$_2$H$_5$ | H |
| I-8 | CH$_3$ | CH$_3$ | C$_2$H$_5$ | C$_2$H$_5$ | i-C$_3$H$_7$ |
| I-9 | C$_2$H$_5$ | C$_2$H$_5$ | CH$_3$ | CH$_3$ | H |
| I-10 | C$_2$H$_5$ | C$_2$H$_5$ | CH$_3$ | CH$_3$ | i-C$_3$H$_7$ |
| I-11 | t-C$_4$H$_9$ | t-C$_4$H$_9$ | CH$_3$ | CH$_3$ | H |
| I-12 | t-C$_4$H$_9$ | t-C$_4$H$_9$ | CH$_3$ | CH$_3$ | CH$_3$ |
| I-13 | t-C$_4$H$_9$ | t-C$_4$H$_9$ | CH$_3$ | CH$_3$ | C$_2$H$_5$ |
| I-14 | t-C$_4$H$_9$ | t-C$_4$H$_9$ | CH$_3$ | CH$_3$ | n-C$_3$H$_7$ |
| I-15 | t-C$_4$H$_9$ | t-C$_4$H$_9$ | CH$_3$ | CH$_3$ | n-C$_4$H$_9$ |
| I-16 | t-C$_4$H$_9$ | t-C$_4$H$_9$ | CH$_3$ | CH$_3$ | n-C$_7$H$_{15}$ |
| I-17 | t-C$_4$H$_9$ | t-C$_4$H$_9$ | CH$_3$ | CH$_3$ | n-C$_{11}$H$_{21}$ |
| I-18 | t-C$_4$H$_9$ | t-C$_4$H$_9$ | CH$_3$ | CH$_3$ | i-C$_3$H$_7$ |
| I-19 | t-C$_4$H$_9$ | t-C$_4$H$_9$ | CH$_3$ | CH$_3$ | CH(C$_2$H$_5$)C$_4$H$_9$ |
| I-20 | t-C$_4$H$_9$ | t-C$_4$H$_9$ | CH$_3$ | CH$_3$ | CH$_2$CH(CH$_3$)$_2$ |
| I-21 | t-C$_4$H$_9$ | t-C$_4$H$_9$ | CH$_3$ | CH$_3$ | CH$_2$CH(CH$_3$)CH$_2$C(CH$_3$)$_3$ |
| I-22 | t-C$_4$H$_9$ | t-C$_4$H$_9$ | CH$_3$ | CH$_3$ | CH$_2$OCH$_3$ |
| I-23 | t-C$_4$H$_9$ | t-C$_4$H$_9$ | CH$_3$ | CH$_3$ | CH$_2$CH$_2$OCH$_3$ |
| I-24 | t-C$_4$H$_9$ | t-C$_4$H$_9$ | CH$_3$ | CH$_3$ | CH$_2$CH$_2$OC$_4$H$_9$ |
| I-25 | t-C$_4$H$_9$ | t-C$_4$H$_9$ | CH$_3$ | CH$_3$ | CH$_2$CH$_2$SC$_{12}$H$_{25}$ |
| I-26 | t-C$_4$H$_9$ | t-C$_4$H$_9$ | C$_2$H$_5$ | C$_2$H$_5$ | H |
| I-27 | t-C$_4$H$_9$ | t-C$_4$H$_9$ | C$_2$H$_5$ | C$_2$H$_5$ | CH$_3$ |
| I-28 | t-C$_4$H$_9$ | t-C$_4$H$_9$ | C$_2$H$_5$ | C$_2$H$_5$ | n-C$_3$H$_7$ |
| I-29 | t-C$_4$H$_9$ | t-C$_4$H$_9$ | C$_2$H$_5$ | C$_2$H$_5$ | i-C$_3$H$_7$ |
| I-30 | t-C$_4$H$_9$ | t-C$_4$H$_9$ | C$_2$H$_5$ | C$_2$H$_5$ | CH$_2$CH$_2$OCH$_3$ |
| I-31 | t-C$_4$H$_9$ | t-C$_4$H$_9$ | n-C$_3$H$_7$ | n-C$_3$H$_7$ | H |
| I-32 | t-C$_4$H$_9$ | t-C$_4$H$_9$ | n-C$_3$H$_7$ | n-C$_3$H$_7$ | CH$_3$ |
| I-33 | t-C$_4$H$_9$ | t-C$_4$H$_9$ | n-C$_3$H$_7$ | n-C$_3$H$_7$ | n-C$_3$H$_7$ |
| I-34 | t-C$_4$H$_9$ | t-C$_4$H$_9$ | n-C$_4$H$_9$ | n-C$_4$H$_9$ | H |
| I-35 | t-C$_4$H$_9$ | t-C$_4$H$_9$ | n-C$_4$H$_9$ | n-C$_4$H$_9$ | CH$_3$ |
| I-36 | t-C$_5$H$_{11}$ | t-C$_5$H$_{11}$ | CH$_3$ | CH$_3$ | H |
| I-37 | t-C$_5$H$_{11}$ | t-C$_5$H$_{11}$ | CH$_3$ | CH$_3$ | CH$_3$ |
| I-38 | t-C$_5$H$_{11}$ | t-C$_5$H$_{11}$ | C$_2$H$_5$ | C$_2$H$_5$ | H |
| I-39 | t-C$_5$H$_{11}$ | t-C$_5$H$_{11}$ | C$_2$H$_5$ | C$_2$H$_5$ | CH$_3$ |
| I-40 | i-C$_3$H$_7$ | i-C$_3$H$_7$ | CH$_3$ | CH$_3$ | H |
| I-41 | i-C$_3$H$_7$ | i-C$_3$H$_7$ | CH$_3$ | CH$_3$ | n-C$_3$H$_7$ |
| I-42 | i-C$_3$H$_7$ | i-C$_3$H$_7$ | C$_2$H$_5$ | C$_2$H$_5$ | H |
| I-43 | i-C$_3$H$_7$ | i-C$_3$H$_7$ | C$_2$H$_5$ | C$_2$H$_5$ | n-C$_3$H$_7$ |
| I-44 | i-C$_3$H$_7$ | i-C$_3$H$_7$ | i-C$_3$H$_7$ | i-C$_3$H$_7$ | H |
| I-45 | i-C$_3$H$_7$ | i-C$_3$H$_7$ | i-C$_3$H$_7$ | i-C$_3$H$_7$ | CH$_3$ |
| I-46 | t-C$_4$H$_9$ | CH$_3$ | CH$_3$ | CH$_3$ | H |
| I-47 | t-C$_4$H$_9$ | CH$_3$ | CH$_3$ | CH$_3$ | CH$_3$ |
| I-48 | t-C$_4$H$_9$ | CH$_3$ | CH$_3$ | CH$_3$ | n-C$_3$H$_7$ |
| I-49 | t-C$_4$H$_9$ | CH$_3$ | t-C$_4$H$_9$ | CH$_3$ | CH$_3$ |
| I-50 | i-C$_3$H$_7$ | CH$_3$ | CH$_3$ | CH$_3$ | CH$_3$ |

I-51

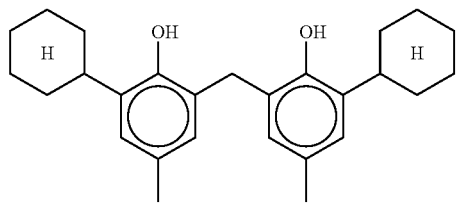

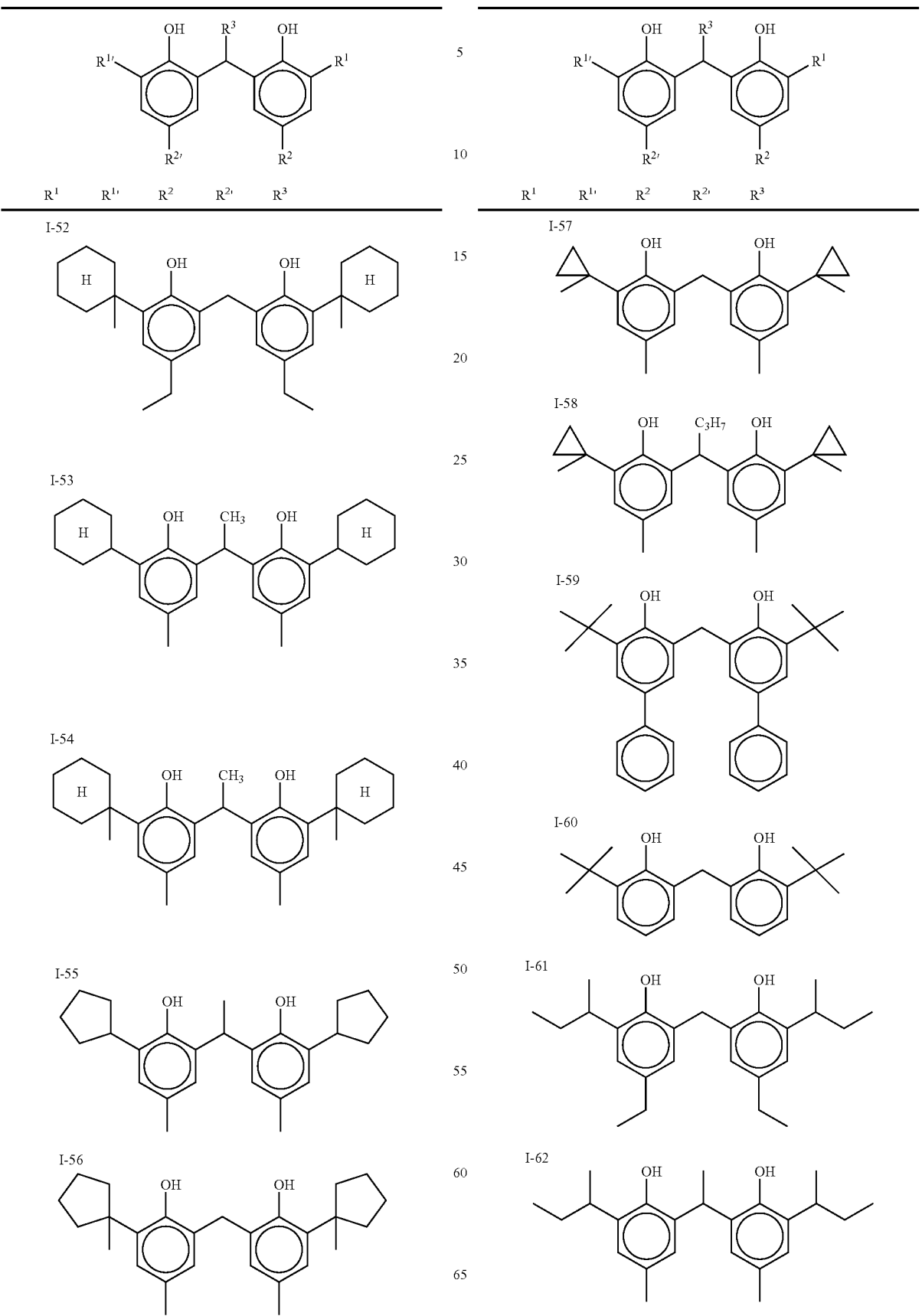

-continued
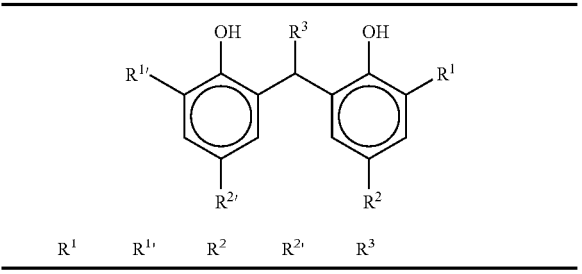
| R¹ | R¹' | R² | R²' | R³ |
I-63
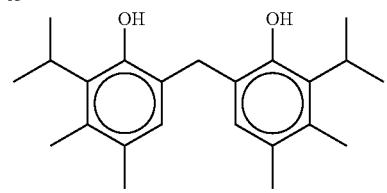
I-64
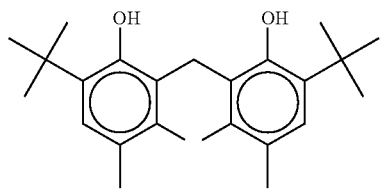
I-65
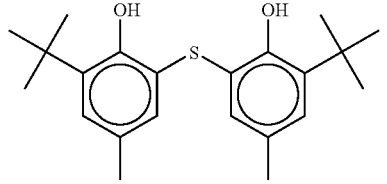
I-66
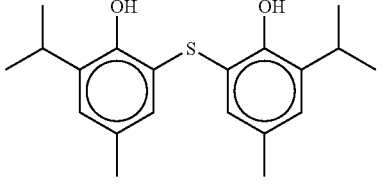
I-67
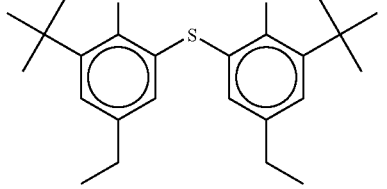
I-68
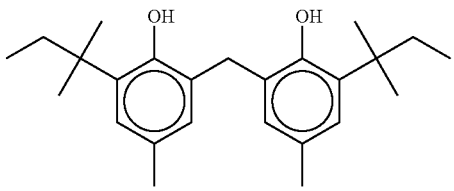
-continued
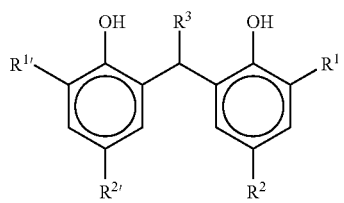
| R¹ | R¹' | R² | R²' | R³ |
I-69
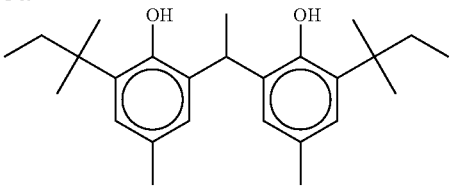
I-70
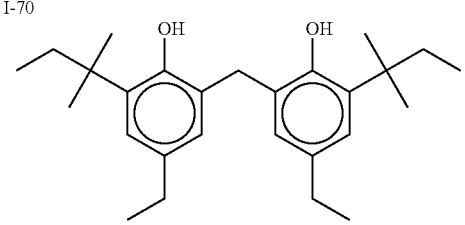
I-71
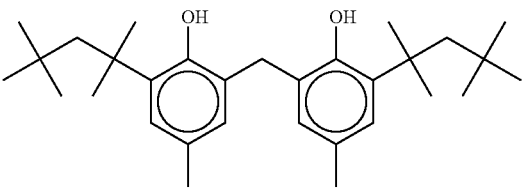
I-72
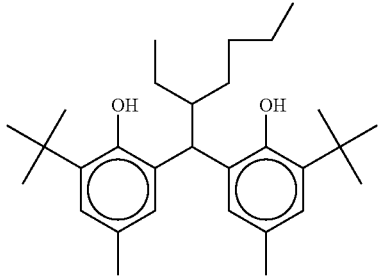
I-73
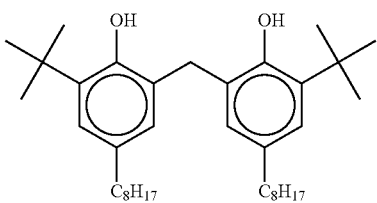

-continued

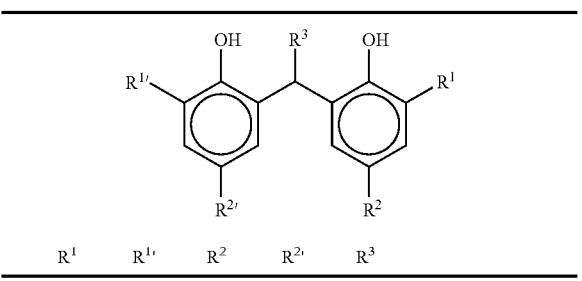

| R¹ | R¹' | R² | R²' | R³ |
|---|---|---|---|---|

I-74

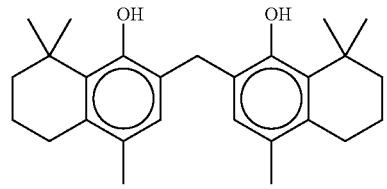

I-75

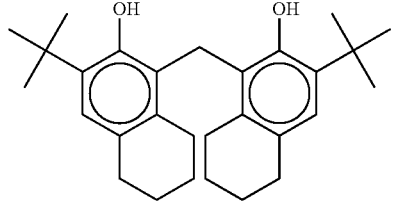

I-76

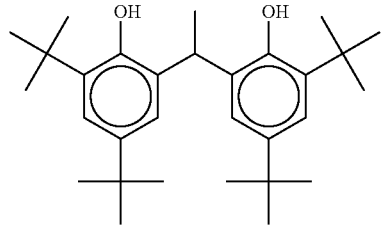

77

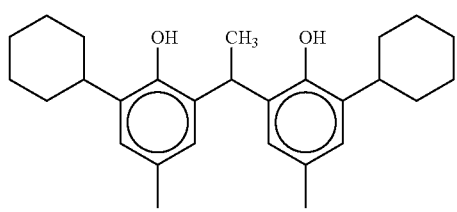

78

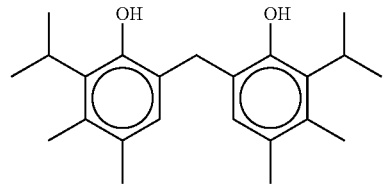

-continued

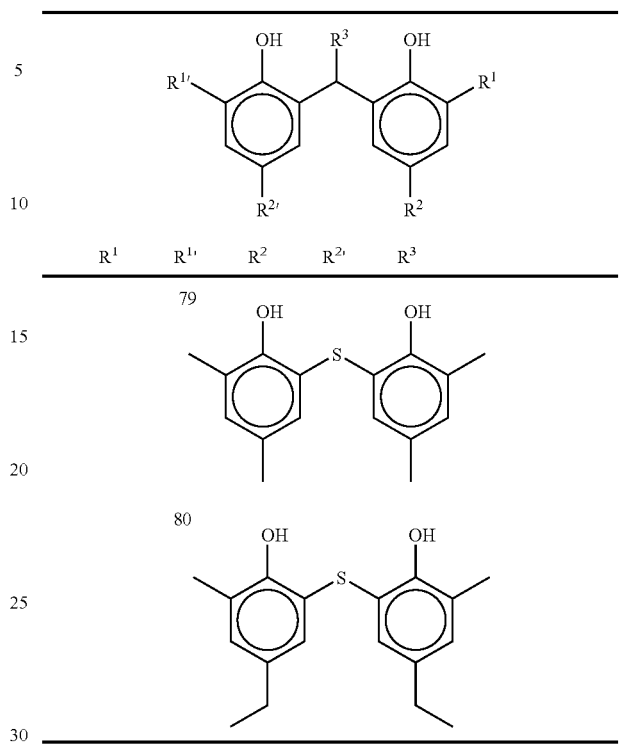

| R¹ | R¹' | R² | R²' | R³ |
|---|---|---|---|---|

79

80

The amount of the reducing agent is preferably 0.01–5.0 g/m², more preferably 0.1–3.0 g/m². The amount of the reducing agent is preferably 5–50 mole %, more preferably 10–40 mole %, per mole of silver on the image-forming layer side. The reducing agent is preferably contained in the image-forming layer.

The reducing agent may be added to a coating solution in any form such as solution, emulsion dispersion and solid microparticle dispersion, so as to be contained in the thermally processed image recording material.

As a well known emulsion dispersion method, there can be mentioned a method for mechanically preparing an emulsion dispersion by using an oil such as dibutyl phthalate, tricresyl phosphate, glyceryl triacetate or diethyl phthalate, ethyl acetate or cyclohexanone as an auxiliary solvent for dissolution.

Further, as a method for solid microparticle dispersion, there can be mentioned a method for preparing solid microparticle dispersion by dispersing powder of the reducing agent in a suitable solvent such as water using a ball mill, colloid mill, vibration ball mill, sand mill, jet mill and roller mill, or by means of ultrasonic wave. In this operation, protective colloid (e.g., polyvinyl alcohol), surfactant (e.g., anionic surfactants such as sodium triisopropylnaphthalenesulfonate (mixture of those having three isopropyl groups on different positions)) and so forth may be used. An aqueous dispersion may contain a preservative (e.g., benzisothiazolinone sodium salt).

In the thermally processed image recording material, the phenol derivatives represented by the formula (A) mentioned in Japanese Patent Application No. 11-73951 are preferably used as a development accelerator.

When the reducing agent has an aromatic hydroxyl group (—OH), in particular when the reducing agent is any of the aforementioned bisphenols, it is preferable to use together a non-reducing compound having a group that can form a hydrogen bond with the aromatic hydroxyl group. Examples of the group that can form a hydrogen bond with hydroxyl group or amino group include phosphoryl group, sulfoxido group, sulfonyl group, carbonyl group, amido group, an ester group, urethane group, ureido group, a tertiary amino group, a nitrogen-containing aromatic group and so forth. Particularly preferred examples of such a compound are those compounds having phosphoryl group, sulfoxido group, amido group (provided that it does not have >N—H group, but it is blocked like >N—R (R is a substituent other than H)), urethane group (provided that it does not have >N—H group, but it is blocked like >N—R (R is a substituent other than H)), or ureido group (provided that it does not have >N—H group, but it is blocked like >N—R (R is a substituent other than H)).

Particularly preferred hydrogen bond-forming compounds are compounds represented by the following formula (II).

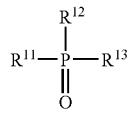

In the formula (II), $R^{12}$, $R^{12}$ and $R^{13}$ each independently represent an alkyl group, an aryl group, an alkoxy group, an aryloxy group, an amino group or a heterocyclic group, and these groups may or may not have one or more substituents. Two of $R^{11}$, $R^{12}$ and $R^{13}$ may be bonded together to form a ring.

When $R^{11}$, $R^{12}$ and $R^{13}$ have one or more substituents, they can be selected from a halogen atom, an alkyl group, an aryl group, an alkoxy group, an amino group, an acyl group, anacylamino group, an alkylthio group, an arylthio group, a sulfonamide group, an acyloxy group, an oxycarbonyl group, a carbamoyl group, a sulfamoyl group, a sulfonyl group, a phosphoryl group and so forth, and they are preferably selected from an alkyl group and an aryl group. Specific examples thereof are methyl group, ethyl group, isopropyl group, t-butyl group, t-octyl group, phenyl group, 4-alkoxyphenyl group, 4-acyloxyphenyl group and so forth.

Specific examples of the groups represented by $R^{13}$, $R^{12}$ and $R^{13}$ include a substituted or unsubstituted alkyl group such as methyl group, ethyl group, butyl group, octyl group, dodecyl group, isopropyl group, t-butyl group, t-amyl group, t-octyl group, cyclohexyl group, 1-methylcyclohexyl group, benzyl group, phenethyl group and 2-phenoxypropyl group; a substituted or unsubstituted aryl group such as phenyl group, cresyl group, xylyl group, naphthyl group, 4-t-butylphenyl group, 4-t-octylphenyl group, 4-anisidyl group and 3,5-dichlorophenyl group; a substituted or unsubstituted alkoxyl group such as methoxy group, ethoxy group, butoxy group, octyloxy group, 2-ethylhexyloxy group, 3,5,5-trimethylhexyloxy group, dodecyloxy group, cyclohexyloxy group, 4-methylcyclohexyloxy group and benzyloxy group; a substituted or unsubstituted aryloxy group such as phenoxy group, cresyloxy group, isopropylphenoxy group, 4-t-butylphenoxy group, naphthoxy group and biphenyloxy group; a substituted or unsubstituted amino group such as amino group, dimethylamino group, diethylamino group, dibutylamino group, dioctylamino group, N-methyl-N-hexylamino group, dicyclohexylamino group, diphenylamino group and N-methyl-N-phenylamino group; a heterocyclic group such as 2-pyridyl group, 4-pyridyl group, 2-furanyl group, 4-piperidinyl group, 8-quinolyl group and 5-quinolyl group, and so forth.

$R^{11}$, $R^{12}$ and $R^{13}$ are preferably selected from an alkyl group, an aryl group, an alkoxy group and an aryloxy group. It is preferred that one or more of $R^{11}$, $R^{12}$ and $R^{13}$ should be selected from an alkyl group and an aryl group, and it is more preferred that two or more of $R^{11}$, $R^{12}$ and $R^{13}$ should be selected from an alkyl group and an aryl group. In view of availability at low cost, it is preferred that $R^{11}$, $R^{12}$ and $R^{13}$ should be the same groups.

Specific examples of the compound represented by the formula (II) will be shown below. However, the compounds that can be used for the present invention are not limited to these examples.

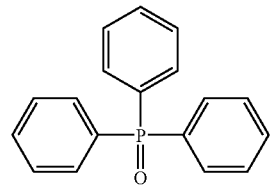
(II-1)

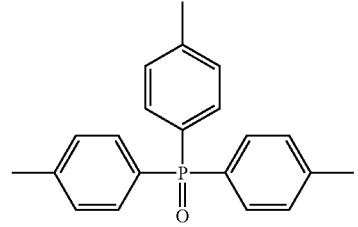
(II-2)

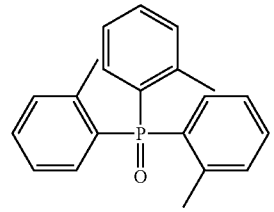
(II-3)

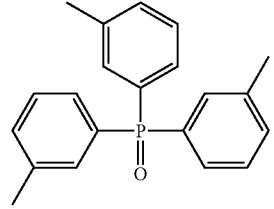
(II-4)

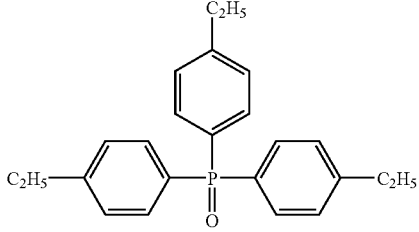
(II-5)

-continued
(II-6)
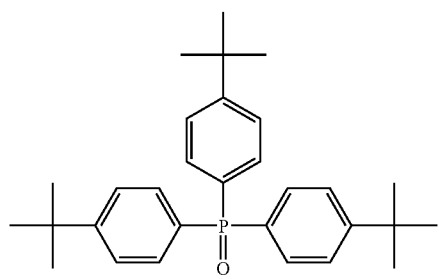
(II-7)
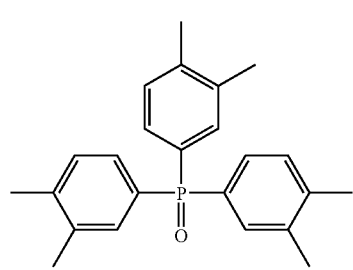
(II-8)
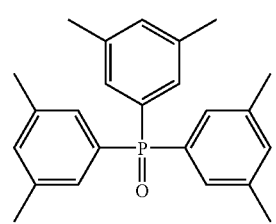
(II-9)
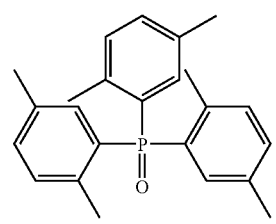
(II-10)
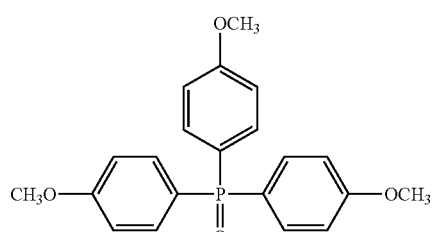
(II-11)
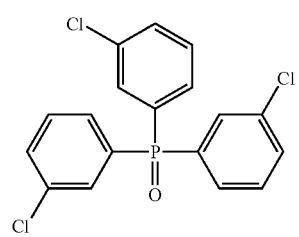
-continued
(II-12)
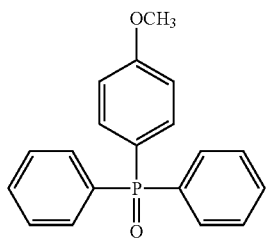
(II-13)
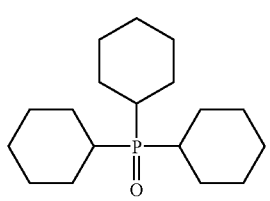
(II-14)
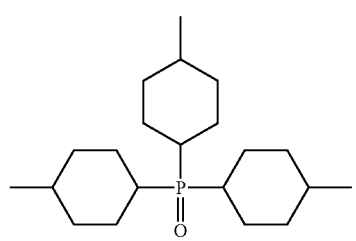
(II-15)
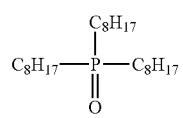
(II-16)
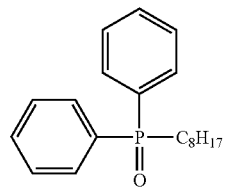
(II-17)
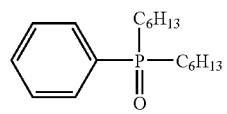
(II-18)
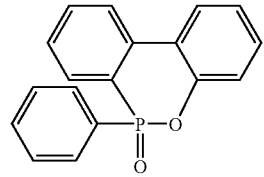
(II-19)
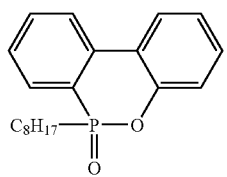

-continued
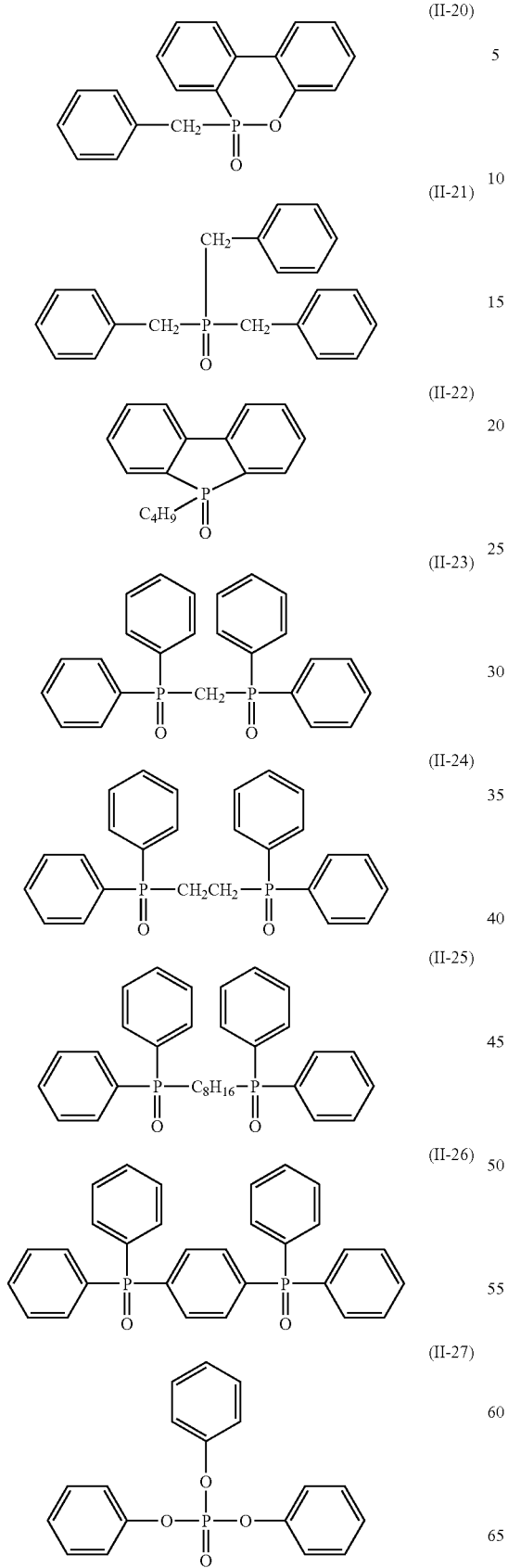
(II-20)
(II-21)
(II-22)
(II-23)
(II-24)
(II-25)
(II-26)
(II-27)
-continued
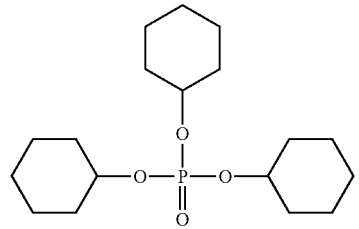
(II-28)
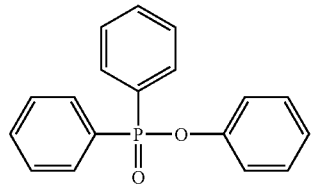
(II-29)
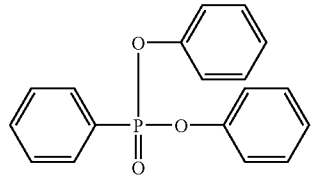
(II-30)
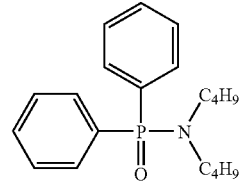
(II-31)
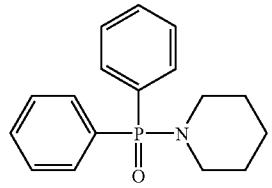
(II-32)
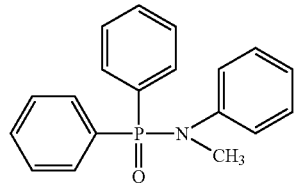
(II-33)
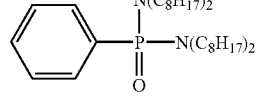
(II-34)
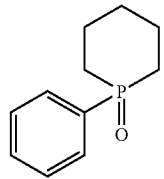
(II-35)

-continued (II-36)

(II-37)

(II-38)

(II-39)

(II-40)

The compound represented by the formula (II) may be added to a coating solution, like the reducing agent, in the form of solution, emulsion dispersion or solid microparticle dispersion for use in the thermally processed image recording material. The compound represented by the formula (II) forms a complex in a solution with a compound having a phenolic hydroxyl group or amino group through hydrogen bond, and hence it can be isolated as crystals of such a complex depending on the combination of the reducing agent and the compound represented by the formula (II). Crystal powder isolated in such a manner is particularly preferably used as solid microparticle dispersion in order to obtain stable performance. Further, it is also preferable to mix the reducing agent and the compound represented by the formula (II) as powders and allow them to form a complex during dispersion operation using a suitable dispersing agent in a sand grinder mill or the like.

The compound represented by the formula (II) is preferably used in an amount of 1–200 mole %, more preferably 10–150 mole %, further preferably 30–100 mole %, with respect to the reducing agent.

The photosensitive silver halide that can be used for the present invention is not particularly limited as for the halogen composition, and silver chloride, silver chlorobromide, silver bromide, silver iodobromide, and silver chloroiodobromide may be used. The halide composition may have a uniform distribution in the grains, or the compositions may change stepwise or continuously in the grains. Silver halide grains having a core/shell structure may be preferably used. Core/shell grains having preferably a double to quintuple structure, more preferably a double to quadruple structure may be used. A technique for localizing silver bromide on the surface of silver chloride or silver chlorobromide grains may also be preferably used.

Methods for the preparation of the photosensitive silver halide are well known in the art, and there can be used, for example, the methods described in Research Disclosure, No. 17029 (June, 1978) and U.S. Pat. No. 3,700,458. More specifically, a method can be used which comprises preparing photosensitive silver halide grains by addition of a silver-supplying compound and a halogen-supplying compound to a solution of gelatin or other polymer, and then mixing the resulting grains with a silver salt of an organic acid. The methods disclosed in JP-A-119374, paragraphs 0217 to 0224, Japanese Patent Application Nos. 11-98708 and 11-84182 are also preferred.

As for a grain size of the photosensitive silver halide, smaller grains are desirable to prevent cloudiness after image formation. Specifically, the grain size may preferably be not greater than 0.20 μm, more preferably 0.01–0.15 μm, further preferably 0.02–0.12 μm. The term "grain size" used here in means a diameter of a projected area of sphere having the same volume as the grain (where silver halide grains are tabular grains, the term means the diameter of a circle having the same area as a projected area of the main surface of the tabular grain).

Examples of the form of silver halide grains include a cubic form, octahedral form, tabular form, spherical for m, rod-like form and potato-like form. In particular, cubic grains are preferred. Silver halide grains having round corners are also preferably used. Surface index (Miller index) of outer surfaces of the photosensitive silver halide grains is not particularly limited. However, it is desirable that the [100] face should be present in a high proportion that can achieve high spectral sensitizing efficiency when a spectral sensitizing dye adsorbs on the grains. The proportion of the [100] face may be preferably not lower than 50%, more preferably at least 65%, still more preferably at least 80%. The proportion of Miller index [100] face can be determined using the method described in T. Tani, J. Imaging Sci., 29, 165 (1985), which utilizes the difference in adsorption of a sensitizing dye to [111] face and [100] face.

Silver halide grains having hexacyano-metal complex on their outermost surfaces are preferably used. Specific examples of the hexacyano-metal complex include [Fe(CN)$_6$]$^{4-}$, [Fe(CN)$_6$]$^{3-}$, [Ru(CN)$_6$]$^{4-}$, [Os(CN)$_6$]$^{4-}$, [Co(CN)$_6$]$^{3-}$, [Rh(CN)$_6$]$^{3-}$, [Ir(CN)$_6$]$^{3-}$, [Cr(CN)$_6$]$^{3-}$, [Re(CN)$_6$]$^{3-}$ and so forth. In the present invention, hexacyano-Fe complexes are preferred.

Since the hexacyano-metal complex exists in the form of an ion in an aqueous solution, its counter cation is not critical. However, it is preferable to use ions readily mixed with water and suitable for the precipitation operation of silver halide emulsions, for example, alkali metal ions such as sodium ion, potassium ion, rubidium ion, cesium ion and lithium ion, ammonium ions, alkylammonium ions (e.g., tetramethylammonium ions, tetraethylammonium ions, tetrapropylammonium ions, tetra-(n-butyl)ammonium ions) and so forth.

The hexacyano-metal complex may be added to silver halide grains in the form of a solution in water or in a mixed solvent of water and an organic solvent miscible with water (for example, alcohols, ethers, glycols, ketones, esters, amides etc.), or in the form of a mixture thereof with gelatin.

The amount of the hexacyano-metal complex is preferably $1\times10^{-5}$ mole to $1\times10^{-2}$ mole, more preferably $1\times10^{-4}$ mole to $1\times10^{-3}$ mole, per mol of silver.

In order to make the hexacyano-metal complex exist on the outermost surfaces of silver halide grains, the hexacyano-metal complex is directly added before completion of the grain formation process, i.e., after the addition of an aqueous silver nitrate solution used for the formation of silver halide grains and before chemical sensitization process where chalcogen sensitization with sulfur, selenium or tellurium or noble metal sensitization with gold or the like is performed, during washing with water or dispersion operation or immediately before the chemical sensitization. To prevent growth of the silver halide grains, it is desirable that the hexacyano-metal complex is added to the grains immediately after the grains are formed, and the complex is added before the grain formation process is finished.

The addition of the hexacyano-metal complex may be started after 96 weight % of the total of silver nitrate for grain formation has been added. More preferably, it is added after 98 weight of silver nitrate, particularly preferably after 99 weight % of silver nitrate has been added.

If the hexacyano-metal complex is added after addition of aqueous solution of silver nitrate in which the formation of silver halide grains is almost completed, the hexacyano-metal complex can be adsorbed onto the outermost surfaces of the silver halide grains, and most of the complex forms a hardly-soluble salt with silver ions existing on the surfaces of the grains. Such a silver salt of hexacyano-iron (II) is a salt more hardly soluble than AgI, and therefore fine grains formed are prevented from being dissolved again. Thus, it becomes possible to produce fine silver halide grains having a small grain size.

The photosensitive silver halide grains may contain a metal of Group VIII to Group X in the periodic table of elements (including Group I to Group XVIII) or metal complex thereof. The metal of Group VIII to X of the periodic table or the center metal of the metal complex is preferably rhodium, ruthenium or iridium. The metal complex may be used alone, or two or more complexes of the same or different metals may also be used in combination. The metal complex content is preferably from $1\times10^{-9}$ to $1\times10^{-3}$ mole per mole of silver. Such heavy metals and metal complexes as well as addition method therefor are described in JP-A-7-225449, JP-A-11-65021, paragraphs 0018 to 0024, and JP-A-11-119374, paragraphs 0227 to 0240.

Further, metal complexes that can be contained in the silver halide grains used for the present invention (e.g., $[Fe(CN)_6]^{4-}$), desalting methods and chemical sensitization methods are described in JP-A-11-84574, paragraphs 0046 to 0050, JP-A-11-65021, paragraphs 0025 to 0031, and JP-A-11-119374, paragraphs 0242 to 0250.

As gelatin contained in the photosensitive silver halide emulsion, various kinds of gelatin may be used. In order to obtain good dispersion state of the photosensitive silver halide emulsion in a coating solution containing a silver salt of an organic acid, low molecular weight gelatin having a molecular weight of 500–60,000 is preferably used. While such low molecular weight gelatin may be used during the grain formation or the dispersion operation after the desalting treatment, it is preferably used during the dispersion operation after the desalting treatment.

As a sensitizing dye that can be used for the present invention, there can be advantageously selected those sensitizing dyes which can spectrally sensitize silver halide grains within a desired wavelength range after they are adsorbed by the silver halide grains and have spectral sensitivity suitable for spectral characteristics of the light source to be used for exposure. Such sensitizing dyes and addition methods therefor are described in JP-A-11-65021, paragraphs 0103 to 0109, JP-A-10-18657 as for the compounds represented by the formula (II), JP-A-11-119347 as for the dyes represented by the formula (I) and paragraph 0106, U.S. Pat. Nos. 5,510,236, 3,871,887 as for the dyes disclosed in Example 5, JP-A-2-96131, JP-A-59-48753 as for the dyes disclosed therein and EP 0803764A1, page 19, line 38 to page 20, line 35, Japanese Patent Application Nos. 2000-86865, 2000-102560 and so forth. These dyes may be used each alone or in any combination of two or more of them. The sensitizing dye is added to the silver halide emulsion preferably during the period after the desalting step and before the coating step, more preferably during the period after the desalting step and before the start of the chemical ripening.

While the amount of the sensitizing dye used in the present invention may be selected to be a desired amount depending on the performance including sensitivity and fog, it is preferably $10^{-6}$ to 1 mole, more preferably $10^{-4}$ to $10^{-1}$ mole, per mole of silver halide in the image-forming layer.

A supersensitizer can be used for the thermally processed image recording material in order to improve spectral sensitization efficiency. Examples of the supersensitizer include the compounds disclosed in EP587338A, U.S. Pat. Nos. 3,877,943, 4,873,184, JP-A-5-341432, JP-A-11-109547, JP-A-10-111543 and so forth.

Photosensitive silver halide grains are preferably subjected to chemical sensitization by sulfur sensitization, selenium sensitization or tellurium sensitization. Any known compounds can be preferably used for such sulfur, selenium or tellurium sensitization, and for example, the compounds described in JP-A-7-128768 and so forth are usable for that purpose. Tellurium sensitization is particularly preferred, and the compounds described in JP-A-11-65021, paragraph 0030 and the compounds of formulas (II), (III) and (IV) given in JP-A-5-313284 are more preferred.

The chemical sensitization may be performed at any time so long as it is performed after the formation of the grains and before the coating. It may be performed after desalting and (1) before the spectral sensitization, (2) simultaneously with the spectral sensitization, (3) after the spectral sensitization, (4) immediately before the coating, or the like. It is particularly preferably performed after spectral sensitization.

The amount of the sulfur, selenium or tellurium sensitizer varies depending on the type of the silver halide grains to be used, the condition for chemical ripening etc., but may fall generally between $10^{-8}$ and $10^{-2}$ mole, preferably between $10^{-7}$ and $10^{-3}$ mole or so, per mol of the silver halide. Although the conditions for the chemical sensitization are not particularly limited, in general, pH is in the range of 5–8, the pAg in the range of 6–11, and the temperature in the range of 40–95° C.

The silver halide emulsion may be added with a thiosulfonic acid compound according to the method disclosed in EP293917A.

In the thermally processed image recording material, one kind of photosensitive silver halide emulsion may be used or two or more different emulsions (for example, those having different average grain sizes, different halogen compositions, different crystal habits or different chemical sensitization conditions) may be used in combination. By using plural photo sensitive silver halides having different sensitivities, contrast can be controlled. Examples of the techniques concerning this respect include those mentioned in JP-A-57-119341, JP-A-53-106125, JP-A-47-3929, JP-A-48-55730, JP-A-46-5187, JP-A-50-73627, JP-A-57-150841 and so forth. Each emulsion preferably has sensitivity difference of 0.2 log E or higher for other emulsions.

The amount of the photosensitive silver halide is preferably 0.03–0.6 g/m², more preferably 0.05–0.4 g/m², most preferably 0.1–0.4 g/m², as the amount of coated silver per 1 m² of the thermally processed image recording material. The amount of the photosensitive silver halide per mole of the silver salt of an organic acid is preferably from 0.01–0.5 mole, more preferably from 0.02–0.3 mole.

Methods and conditions for mixing photosensitive silver halide and a silver salt of an organic acid, which are separately prepared, are not particularly limited so long as the effect of the present invention can be attained satisfactorily. Examples thereof include, for example, a method of mixing silver halide grains and a silver salt of an organic acid after completion of respective preparations by using a high-speed stirring machine, ball mill, sand mill, colloid mill, vibrating mill, homogenizer or the like, or a method of preparing a silver salt of an organic acid by mixing a photosensitive silver halide obtained separately at any time during the preparation of the silver salt of an organic acid. For the mixing of them, mixing two or more kinds of aqueous dispersions of the silver salt of an organic acid and two or more kinds of aqueous dispersions of the photosensitive silver salt is preferably used for controlling photographic properties.

Preferred addition time point for the silver halide into the coating solution for image-forming layer resides in a period of from 180 minutes before the coating to immediately before the coating, preferably 60 minutes to 10 seconds before the coating. However, the method and conditions for mixing are not particularly limited. Specific examples of the mixing method include a method in which the mixing is performed in a tank designed so that a desired average residence time therein can be obtained, which residence time is calculated from addition flow rate and feeding amount to a coater, a method utilizing a static mixer described in N. Harnby, M. F. Edwards, A. W. Nienow, "Ekitai Kongo Gijutsu (Techniques for Mixing Liquids)", translated by Koji Takahashi, Chapter 8, Nikkan Kogyo Shinbunsha, 1989 and so forth.

The binder of the layer containing the silver salt of an organic acid may be any polymer. Preferred binders are those that are transparent or translucent, and generally colorless. The binder may consist of, for example, a naturally occurring resin, polymer or copolymer, synthetic resin, polymer or copolymer or other media that can form a film, such as gelatins, rubbers, poly(vinyl alcohols), hydroxyethyl celluloses, cellulose acetates, cellulose acetate butyrates, poly(vinylpyrrolidones), casein, starch, poly(acrylic acids), poly(methyl methacrylates), poly(vinyl chlorides), poly (methacrylic acids), styrene/maleic anhydride copolymers, styrene/acrylonitrile copolymers, styrene/butadiene copolymers, poly(vinyl acetals) (e.g., poly(vinyl formal), poly (vinyl butyral)), poly(esters), poly(urethanes), phenoxy resin, poly(vinylidene chlorides), poly(epoxides), poly(carbonates), poly(vinyl acetates), poly(olefins), cellulose esters and poly(amides). The binder may be formed from water, organic solvent or emulsion by coating it.

If the layer containing the silver salt of an organic acid is formed by using an aqueous coating solution containing 30 weight % or more of water based on a total solvent, further, if the binder of the layer containing the silver salt of an organic acid is soluble or dispersible in an aqueous solvent (water solvent), in particular, if a coating solution containing a polymer latex having an equilibrated moisture content of 2 weight % or less at 25° C. and relative humidity of 60% is used, the performance is improved. In the most preferred embodiment, the polymer latex is prepared to have an ion conductivity of 2.5 mS/cm or less. An example of a method for preparing such polymer latex includes a method comprising synthesizing a polymer and then purifying the polymer by using a functional membrane for separation.

The aqueous solvent in which the polymer binder is soluble or dispersible is water or water mixed with 70 weight % or less of a water-miscible organic solvent. Examples of the water-miscible organic solvent include, for example, alcohols such as methyl alcohol, ethyl alcohol and propyl alcohol; cellosolves such as methyl cellosolve, ethyl cellosolve and butyl cellosolve; ethyl acetate, dimethylformamide and so forth.

The term "aqueous solvent" used herein also encompasses systems in which a polymer is not thermodynamically dissolved but is present in a so-called dispersed state.

The definition "equilibrated moisture content at 25° C. and relative humidity of 60%" used herein can be represented by the following equation, in which $W^1$ indicates the weight of a polymer at humidity-conditioned equilibrium in an atmosphere of 25° C. and relative humidity of 60%, and $W^0$ indicates the absolute dry weight of the polymer at 25° C.

Equilibrated moisture content at 25° C. and relative humidity of 60%=$[(W^1-W^0)/W^0]\times 100$ (Weight %)

As for details of the definition of moisture content and methods for measurement, for example, Lecture of Polymer Engineering, 14, Test Methods for Polymer Materials (Polymer Society of Japan, Chijin Shokan) can be referred to.

The equilibrated moisture content at 25° C. and relative humidity of 60% of the binder polymer is preferably 2 weight % or less, more preferably from 0.01–1.5 weight %, most preferably from 0.02–1 weight %.

In the present invention, polymers dispersible in aqueous solvents are particularly preferred. Examples of systems in the dispersed state include, for example, polymer latex in which fine solid particles of polymer are dispersed, and a system in which a polymer is dispersed in a molecular state or as micelles, both of which are preferred. Dispersed particles preferably have a mean particle size of around 1–50000 nm, more preferably around 5–1000 nm. Particle size distribution of the dispersed particles is not particularly limited, and either those having a broad particle size distribution or those having monodispersed particle size distribution may be used.

In preferred embodiments of the polymer dispersible in an aqueous solvent, hydrophobic polymers such as acrylic polymers, polyesters, rubbers (e.g., SBR resins), polyurethanes, polyvinyl chlorides, polyvinyl acetates, polyvinylidene chlorides, and polyolefins can preferably be used. The polymers may be linear, branched or crosslinked. They may be so-called homopolymers in which a single kind of monomer is polymerized, or copolymers in which two or more different kinds of monomers are polymerized. The copolymers may be random copolymers or block copolymers. The polymers may have a number average molecular weight of 5,000 to 1,000,000, preferably from 10,000 to 200,000. Polymers having a too small molecular weight fail to give sufficient mechanical strength of the image-forming layer (emulsion layer), and those having a too large molecular weight yield bad film forming property, and both of which are not preferred.

Specific examples of the preferred polymer latex are mentioned below. They are expressed with the constituent monomers. The numerals parenthesized indicate the contents in terms of weight %. The molecular weights are number average molecular weights.

P-1: Latex of -MMA(70)-EA(27)-MAA(3)-(molecular weight: 37000)
P-2: Latex of -MMA(70)-2EHA(20)-St(5)-AA(5)-(molecular weight: 40000)
P-3: Latex of -St(50)-Bu(47)-MMA(3)-(molecular weight: 45000)
P-4: Latex of -St(68)-Bu(29)-AA(3)-(molecular weight: 60000)
P-5: Latex of -St(71)-Bu(26)-AA(3)-(molecular weight: 60000)
P-6: Latex of -St(70)-Bu(27)-IA(3)-(molecular weight: 120000)
P-7: Latex of -St(75)-Bu(24)-AA(1)-(molecular weight: 108000)
P-8: Latex of -St(60)-Bu(35)-DVB(3)-MAA(2)-(molecular weight: 150000)
P-9: Latex of -St(70)-Bu(25)-DVB(2)-AA(3)-(molecular weight: 280000)
P-10: Latex of -VC(50)-MMA(20)-EA(20)-AN(5)-AA(5)-(molecular weight: 80000)
P-11: Latex of -VDC(85)-MMA(5)-EA(5)-MAA(5)-(molecular weight: 67000)
P-12: Latex of -Et(90)-MAA(10)-(molecular weight: 12000)
P-13: Latex of -St(70)-2EHA(27)-AA(3)-(molecular weight: 130000)
P-14: Latex of -MMA(63)-EA(35)-AA(2)-(molecular weight: 33000)

Abbreviations used for the constituent monomers are as follows:
MMA: methyl methacrylate
EA: ethyl acrylate
MAA: methacrylic acid
2EHA: 2-ethylhexyl acrylate
St: styrene
Bu: butadiene
AA: acrylic acid
DVB: divinylbenzene
VC: vinyl chloride
AN: acrylonitrile
VDC: vinylidene chloride
Et: ethylene
IA: itaconic acid The polymer latexes mentioned above are also commercially available, and those mentioned below can be used, for example. Examples of acrylic resins are CEBIAN A-4635, 46583, 4601 (all from Daicel Chemical Industries), Nipol Lx811, 814, 821, 820, 857 (all from Nippon Zeon) etc.; examples of polyester resins are FINETEX ES650, 611, 675, 850 (all from Dai-Nippon Ink & Chemicals), WD-size, WMS (both from Eastman Chemical) etc.; examples of polyurethane resins are HYDRAN AP10, 20, 30, 40(all from Dai-Nippon Ink & Chemicals) etc.; examples of rubber resins are LACSTAR 7310K, 3307B, 4700H, 7132C (all from Dai-Nippon Ink & Chemicals), Nipol Lx416, 410, 438C, 2507 (all from Nippon Zeon) etc.; examples of polyvinyl chloride resins are G351, G576 (both from Nippon Zeon) etc.; examples of polyvinylidene chloride resins are L502, L513 (both from Asahi Chemical Industry) etc.; examples of polyolefin resins are CHEMIPEARL S120, SA100 (both from Mitsui Petrochemical) etc.

These polymer latexes may be used each alone, or two or more kinds of them may be blended as required.

As the polymer latex used in the present invention, styrene/butadiene copolymer latex is particularly preferred. In the styrene/butadiene copolymer, the weight ratio of styrene monomer units and butadiene monomer units is preferably 40:60 to 95:5. The ratio of the styrene monomer units and the butadiene monomer units preferably account for from 60–99 weight % of the copolymer. The preferred range of the molecular weight of the copolymer is similar to that mentioned above.

Examples of styrene/butadiene copolymer latexes preferably used for the present invention include the aforementioned P-3 to P-8, commercially available products, LACSTAR-3307B, 7132C, Nipol Lx416 and so forth.

The latex used for the present invention preferably has a grass transition temperature (Tg) within the range of 10–80° C., more preferably in the range of 20–60° C. When a blend of two or more kinds of polymers having different glass transition temperatures is used, it is preferred that its weight average Tg should fall within the aforementioned range.

The layer containing silver salt of an organic acid of the thermally processed image recording material may optionally contain a hydrophilic polymer such as gelatin, polyvinyl alcohol, methyl cellulose, hydroxypropyl cellulose and carboxymethyl cellulose. The addition amount of the hydrophilic polymer is preferably 30 weight % or less, more preferably 20 weight % or less, of the total binder in the layer containing silver salt of an organic acid.

The layer containing silver salt of an organic acid (i.e., image-forming layer) is preferably formed by using polymer latex. The amount of the binder in the layer containing silver salt of an organic acid is such an amount that the weight ratio of total binder/silver salt of an organic acid should be 1/10 to 10/1, more preferably 1/5 to 4/1.

The layer containing silver salt of an organic acid usually also serves as an image-forming layer (photosensitive layer, emulsion layer) containing a photosensitive silver salt, that is, a photosensitive silver halide. In such a case, the weight ratio of total binder/silver halide is preferably 5–400, more preferably 10–200.

The total amount of the binder in the image-forming layer is preferably 0.2–30 g/m$^2$, more preferably 1–15 g/m$^2$. The image-forming layer may optionally contain a crosslinking agent for crosslinking, a surfactant for improving coating property and so forth.

The solvent for the coating solution for the layer containing silver salt of an organic acid of the thermally processed image recording material of the invention (for simplicity, solvents and dispersion media are collectively referred to as solvent) is an aqueous solvent containing at least 30 weight % of water. As for components other than water, any water-miscible organic solvents including, for example, methyl alcohol, ethyl alcohol, isopropyl alcohol, methyl cellosolve, ethyl cellosolve, dimethylformamide, ethyl acetate and so forth may be used. The water content of the solvent for the coating solution is preferably at least 50 weight %, more preferably at least 70 weight %. Preferred examples of the solvent composition are water, water/methyl alcohol=90/10, water/methyl alcohol=70/30, water/methyl alcohol/dimethylformamide=80/15/5, water/methyl alcohol/ethyl cellosolve=80/10/5, water/methyl alcohol/isopropyl alcohol=85/10/5 and so forth (numerals indicate weight %).

As antifoggants, stabilizers and stabilizer precursors that can be used for the present invention, there can be mentioned, for example, those mentioned in JP-A-10-62899, paragraph 0070 and EP0803764A1, from page 20, line 57 to page 21, line 7. Antifoggants preferably used for the present invention are organic halides. Examples thereof include, for example, those disclosed in JP-A-11-65021, paragraphs 0111 to 0112. Particularly preferred are the polyhalogenated compounds represented by the formula (P) mentioned in Japanese Patent Application No. 11-87297, the polyhalogenated compounds represented by the formula (II) mentioned in JP-A-10-339934, the polyhalogenated compounds described in Japanese Patent Application Nos. 11-90095, 11-89561, 11-205329 and 11-205330.

As the method for introducing an antifoggant into the thermally processed image recording material, the aforementioned method for introducing the reducing agent can be mentioned. The organic polyhaogenated compound is also preferably added in the form of a solid microparticle dispersion.

Other examples of the antifoggant include the mercury (II) salts described in JP-A-11-65021, paragraph 0113, the benzoic acids described in the same, paragraph 0114, the salicylic acid derivatives represented by the formula (Z) mentioned in Japanese Patent Application No. 11-87297, the formalin scavenger compounds represented by the formula (S) mentioned in Japanese Patent Application No. 11-23995, triazine compounds mentioned in JP-A-11-352624, Claim 9, compounds represented by the formula (III) mentioned in JP-A-6-11791, 4-hydroxy-6-methyl-1,3,3a,7-tetrazaindene and so forth.

The thermally processed image recording material may contain an azolium salt for prevention of fog. Examples of the azolium salt include, for example, the compounds of the formula (XI) disclosed in JP-A-59-193447, the compounds disclosed in JP-B-55-12581 and the compounds of the formula (II) disclosed in JP-A-60-153039. While the azolium salt may be added in any site of the thermally processed image recording material, it is preferably added in a layer on the side of an image-forming layer, more preferably in the layer containing silver salt of an organic acid. The azolium salt may be added at any time during the preparation of the coating solution. When the azolium salt is added to the layer containing silver salt of an organic acid, the azolium salt may be added at any time during the period of from the preparation of the silver salt of an organic acid to the preparation of the coating solution. A time during the period after the preparation of the silver salt of an organic acid and immediately before coating is preferred. The azolium salt may be added as any form such as powder, solution and microparticle dispersion. The salt may also be added as a solution prepared by mixing the salt with other additives such as a sensitizing dye, reducing agent and toning agent. The amount of the azolium salt to be added is not particularly limited, and the amount may preferably be $1\times10^{-6}$ mole to 2 moles, more preferably $1\times10^{-3}$ mole to 0.5 mole, per mole of silver.

The thermally processed image recording material may optionally contain a mercapto compound, disulfide compound or thione compound to accelerate, suppress, or control development, or increase efficiency in spectral sensitivity, or to improve storability before and after development. Examples thereof include, for example, those compounds described in JP-A-10-62899, paragraphs 0067 to 0069, compounds of the formula (I) and specific examples thereof mentioned in JP-A-10-186572, paragraphs 0033 to 0052, those described in EP0803764A1, page 20, lines 36 to 56, those described in Japanese Patent Application No. 11-273670. Among them, mercapto-substituted heteroaromatic compounds are preferred.

A toning agent is preferably added to the thermally processed image recording material. Examples of the toning agent are described in JP-A-10-62899, paragraphs 0054 to 0055, EP0803764A1, page 21, lines 23 to 48 and Japanese Patent Application No. 11-213487. Preferred examples include phthalazinones (e.g., phthalazinone, phthalazinone derivatives such as 4-(1-naphthyl)phthalazinone, 6-chlorophthalazinone, 5,7-dimethoxyphthalazinone and 2,3-dihydro-1,4-phthalazinone metal salts thereof); combinations of phthalazinones and phthalic acids (e.g., phthalic acid, 4-methylphthalic acid, 4-nitrophthalic acid, tetrachlorophthalic anhydride and so forth); phthalazines (e.g., phthalazine, phthalazine derivatives such as 4-(1-naphthyl)phthalazine, 6-isopropyl-phthalazine, 6-t-butylphthalazine, 6-chlorophthalazine, 5,7-dimethoxyphthalazine and 2,3-dihydrophthalazine and metal salts thereof); combinations of phthalazines and phthalic acids. Particularly preferred examples include the combinations of phthalazines and phthalic acids.

Plasticizers and lubricants that can be used for the image-forming layer are described in JP-A-11-65021, paragraph 0117. Ultrahigh contrast agents for forming ultrahigh contrast images and addition methods and amounts therefor are described in the same publication, paragraph 0118, JP-A-11-223898, paragraphs 0136 to 0193, Japanese Patent Application No. 11-87297, compounds of the formula (H), formulas (1) to (3), formulas (A) and (B) and those mentioned in Japanese Patent Application No. 11-91652 as compounds of the formulas (III) to (V) (specific compounds: Chem. 21 to Chem 24); and hardness enhancement promoters are described in JP-A-11-65021, paragraph 0102, and JP-A-11-223898, paragraphs 0194 to 0195.

When formic acid or a formic acid salt is used as a strongly fogging substance, it is preferably used on the side having the image-forming layer containing a photosensitive silver halide in an amount of 5 mmol or less, more preferably 1 mmol or less, per 1 mole of silver.

When an ultrahigh contrast agent is used in the thermally processed image recording material, an acid formed by hydration of diphosphorus pentoxide or a salt thereof is preferably used together with the ultrahigh contrast agent. Examples of the acid formed by hydration of diphosphorus pentoxide or a salt thereof include metaphosphoric acid (salt), pyrophosphoric acid (salt), orthophosphoric acid (salt), triphosphoric acid (salt), tetraphosphoric acid (salt), hexametaphosphoric acid (salt) and so forth. Particularly preferably used acids formed by hydration of diphosphorus pentoxide or salts thereof are orthophosphoric acid (salt) and hexametaphosphoric acid (salt). Specific examples of the salt are sodium orthophosphate, sodium dihydrogenorthophosphate, sodium hexametaphosphate, ammonium hexametaphosphate and so forth.

The acid formed by hydration of diphosphorus pentoxide or a salt thereof may be used in a desired amount (coating amount per 1 $m^2$ of the thermally processed image recording material) depending on the desired performance including sensitivity and fog. However, it can be used in an amount of preferably 0.1–500 mg/$m^2$, more preferably 0.5–100 mg/$m^2$.

The thermally processed image recording material may be provided with a surface protective layer, for example, to prevent adhesion of the image-forming layer. The surface protective layer may consist of a single layer or a plurality of layers. The surface protective layer is described in, for example, JP-A-11-65021, paragraphs 0119 to 0120.

While gelatin is preferred as the binder in the surface protective layer, polyvinyl alcohol (PVA) is also preferably used. As the gelatin, for example, inert gelatin (e.g., Nitta Gelatin 750), phthalized gelatin (e.g., Nitta Gelatin 801) and so forth can be used. Examples of PVA include, for example, completely saponified PVA, PVA-105, partially saponified PVA, PVA-205 and PVA-335, denatured polyvinyl alcohol, MP-203 (all from Kuraray Co., Ltd.) and so forth. The application amount of the polyvinyl alcohol (per $m^2$ of the support) for protective layers is preferably 0.3–4.0 g/$m^2$, more preferably 0.3–2.0 g/$m^2$ (per one layer).

When the thermally processed image recording material is used for, in particular, printing use in which dimensional change is critical, polymer latex is preferably used also in a protective layer or a back layer. Such latex is described in "Gosei Jushi Emulsion (Synthetic Resin Emulsion)", compiled by Taira Okuda and Hiroshi Inagaki, issued by Kobunshi KankoKai (1978); "Gosei Latex no Oyo (Application of Synthetic Latex)", compiled by Takaaki Sugimura, Yasuo Kataoka, Souichi Suzuki and Keishi Kasahara, issued by Kobunshi Kanko Kai (1993); Soichi Muroi, "Gosei Latex no Kagaku (Chemistry of Synthetic Latex)", Kobunshi Kanko Kai (1970) and so forth. Specific example thereof include latex of methyl methacrylate (33.5 weight %)/ethyl acrylate (50 weight %)/methacrylic: acid (16.5 weight %) copolymer, latex of methyl methacrylate (47.5 weight %)/butadiene (47.5 weight %)/itaconic acid (5 weight %) copolymer, latex of ethyl acrylate/methacrylic acid copolymer, latex of methyl methacrylate (58.9 weight %)/2-ethylhexyl acrylate (25.4 weight %)/ethylene (8.6 weight %)/2-hydroxyethyl methacrylate (5.1 weight %)/acrylic acid (2.0 weight %) copolymer, latex of methyl methacrylate (64.0 weight %)/styrene (9.0 weight %)/butyl acrylate (20.0 weight %)/2-hydroxyethyl methacrylate (5.0 weight %)/acrylic acid (2.0 weight %) copolymer and so forth. As for the binder of the protective layer, there may be used the combination of polymer latex disclosed in Japanese Patent Application No. 11-6872, and techniques disclosed in Japanese Patent Application No. 11-143058, paragraphs 0021–0025, Japanese Patent Application No. 11-6872, paragraphs 0027–0028, and Japanese Patent Application No. 11-199626, paragraphs 0023–0041. The ratio of the polymer latex in the surface protective layer with respect to the total binder is preferably 10–90 weight %, particularly preferably 20–80 weight %.

Coated amount of the total binder (including wafer-soluble polymer and latex polymer) in the surface protective layer (for one layer) is preferably 0.3–5.0 g/$m^2$, more preferably 0.3–2.0 g/$m^2$ (per $m^2$ of the support).

The temperature for preparation of the coating solution for the image-forming layer may preferably be 30° C. to 65° C., more preferably 35° C. to 60° C., most preferably 35° C. to 55° C. The temperature of the coating solution immediately after the addition of the polymer latex may preferably be kept at 30° C. to 65° C. A reducing agent and a silver salt of an organic acid may preferably be mixed before the addition of polymer latex.

The image-forming layer is provided as one or more layers on the support. When it is provided as a monolayer, the layer must contain a silver salt of an organic acid, photosensitive silver halide, reducing agent and binder, and it may contain desired additional materials such as toning agent, coating aid and other auxiliary agents. When the layer is bilayer, the first image-forming layer (in general, the layer adjacent to the support) must contain a silver salt of an organic acid and silver halide, and the second image-forming layer or said two layers must contain the other ingredients. Multicolor photothermographic material may contain these two layers for each color, or may contain all necessary ingredients in a single layer as described in U.S. Pat. No. 4,708,928. As for multicolor photothermographic materials containing multiple dyes, each image-forming layer (emulsion layer) is kept individually by using a functional or non-functional barrier layer between the adjacent photosensitive layers as described in U.S. Pat. No. 4,460,681.

In the image-forming layer, various types of dyes and pigments may be used to improve color tone, to prevent interference fringes generated during laser exposure, and to prevent irradiation (e.g., C.I. Pigment Blue 60, C.I. Pigment Blue 64, C.I. Pigment Blue 15:6). These techniques are detailed in International Patent Publication WO98/36322, JP-A-10-268465, JP-A-11-338098 and so forth.

In the thermally processed image recording material, an antihalation layer may be provided in a distant position from a light source relative to the image-forming layer.

Thermally processed image recording materials generally have non-photosensitive layers in addition to the image-forming layer (photosensitive layer). Depending on their positions, the non-photosensitive layers are classified into (1) a protective layer to be provided on an image-forming layer (the opposite side of the support); (2) an intermediate layer to be provided between two or more of image-forming layers or between an image-forming layer and a protective layer; (3) an undercoat layer to be provided between an image-forming layer and a support; (4) a back layer to be provided on a side opposite to the image-forming layer. The filter layer is provided in the thermally processed image recording material as the layer (1) or (2). The antihalation layer is provided in the thermally processed image recording material as the layer (3) or (4).

The antihalation layer is described in JP-A-11-65021, paragraphs 0123 to 0124, JP-A-11-223898, JP-A-9-230531, JP-A-10-36695, JP-A-10-104779, JP-A-11-231457, JP-A-11-352625, JP-A-11-352626 etc.

The antihalation layer contains an antihalation dye that shows absorption for the light exposure wavelength. When the light exposure wavelength is in the infrared region, an infrared absorption dye can be used, and in such a case, it is preferable to use a dye that does not show absorption for the visible region.

When the antihalation is attained by using a dye that shows absorption for the visible region, it is preferably used in such a manner that color of the dye should not substantially remain after the image formation. To this end, means for enabling decoloration by the heat of heat development is preferably used, and it is particularly preferable to add a thermodecoloring dye and a base precursor to a non-photosensitive layer so that the layer should function as an antihalation layer. These techniques are disclosed in JP-A-11-231457 and so forth.

The amount of the decoloring dye may be determined depending on purpose of the dye. In general, the dye is used in an amount to give an optical density (absorbance) of larger than 0.1 measured at an intended wavelength. The optical density is preferably 0.2 to 2. The amount of the dye to give such optical density may be generally from about 0.001 to about 1 g/$m^2$.

Decoloring of dyes in that manner can lower optical density of the material to 0.1 or less. Two or more different decoloring dyes may be used in the thermodecoloring type recording materials or thermally processed image recording materials. Similarly, two or more different base precursors may be used in combination.

In such thermal decoloration utilizing a decoloring dye and base precursor, it is preferable to use together a substance that decreases the melting point by 3° C. (deg) or more when it is mixed with a base precursor, such as those described in JP-A-11-352626 (e.g., diphenylsulfone, 4-chlorophenyl-(phenyl)sulfone) in view of thermodecoloration property etc.

A colorant that shows absorption maximum in the range of 300–450 nm may be added in order to improve change of silver color tone and images with time. Such a colorant is described in JP-A-62-210458, JP-A-63-104046, JP-A-63-103235, JP-A-63-208846, JP-A-63-306436, JP-A-63-314535, JP-A-01-61745, Japanese Patent Application No. 11-276751 and so forth.

Such a colorant is usually added in an amount of 0.1 mg/m$^2$ to 1 g/m$^2$, and it is preferably added to a back layer, which is provided on the side opposite to the side on which the image-forming Layer is provided.

The thermally processed image recording material is preferably a so-called single-sided photosensitive material comprising at least one image-forming layer containing a silver halide emulsion on one side of support, and a back layer on the other side.

The thermally processed image recording material may preferably contain a matting agent for improving the transferability of the material. Matting agents are described in JP-A-11-65021, paragraphs 0126 to 0127. The matting agent is preferably added in an amount of 1–400 mg/m$^2$, more preferably 5 to 300 mg/m$^2$, as the amount per 1 m$^2$ of the thermally processed image recording material.

While the matting degree of the surface of the emulsion layer is not particularly limited so long as the material is free from stardust defects, Beck's smoothness of the surface is preferably 30 seconds to 2000 seconds, more preferably 40 seconds to 1500 seconds. Beck smoothness can be easily determined according to Japanese Industrial Standard (JIS) P8119, "Test Method for Smoothness of Paper and Paperboard by Beck Test Device" and TAPPI Standard Method T479.

The matting degree of the back layer is preferably falls 10 seconds to 1200 seconds, more preferably 20 seconds to 800 seconds, further preferably 40 seconds to 500 seconds in terms of the Beck's smoothness.

The matting agent may preferably be incorporated in the outermost surface layer or a layer which functions as the outermost surface layer of the thermally processed image recording material, or alternatively, in a layer close to the outer surface or a layer which acts as a so-called protective layer.

The back layers that are applicable to the thermally processed image recording material are described in JP-A-11-65021, paragraphs 0128 to 0130.

The thermally processed image recording material preferably has a film surface pH of 6.0 or less, more preferably 5.5 or less before heat development. While the lower limit is not particularly defined, it is normally around 3. For controlling the film surface pH, an organic acid such as phthalic acid derivatives or a nonvolatile acid such as sulfuric acid, and a volatile base such as ammonia are preferably used to lower the film surface pH. In particular, ammonia is preferred to achieve a low film surface pH, because it is highly volatile and therefore it can be removed before coating or heat development. A method for measuring the film surface pH is described in Japanese Patent Application No. 11-87297, paragraph 0123.

A hardening agent may be added to the image-forming layer, the protective layer, the back layer and other layers. Examples of the hardening agent are described in T. H. James, "THE THEORY OF THE PHOTOGRAPHIC PROCESS, FOURTH EDITION", Macmillan Publishing Co., Inc., 1977, pp. 77–87. There may be preferably used chromium alum, 2,4-dichloro-6-hydroxy-s-triazine sodium salt, N,N-ethylenebis(vinylsulfonacetamide), N,N-propylene-bis (vinylsulfonacetamide), as well as the polyvalent metal ions described on page 78 of the above article, polyisocyanates described in U.S. Pat. No. 4,281,060 and JP-A-6-208193; epoxy compounds described in U.S. Pat. No. 4,791,042; vinylsulfone compounds described in JP-A-62-89048 and so forth.

The hardening agent is added to coating solutions as a solution. Preferred addition time of the solution to the coating solution of the protective layer resides in a period of from 180 minutes before the coating to just before the coating, preferably 60 minutes to 10 seconds before the coating. The method and conditions for mixing are not particularly limited. Specific examples of the mixing method include a method in which a mixing is performed in a tank designed so as to obtain a desired average residence time which is calculated from addition flow rate and feeding amount to a coater, a method utilizing a static mixer described in N. Harnby, M. F. Edwards, A. W. Nienow, "Ekitai Kongo Gijutsu (Techniques for Mixing Liquids)", translated by Koji Takahashi, Chapter 8, Nikkan Kogyo Shinbunsha, 1989 and so forth.

Surfactants that can be used in the present invention are described in JP-A-11-65021, paragraph 0132; usable solvents are described in the above patent document in paragraph 0133; usable supports are described in the above patent document in paragraph 0134; usable antistatic and electroconductive layers are described in the above patent document in paragraph 0135; and usable methods for forming color images are described in the above patent document in paragraph 0136; lubricants are described in JP-A-11-84573, paragraphs 0061–0064 and Japanese Patent Application No. 11-106881, paragraphs 0049–0062.

Preferably used as a transparent support is a polyester film, in particular, polyethylene terephthalate film, subjected to a heat treatment in a temperature range of 130–185° C. in order to relax the internal distortion formed in the film during the biaxial stretching so that thermal shrinkage distortion occurring during the heat development should be eliminated. When the thermally processed image recording material is for medical use, the transparent support may be colored with blue dyes (e.g., with Dye-1 described in Examples of JP-A-8-240877), or may be colorless. For the support, techniques for undercoating described in JP-A-11-84574 (utilizing water-soluble polyester), JP-A-10-186565 (utilizing styrene/butadiene copolymer), JP-A-11-106881, paragraphs 0063–0080 (utilizing vinylidene chloride copolymer) and so forth are preferably used. As for antistatic layers and undercoating, techniques disclosed in JP-A-56-143430, JP-A-56-143431, JP-A-58-62646, JP-A-56-120519, JP-A-11-84573, paragraphs 0040–0051, U.S. Pat. No. 5,575,957, JP-A-11-223898, paragraphs 0078–0084 and so forth can also be used.

The thermally processed image recording material is preferably a monosheet type material (the monosheet uses no additional sheet as required by image receiving materials, and can form images directly on the thermally processed image recording material itself).

The thermally processed image recording material may further contain an antioxidant, a stabilizer, a plasticizer, an ultraviolet absorber or a coating aid. Such additives may be added to any of image-forming layers (photosensitive layers) or non-photosensitive layers. For these additives, WO98/36322, EP803764A1, JP-A-10-186567, JP-A-10-18568 and so forth may be referred to.

The coating method for the preparation of the thermally processed image recording material of the present invention is not particularly limited, and any coating methods maybe employed. Specific examples thereof include various types of coating techniques, for example, extrusion coating, slide coating, curtain coating, dip coating, knife coating, flow coating, extrusion coating utilizing a hopper of the type described in U.S. Pat. No. 2,681,294 and so forth. Preferred examples include extrusion coating and slide coating described in Stephen F. Kistler, Petert M. Schweizer, "LIQUID FILM COATING", published by CHAPMAN & HALL Co., Ltd., 1997, pp. 399–536, and a most preferable example includes the slide coating. An example of the shape of a slide coater used for the slide coating is shown in FIG. 11b, 1, on page 427 of the aforementioned reference. If desired, two or more layers may be formed at the same time, for example, according to the methods described from page 399 to page 536 of the aforementioned reference, or the methods described in U.S. Pat. No. 2,761,791 and British Patent No. 837,095.

The coating solution for the image-forming layer is preferably a so-called thixotropic flow. Thixotropy means a property of fluid that viscosity of fluid lowers with increase of shear rate. While any apparatus may be used for measurement of viscosity, for example, RFS Fluid Spectrometer from Rheometrics Far East Co., Ltd. is preferably used and the measurement is performed at 25° C. Viscosity of the coating solution for the image-forming layer is preferably 400 mPa·s to 100,000 mPa·s, more preferably 500 mPa·s to 20,000 mPa·s, ta shear rate of 0.1 $\sec^{-1}$. The viscosity is preferably 1 mPa·s to 200 mPa·s, more preferably 5 mPa·s to 80 mPa·s, at a shear rate of 1000 $\sec^{-1}$.

Various systems exhibiting thixotropic property are known and, for example, described in "Koza Rheology (Lecture on Rheology)", Kobunshi Kanko Kai; Muroi & Morino, "Kobunshi Latex (Polymer Latex)", Kobunshi Knako Kai and so forth. A fluid is required to contain a large amount of fine solid microparticles to exhibit thixotropic property. For enhancing thixotropic property, it is effective that the fluids is added with a viscosity-increasing linear polymer, or fine solid microparticles to be contained have anisotropic shapes and an increased aspect ratio. Use of an alkaline viscosity-increasing agent or a surfactant is also effective for that purpose.

Other techniques that can be used for the production of the thermally processed image recording material are also described in EP803764A1, EP883022A1, WO98/36322, JP-A-56-62648, JP-A-58-62744, JP-A-9-281637, JP-A-9-297367, JP-A-9-304869, JP-A-9-311405, JP-A-9-329865, JP-A-10-10669, JP-A-10-62899, JP-A-10-69023, JP-A-10-186568, JP-A-10-90823, JP-A-10-171063, JP-A-10-186565, JP-A-10-186567, JP-A-10-186569, JP-A-10-186570, JP-A-10-186571, JP-A-10-186572, JP-A-10-197974, JP-A-10-197982, JP-A-10-197983, JP-A-10-197985, JP-A-10-197986, JP-A-10-197987, JP-A-10-207001, JP-A-10-207004, JP-A-10-221807, JP-A-10-282601; JP-A-10-288823, JP-A-10-288824, JP-A-10-307365, JP-A-10-312038, JP-A-10-339934, JP-A-11-7100, JP-A-11-15105, JP-A-11-24200, JP-A-11-24201, JP-A-11-30832, JP-A-11-84574, JP-A-11-65021, JP-A-11-109547, JP-A-11-125880, JP-A-11-129629, JP-A-11-133536, JP-A-11-133537, JP-A-11-133538, JP-A-11-133539, JP-A-11-133542, JP-A-11-133543, JP-A-11-223898 and JP-A-11-352627.

The thermally processed image recording material of the invention may be developed in any manner. Usually, an imagewise exposed thermally processed image recording material is developed by heating. The temperature for the development is preferably 80° C. to 250° C., more preferably 100° C. to 140° C. The development time is preferably 1–180 seconds, more preferably 10–90 seconds, particularly preferably 10–40 seconds.

For thermal development for the material, preferred is a plate heater system. For heat development by the plate heater system, the method described in JP-A-11-133572 is preferred. The plate heater system described in this references is a heat development apparatus wherein a thermally processed image recording material on which a latent image is formed is brought into contact with a heating means in a heat development section to obtain a visible image. In this apparatus, the heating means comprises a plate heater, and a plurality of presser rollers are disposed facing to one surface of the plate heater. Heat development of the thermally processed image recording material is attained by passing the material between the presser rollers and the plate heater. The plate heater is preferably sectioned into 2 to 6 stages, and the temperature of the top stage is preferably kept lower by 1 to 10° C. or so than that of the others. Such a method is also described in JP-A-54-30032. Such a plate heater system can remove moisture and organic solvent contained in the thermally processed image recording material out of the material, and prevent deformation of the support of the thermally processed image recording material due to rapid heating of the material.

The thermally processed image recording material of the present invention can be exposed in any manner. As light source of exposure, laser rays are preferred. As the laser used in the present invention, gas lasers ($Ar^+$, He—Ne), YAG lasers, dye lasers, semiconductor lasers and so forth are preferred. A combination of semiconductor laser and second harmonic generating device may also be used. Preferred are gas or semiconductor lasers for red to infrared emission.

As an example of a laser imager provided with a light exposure section and a heat development section, Fuji Medical Dry Laser Imager FM-DP L can be mentioned. FM-DP L is explained in Fuji Medical Review, No. 8, pages 39–55, and those techniques can of course be used in laser imagers for the thermally processed image recording material. Further, it can be used as a thermally processed image recording material for laser imagers in "AD network", which was proposed by Fuji Medical System as a network system that conforms to the DICOM standard.

The thermally processed image recording material forms a monochromatic image based on silver image, and is preferably used as a thermally processed image recording material for use in medical diagnosis, industrial photography, printing and COM.

The present invention will be specifically explained with reference to the following examples. The materials, amounts, ratios, types of treatments, procedures of treatments and so forth shown in the following examples can be optionally changed so long as such change does not depart from the spirit of the present invention. Therefore, the scope of the present invention is not limited to the following examples.

EXAMPLE 1

Preparation of Organic Acid Silver Salt Grain Dispersion A

In an amount of 87.6 g of behenic acid (Edenor C22-85R, trade name, manufactured by Henkel Co.), 423 mL of distilled water, 49.2 mL of 5 mol/L aqueous solution of NaOH, and 120 mL of tert-butanol were stirred and allowed to react at 75° C. for one hour to obtain a solution of sodium behenate. Separately, 206.2 mL of an aqueous solution containing 40.4 g of silver nitrate (pH 4.0) was prepared and kept at 10° C. A mixture of 635 mL of distilled water and 30 mL of tert-butanol contained in a reaction vessel kept at 30° C. was added with the whole volume of the aforementioned sodium behenate solution and the whole volume of the aqueous silver nitrate solution with stirring at constant flow rates over the periods of 93 minutes and 90 minutes, respectively. In this operation, they were added in such a manner that only the aqueous silver nitrate solution was added for 11 minutes after starting the addition of the aqueous silver nitrate solution. Then, the addition of the sodium behenate solution was started so that only the sodium behenate solution should be added for 14 minutes after finishing the addition of the aqueous silver nitrate solution. In this operation, the outside temperature was controlled so that the temperature in the reaction vessel should be 30° C. and the liquid temperature should be constant. The pipeline of the addition system for the sodium behenate solution was warmed with double pipe and warmed water at 80° C. was supplied an outside jacket of the double pipe so that the liquid temperature at the outlet orifice of the addition nozzle end should be maintained at 75° C. Further, cold water at 8° C. was circulated in an outside jacket of double pipe for the pipeline of the addition system for the aqueous silver nitrate solution, so that the liquid temperature at the outlet orifice at the addition nozzle end should be maintained at 10° C. The addition position of the sodium behenate solution and the addition position of the aqueous silver nitrate solution were arranged symmetrically with respect to the stirring axis as the center, and the positions are controlled to be at heights for not contacting with the reaction mixture.

After finishing the addition of the sodium behenate solution, the mixture was left with stirring for 20 minutes at the same temperature and then the temperature was decreased to 25° C. Then, the solid content was separated by suction filtration and washed with water until electric conductivity of the filtrate became 50 µS/cm. Thus, a silver salt of an organic acid was obtained. The solid content obtained as described above was stored as a wet cake without being dried.

To the wet cake corresponding to 100 g of the dry solid content was added with 7.4 g of polyvinyl alcohol (PVA-217, trade name) and water to make the total amount 385 g, and the mixture was pre-dispersed by a homomixer.

Then, the pre-dispersed stock dispersion was treated three times by using a dispersing machine (Microfluidizer M110S-EH; trade name, manufactured by Microfluidex International Corporation, using G10Z interaction chamber) with a pressure controlled to be 1750 kg/cm$^2$ to obtain a silver behenate dispersion. As for the cooling operation, a dispersion temperature of 18° C. was achieved by providing coiled heat exchangers fixed before and after the interaction chamber and controlling the temperature of the refrigerant.

Preparation of Organic Acid Silver Salt Grain Dispersion B

Dispersion B was prepared by using such a facility as shown in FIG. 3. In the tank 30, 87.6 g of behenic acid (Edenor C22-85R, trade name, manufactured by Henkel Co.), 423 mL of distilled water and 120 mL of tert-butanol were added with 49.2 mL of 5 mol/L aqueous solution of NaOH over 5 minutes at 75° C. with stirring, and allowed to react at for 60 minutes to obtain a solution of sodium behenate. Separately, 206.2 mL of an aqueous solution containing 40.4 g of silver nitrate (pH 4.0) was prepared and kept at 10° C. in the tank 29. Further, 600 mL of pure water was measured in the tank 38, and circulated through the pipeline mixer 37, Model LR-1 produced by Mizuho Kogyo Co., Ltd., via the pump 35 at a flow rate of 100 mL/minute. While stirring was performed by operating the pipeline mixer at 10,000 rpm, the aqueous solution of silver nitrate was added at a constant flow rate of 2.9 ml/minute by using the pump 33, and after 5 seconds, addition of the aqueous solution of sodium behenate was started at a constant flow rate of 9.8 mL/minute, so that the solutions were stored in the tank 38. Cooling water at 10° C. was supplied to a jacket of the tank 38 at a flow rate of 2 L/minute, and as a result, the average temperature in the tank was measured to be 30° C.

After finishing the addition of the sodium behenate solution, the temperature was decreased to 25° C. over 20 minutes, and then 85 mL of a 4 weight % solution of polyvinyl alcohol (trade name: PVA-217) was added. The mixture was left as it was with stirring for 20 minutes.

Thereafter, the obtained dispersion containing the organic acid silver salt grains was transferred from the tank 38 to the tank 40 by using the pump 39, and continuously fed to the ultra filtration unit to perform desalting treatment. The ultrafiltration unit was basically constituted by the tank 40 for storing the organic acid silver salt grain dispersion, and a circulation pump 41 for supplying the stored dispersion to the ultrafiltration module 42, and further provided with a flowmeter 44 for measurement of supplemented pure water and a flowmeter 43 for measurement of permeated water. The membrane module used was a hollow-fiber type one, ACP-1050 produced by Asahi Chemical Industry Co., Ltd., which had a fractional molecular weight of 13,000. Constant volume filtration was performed by supplementing pure water at a feeding flow rate of 6 L/minute and a pressure difference before and after the module of 1.0 kg/cm$^2$. In this operation, the constant volume dilution ratio was 5 times. Then, the supplementation of water was stopped. At this time, the electric conductivity was 100 µS/cm. Thereafter, the dispersion was further concentrated to a concentration of 26 weigh %. The solid content was measured by using a digital specific gravimeter, Model DA-300, produced by Kyoto Electronics Manufacturing Co., Ltd., and finally determined based on absolute dry weight.

Preparation of Organic Acid Silver Salt Grain Dispersion C

In an amount of 87.6 g of behenic acid (Edenor C22-85R, trade name, manufactured by Henkel Co.), 423 mL of distilled water, 49.2 mL of 5 mol/L aqueous solution of NaOH and 120 mL of tert-butanol were mixed and allowed to react at 75° C. for one hour with stirring to obtain a solution of sodium behenate. Separately, 206.2 mL of an aqueous solution containing 40.4 g of silver nitrate (pH 4.0) was prepared and kept at 10° C. A mixture of 635 mL of distilled water and 30 mL of tert-butanol contained in a reaction vessel kept at 30° C. was added with the whole volume of the aforementioned sodium behenate solution and the whole volume of the aqueous silver nitrate solution with stirring at constant flow rates over the periods of 93 minutes and 90 minutes, respectively. In this operation, they were added in such a manner that only the aqueous silver nitrate solution was added for 11 minutes after starting the addition of the aqueous silver nitrate solution. Then, the addition of the sodium behenate solution was started so that only the sodium behenate solution should be added for 14 minutes after finishing the addition of the aqueous silver nitrate solution. In this operation, the outside temperature was controlled so that the temperature in the reaction vessel should be 30° C. and the liquid temperature should be constant. The pipeline of the addition system for the sodium behenate solution was warmed with double pipe and warmed water at 80° C. was supplied an outside jacket of the double pipe so that the liquid temperature at the outlet orifice of the addition nozzle end should be maintained at 75° C. Further, cold water at 8° C. was circulated in an outside jacket of double pipe for the pipeline of the addition system for the aqueous silver nitrate solution, so that the liquid temperature at the outlet orifice at the addition nozzle end should be maintained at 10° C. The addition position of the sodium behenate solution and the addition position of the aqueous silver nitrate solution were arranged symmetrically with respect to the stirring axis as the center, and the positions are controlled to be at heights for not contacting with the reaction mixture.

After finishing the addition of the sodium behenate solution, the temperature was decreased to 25° C. over 20 minutes, and 85 mL of a 4 weight % solution of polyvinyl alcohol (trade name: PVA-217) was added. The mixture was left as it was with stirring for 20 minutes.

The obtained organic acid silver salt stock dispersion was continuously fed to an ultrafiltration unit in the same manner as that for organic acid silver salt grain dispersion B to subject it to desalting.

When the electric conductivity decreased to 100 μS/cm, the supplementation of pure water was stopped and the concentration operation was started. However, when the solid content concentration reached 16 weight %, the pressure at the filtration module inlet reached 3 kgf/cm$^2$, which was the pressure limit of the membrane, and therefore the concentration was finished. The solid content was measured by using a digital specific gravimeter, Model DA-300, produced by Kyoto Electronics Manufacturing Co., Ltd., and finally determined based on absolute dry weight.

Preparation of Organic Acid Silver Salt Grain Dispersion D

Dispersion D was prepared by using such a facility as shown in FIG. 2. In the tank 16, 87.6 g of behenic acid (Edenor C22-85R, trade name, manufactured by Henkel Co.), 423 mL of distilled water and 120 mL of tert-butanol were added with 49.2 mL of 5 mol/L aqueous solution of NaOH over 5 minutes at 75° C. with stirring, and allowed to react at for 60 minutes to obtain a solution of sodium behenate. Separately, 206.2 mL of an aqueous solution containing 40.4 g of silver nitrate (pH 4.0) was prepared and kept at 10° C. in the tank 15. Further, 600 mL of pure water was measured in the tank 24, and circulated through the pipeline mixer 23, Model LR-1 produced by Mizuho Kogyo Co., Ltd., via the pump 21 at a flow rate of 100 mL/minute. While stirring was performed by operating the pipeline mixer at 10,000 rpm, the aqueous solution of silver nitrate was added at a constant flow rate of 2.9 ml/minute by using the pump 17, and after 5 seconds, addition of the aqueous solution of sodium behenate was started at a constant flow rate of 9.8 mL/minute by using the pump 18, so that the solutions were stored in the tank 24. After 20 minutes, 85 mL of a 4 weight % solution of polyvinyl alcohol (tradename: PVA-217) was added over 1 minutes. Cooling water at 10° C. was supplied to a jacket of the tank 24 at a flow rate of 2 L/minute, and as a result, the average temperature in the tank was measured to be 30° C.

Five minutes after finishing the addition of the polyvinyl alcohol, the obtained dispersion was continuously fed to the ultrafiltration unit to start the desalting treatment.

The ultrafiltration unit was basically constituted by the tank 24 for storing the organic acid silver salt grain dispersion, and a circulation pump 25 for supplying the stored dispersion to the ultrafiltration module 26, and further provided with a flowmeter 28 for measurement of supplemented pure water and a flowmeter 27 for measurement of permeated water. The membrane module used was a hollow-fiber type one, ACP-1050 produced by Asahi Chemical Industry Co., Ltd., which had a fractional molecular weight of 13,000. Constant volume filtration was performed at a feeding flow rate of 6 L/minute and a pressure difference before and after the module of 1.0 kg/cm$^2$. In this operation, the constant volume dilution ratio was 5 times. Then, the supplementation of water was stopped. At this time, the electric conductivity was 100 μS/cm. Thereafter, the dispersion was further concentrated to a concentration of 26 weigh %. The solid content concentration was measured by using a digital specific gravimeter, Model DA-300, produced by Kyoto Electronics Manufacturing Co., Ltd., and finally determined based on absolute dry weight.

Preparation of Organic Acid Silver Salt Grain Dispersion E

Organic acid silver salt grain dispersion E was prepared in the exactly same manner as that for Organic acid silver salt grain dispersion B except that the macromolecular dispersing agent was changed from the polyvinyl alcohol to polyvinylpyrrolidone (GAF Corporation, trade name: PVPK-30)<

Preparation of Organic Acid Silver Salt Grain Dispersion F

Organic acid silver salt grain dispersion F was prepared in the exactly same manner as that for Organic acid silver salt grain dispersion B except that the macromolecular dispersing agent was changed from the polyvinyl alcohol to hydroxyethyl cellulose (Daicel Chemical Industries, Ltd., tradename: SP550).

The preparation conditions of Organic acid silver salt grain dispersions A to F are summarized in Table 1.

TABLE 1

| Organic acid silver salt grain Dispersion | Type of Dispersing Agent | Grain size Average (μm) | Grain size Variation Coefficient (%) | Filtration rate (L/m²h) During constant volume dilution | Filtration rate (L/m²h) After Concentration | Attained solid content concentration (wt. %) |
|---|---|---|---|---|---|---|
| A (Comparative) | PVA | 0.62 | 16 | — | — | — |
| B (Invention) | PVA | 0.37 | 17 | 26 | 13 | 26 |
| C (Comparative) | PVA | 6.09 | 48 | 13 | 5 | 16 |
| D (Invention) | PVA | 0.58 | 20 | 29 | 14 | 26 |
| E (Invention) | PVP | 0.46 | 22 | 23 | 11 | 26 |
| F (Invention) | HEC | 0.51 | 22 | 21 | 10 | 26 |

(NOTE)
PVA: Polyvinyl alcohol,
PVP: polyvinylpyrrolidone,
HEC: hydroxyethyl cellulose Organic acid silver salt grain dispersion B prepared by the method of the present invention contained finer grains compared with Organic acid silver salt grain dispersion A prepared by a conventional technique. Since the method enabled preparation of such fine grains without complicated procedure including suction filtration, washing with water and dispersion, it was demonstrated to be a preferred method providing high productivity.

On the other hand, Organic acid silver salt grain dispersion C prepared by a conventional technique was a dispersion in which primary grains were markedly aggregated, and therefore the filtration rate during the ultrafiltration performed after the preparation was slow. Further, a dispersion having a desired solid content concentration could not be obtained due to the pressure elevation during the concentration operation. In contrast, Organic acid silver salt grain dispersions D to F prepared by the method of the present invention showed high filtration rates, and dispersions having desired solid content concentrations could easily be obtained.

EXAMPLE 2

Preparation of Organic Acid Silver Salt Grain Dispersion AA

Figure 6:
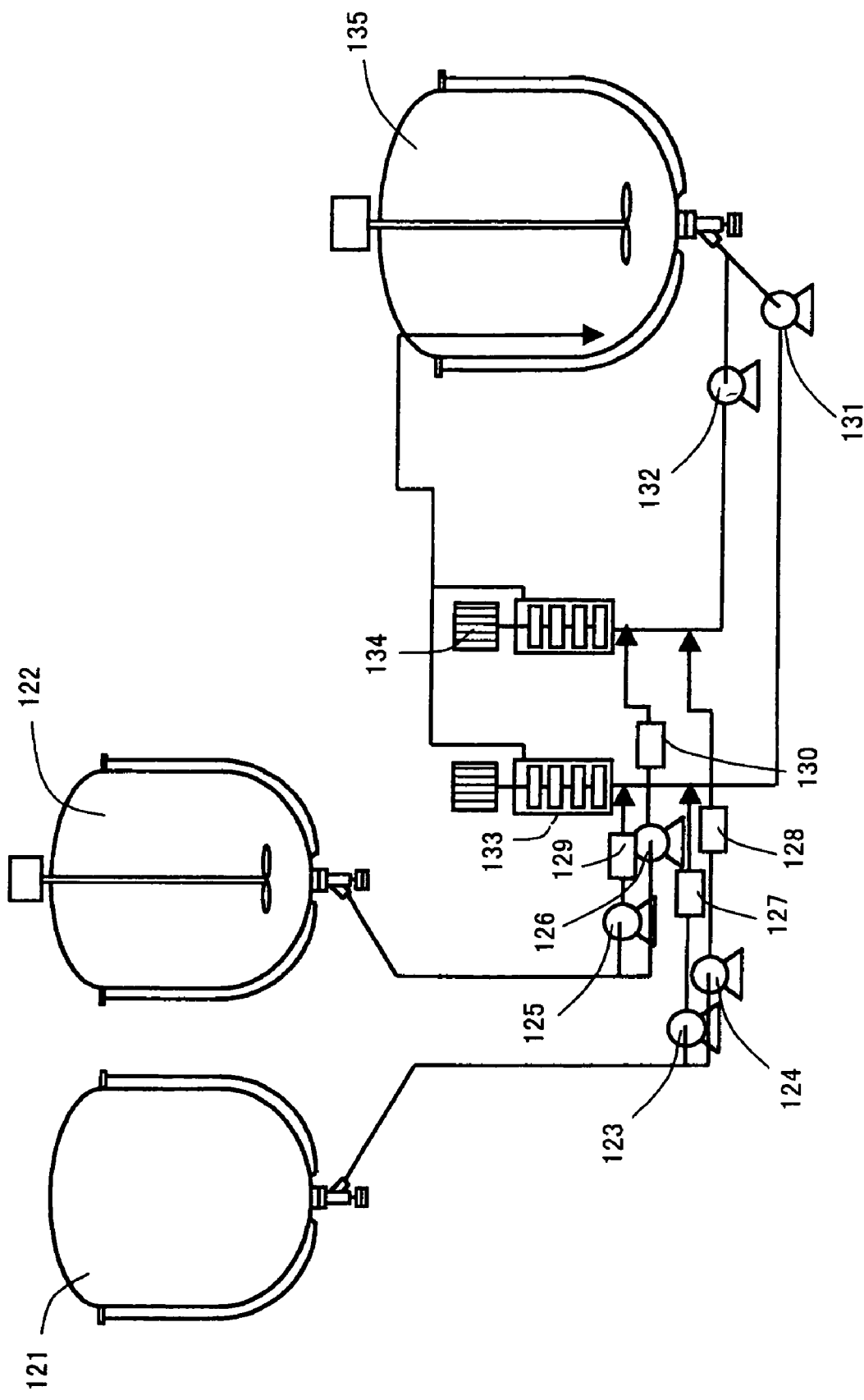
FIG. 6 is a schematic view showing the apparatus used in Example 2.

Organic acid silver salt grain dispersion AA was prepared by using such a large scale crystallization facility as shown in FIG. 6. That is, to the tank 122, 87.6 kg of behenic acid (Edenor C22-85R, trade name, manufactured by Henkel Co.), 423 L of distilled water and 120 L of tert-butanol were added. To the mixture, 49.2 L of 5 mol/L aqueous solution of NaOH was added at 75° over 5 minutes with stirring, and allowed to react for 60 minutes to obtain a solution of sodium behenate. On the other hand, 206.2 L of an aqueous solution containing 40.4 kg of silver nitrate (pH 4.0) was prepared and kept at 10° C. in the tank 121. Further, 600 L of pure water was measured in the tank 135, and circulated via the pumps 131 and 132 through the pipeline mixers 133 and 134 (Model PM-10 produced by Mizuho Kogyo Co., Ltd.) at a flow rate of 50 L/minute for each route. While stirring was performed by operating the pipeline mixers at 3,600 rpm, the aqueous solution of silver nitrate was added at a constant flow rate of 1.45 L/minute to each route by using the pumps 123 and 124, and after 5 seconds, addition of the aqueous solution of sodium behenate was started at a constant flow rate of 4.9 L/minute to each route by using the pumps 125 and 126, so that the solutions were stored in the tank 135. Cooling water at 10° C. was supplied to a jacket of the tank 135 at a flow rate of 200 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 μS/cm. The solid content obtained as described above was stored as a wet cake without being dried.

Distilled water and polyvinyl alcohol were added to the obtained wet cake of organic acid silver salt according to the composition mentioned below, and centrifuged by using T. K. Homodisper Model 2M-5 (Tokushu Kika Kogyo Co., Ltd.) at 5,000 rpm for 15 minute to obtain a crude dispersion.

Composition of Crude Dispersion:

| | |
|---|---|
| Distilled water | 42.4 kg |
| Organic acid silver salt (wet cake having solid content of 40%) | 56 kg |
| Polyvinyl alcohol (PVA-205, Kuraray Co., Ltd.) | 2.2 kg |

The obtained crude dispersion was dispersed once by using Microfluidizer (M110S-EH, using G10Z interaction chamber produced by Mizuho Kogyo Co., Ltd.) at a pressure of 1600 kg/cm² to obtain Organic acid silver salt grain dispersion AA. In this operation, the inlet temperature immediately before the dispersion and the outlet temperature immediately after the dispersion were controlled to be 5° C. and 30° C., respectively.

Preparation of Organic Acid Silver Salt Grain Dispersion BB

Organic acid silver salt grain dispersion BB was prepared in such a large scale crystallization facility as shown in FIG. 6 by using only one addition and mixing line among the two of such lines in the facility. That is, to the tank 122, 43.8 kg of behenic acid (Edenor C22-85R, trade name, manufactured by Henkel Co.), 211.5 L of distilled water and 60 L of tert-butanol were added. To the mixture, 24.6 L of 5 mol/L aqueous solution of NaOH was added at 75° C. over 5 minutes with stirring, and allowed to react for 60 minutes to obtain a solution of sodium behenate. On the other hand, 103.1 L of an aqueous solution containing 20.2 kg of silver nitrate (pH 4.0) was prepared and kept at 10° C. in the tank 121. Further, 300 L of pure water was measured in the tank 135, and circulated via the pump 131 through the pipeline mixer 133 (Model PM-10 produced by Mizuho Kogyo Co., Ltd.) at a flow rate of 50 L/minute. While stirring was performed by operating the pipeline mixer at 3,600 rpm, the aqueous solution of silver nitrate was added at a constant flow rate of 1.45 L/minute by using the pump 123, and after 5 seconds, addition of the aqueous solution of sodium behenate was started at a constant flow rate of 4.9 L/minute by using the pump 125, so that the solutions were stored in the tank 135. Cooling water at 10° C. was supplied to a jacket of the tank 135 at a flow rate of 100 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 µS/cm. The solid content obtained as described above was stored as a wet cake without being dried.

Thereafter, dispersion operation was performed in the same manner as that for Organic acid silver salt grain dispersion AA to obtain Organic acid silver salt grain dispersion BB.

Preparation of Organic Acid Silver Salt Grain Dispersion CC

Organic acid silver salt grain dispersion CC was prepared by using such a large scale crystallization facility as shown in FIG. 4. That is, to the tank 112, 87.6 kg of behenic acid (Edenor C22-85R, trade name, manufactured by Henkel Co.), 423 L of distilled water and 120 L of tert-butanol were added. To the mixture, 49.2 L of 5 mol/L aqueous solution of NaOH was added at 75° C. over 5 minutes with stirring, and allowed to react for 60 minutes to obtain a solution of sodium behenate. On the other hand, 206.2 L of an aqueous solution containing 40.4 kg of silver nitrate (pH 4.0) was prepared and kept at 10° C. in the tank 111. Further, 600 L of pure water was measured in the tank 120, and circulated via the pump 117 through the pipeline mixer 118 (Model PM-20 produced by Mizuho Kogyo Co., Ltd.) at a flow rate of 100 L/minute. While stirring was performed by operating the pipeline mixer at 2,400 rpm, the aqueous solution of silver nitrate was added at a constant flow rate of 2.9 L/minute by using the pump 115, and after 5 seconds, addition of the aqueous solution of sodium behenate was started at a constant flow rate of 9.8 L/minute to by using the pump 116, so that the solutions were stored in the tank 120. Cooling water at 10° C. was supplied to a jacket of the tank 120 at a flow rate of 200 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 µS/cm. The solid content obtained as described above was stored as a wet cake without being dried.

Thereafter, dispersion operation was performed in the same manner as that for Organic acid silver salt grain dispersion AA to obtain Organic acid silver salt grain dispersion CC.

Preparation of Organic Acid Silver Salt Grain Dispersion DD

Organic acid silver salt grain dispersion DD was prepared by using such a large scale crystallization facility as shown in FIG. 4. That is, to the tank 112, 43.8 kg of behenic acid (Edenor C22-85R, trade name, manufactured by Henkel Co.), 211.5 L of distilled water and 60 L of tert-butanol were added. To the mixture, 24.6 L of 5 mol/L aqueous solution of NaOH was added at 75° C. over 5 minutes with stirring, and allowed to react at for 60 minutes to obtain a solution of sodium behenate. On the other hand, 103.1 L of an aqueous solution containing 20.2 kg of silver nitrate (pH 4.0) was prepared and kept at 10° C. in the tank 111. Further, 300 L of pure water was measured in the tank 120, and circulated via the pump 117 through the pipeline mixer 118 (Model PM-20 produced by Mizuho Kogyo Co., Ltd.) at a flow rate of 100 L/minute. While stirring was performed by operating the pipeline mixer at 2,400 rpm, the aqueous solution of silver nitrate was added at a constant flow rate of 2.9 L/minute by using the pump 115, and after 2.5 seconds, addition of the aqueous solution of sodium behenate was started at a constant flow rate of 9.8 L/minute by using the pump 116, so that the solutions were stored in the tank 120. Cooling water at 10° C. was supplied to a jacket of the tank 120 at a flow rate of 200 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 µS/cm. The solid content obtained as described above was stored as a wet cake without being dried.

Thereafter, dispersion operation was performed in the same manner as that for Organic acid silver salt grain dispersion AA to obtain Organic acid silver salt grain dispersion DD.

Preparation of Organic Acid Silver Salt Grain Dispersion EE

Organic acid silver salt grain dispersion EE was prepared by using such a large scale crystallization facility as shown in FIG. 4. That is, to the tank 112, 43.8 kg of behenic acid (Edenor C22-85R, trade name, manufactured by Henkel Co.) 221.5 L of distilled water and 60 L of tert-butanol were added. To the mixture, 24.6 L of 5 mol/L aqueous solution of NaOH was added at 75° C. over 5 minutes with stirring, and allowed to react for 60 minutes to obtain a solution of sodium behenate. On the other hand, 103.1 L of an aqueous solution containing 20.2 kg of silver nitrate (pH 4.0) was prepared and kept at 10° C. in the tank 111. Further, 300 L of pure water was measured in the tank 120, and circulated via the pump 117 through the pipeline mixer 118 (Model PM-20 produced by Mizuho Kogyo Co., Ltd.) at a flow rate of 50 L/minute. While stirring was performed by operating the pipeline mixer at 1,600 rpm, the aqueous solution of silver nitrate was added at a constant flow rate of 1.45 L/minute by using the pump 115, and after 5 seconds, addition of the aqueous solution of sodium behenate was started at a constant flow rate of 4.9 L/minute to by using the pump 116, so that the solutions were stored in the tank 120. Cooling water at 10° C. was supplied to a jacket of the tank 120 at a flow rate of 200 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 µS/cm. The solid content obtained as described above was stored as a wet cake without being dried.

Thereafter, dispersion operation was performed in the same manner as that for Organic acid silver salt grain dispersion AA to obtain Organic acid silver salt grain dispersion EE.

Preparation of Organic Acid Silver Salt Grain Dispersion FF

In an amount of 87.6 kg of behenic acid (Edenor C22-85R, trade name, manufactured by Henkel Co.), 423 L of distilled water and 120 L of tert-butanol stirred at 75° C. in a reaction tank were added with 49.2 L of 5 mol/L aqueous solution of NaOH over 5 minutes, and allowed to react for 60 minutes to obtain a solution of sodium behenate. Separately, 206.2 L of an aqueous solution containing 40.4 kg of silver nitrate (pH 4.0) was prepared and kept at 10° C. A reaction vessel containing 635 L of distilled water and 30 L of tert-butanol was maintained at 30° C., and added with the whole volume of the aqueous silver nitrate solution with stirring at a constant flow rate. After 7 minutes, it was started to add the whole volume of the sodium behenate solution at a constant flow rate. The addition times of the aqueous silver nitrate solution and the sodium behenate solution in this operation were 60 minutes and 62 minute, respectively. Therefore, during the last 9 minutes, only the sodium behenate solution was added. The mixture was left with stirring for 20 minutes as it was to lower the temperature to 25° C. Then, the solid content was separated by suction filtration and washed with water until electric conductivity of the filtrate became 30 μS/cm. The solid content obtained as described above was stored as a wet cake without being dried.

Distilled water and polyvinyl alcohol were added to the obtained wet cake according to the composition mentioned below, and treated by using T. K. Homodisper Model 2M-5 (Tokushu Kika Kogyo Co., Ltd.) at 5,000 rpm for 15 minute to obtain a crude dispersion. The obtained grains had a mean grain size of 5.36 μm.

Composition of Crude Dispersion:

| | |
|---|---|
| Distilled water | 42.4 kg |
| Organic acid silver salt (wet cake having solid content of 40%) | 56 kg |
| Polyvinyl alcohol (PVA-205, Kuraray Co., Ltd.) | 2.2 kg |

The obtained crude dispersion was treated once by using Microfluidizer (M110S-EH, using G10Z interaction chamber produced by Mizuho Kogyo Co., Ltd.) at a pressure of 1600 kg/cm$^2$ to obtain Organic acid silver salt grain dispersion FF. In this operation, the inlet temperature immediately before the dispersion and the outlet temperature immediately after the dispersion were controlled to be 5° C. and 30° C., respectively. The obtained dispersion showed a mean grain size and viscosity of 0.62 μm and 18 mPa·s, respectively, as shown in Table 2.

Preparation of Organic Acid Silver Salt Grain Dispersion GG

Figure 7:
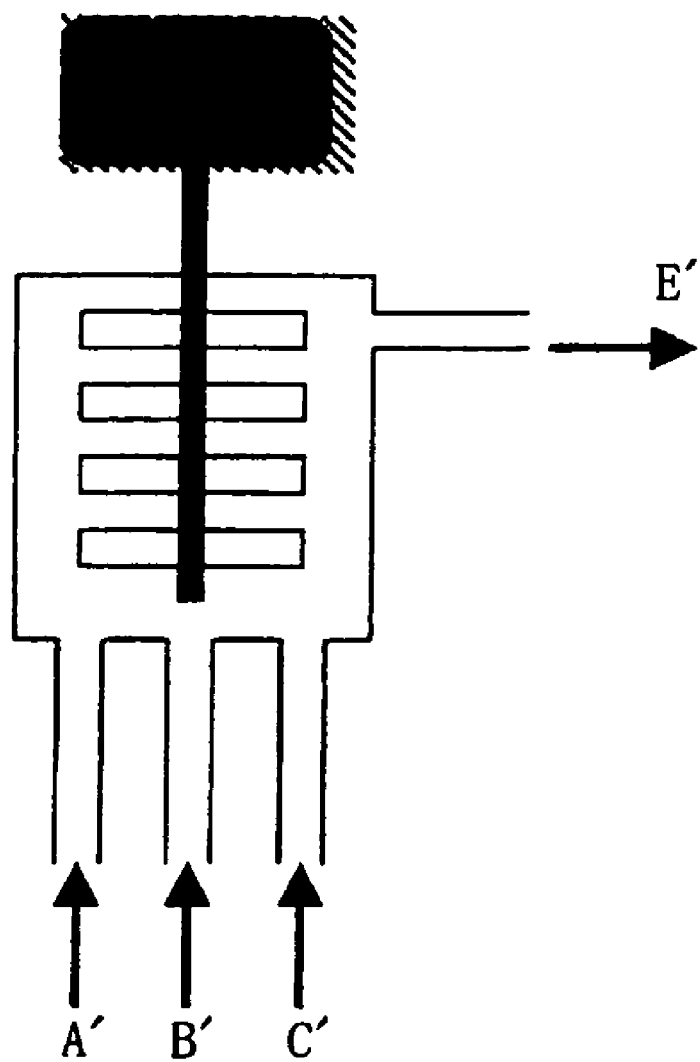
FIG. 7 is a schematic view showing a mixing vessel and its pipelines used in Example 2.

Organic acid silver salt grain dispersion GG was prepared in such a large scale crystallization facility as shown in FIG. 4 by using the addition section and mixing unit shown in FIG. 7 as the pipeline mixer 118. That is, to the tank 112, 87.6 kg of behenic acid (Edenor C22-85R, trade name, manufactured by Henkel Co.), 423 L of distilled water and 120 L of tert-butanol were added. To the mixture, 49.2 L of 5 mol/L aqueous solution of NaOH was added at 75° C. over 5 minutes with stirring, and allowed to react for 60 minutes to obtain a solution of sodium behenate. On the other hand, 206.2 L of an aqueous solution containing 40.4 kg of silver nitrate (pH 4.0) was prepared and kept at 10° C. in the tank 111. Further, 600 L of pure water was measured in the tank 120, and circulated via the pump 117 through the pipeline mixer 18 (Model PM-20 produced by Mizuho Kogyo Co., Ltd., FIG. 4) from a reaction field solution addition inlet C' shown in FIG. 7 at a flow rate of 100 L/minute. While stirring was performed by operating the pipeline mixer at 2,400 rpm, the aqueous solution of silver nitrate was added from a silver ion-containing solution addition inlet A' shown in FIG. 7 at a constant flow rate of 2.9 L/minute, and after 5 seconds, addition of the aqueous solution of sodium behenate was started from an organic acid silver salt solution addition inlet B' shown in FIG. 7 at a constant flow rate of 9.8 L/minute, so that the solutions were stored in the tank 120 via the heat exchanger 119. Cooling water at 10° C. was supplied to the heat exchanger and a jacket of the tank 120 at a flow rate of 200 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 μS/cm. The solid content obtained as described above was stored as a wet cake without being dried.

Thereafter, dispersion operation was performed in the same manner as that for Organic acid silver salt grain dispersion FF to obtain Organic acid silver salt grain dispersion GG.

Preparation of Organic Acid Silver Salt Grain Dispersion HH

Figure 8:
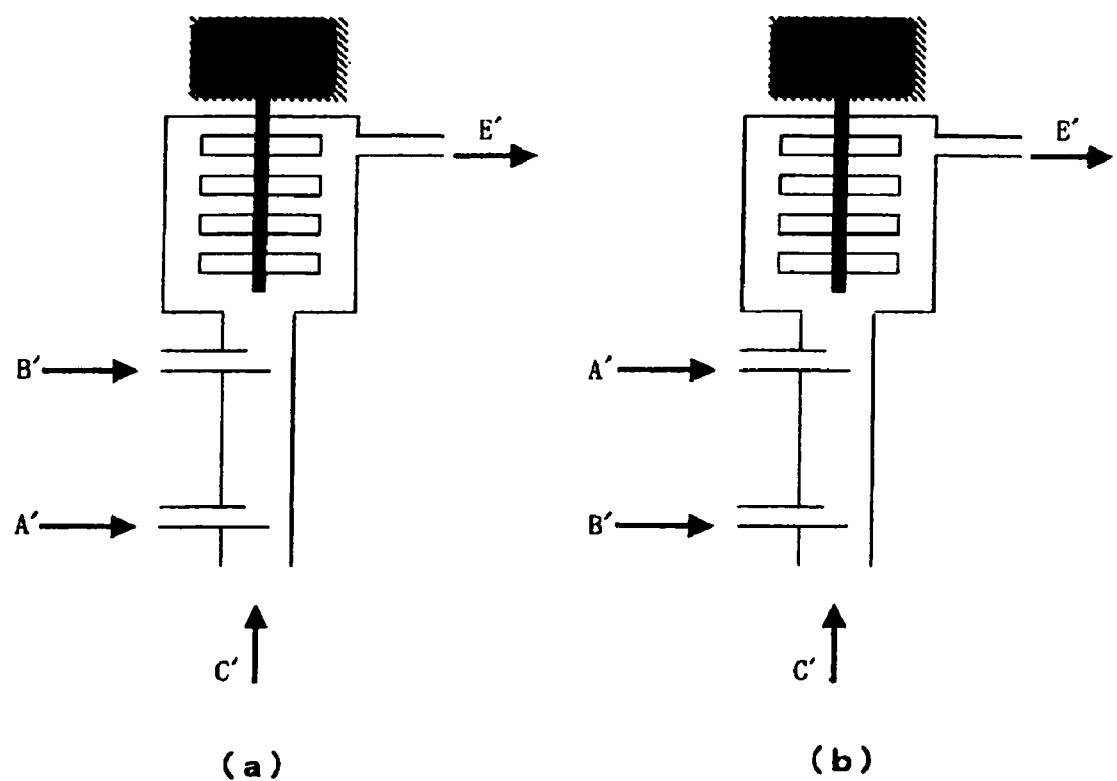
FIG. 8 is a schematic view showing a mixing vessel and its pipelines used in Example 2.

Organic acid silver salt grain dispersion HH was prepared in such a large scale crystallization facility as shown in FIG. 4 by using the addition section and mixing unit shown in FIG. 8(a) as the pipeline mixer 118. That is, to the tank 112, 87.6 kg of behenic acid (Edenor C22-85R, trade name, manufactured by Henkel Co.), 423 L of distilled water and 120 L of tert-butanol were added. To the mixture, 49.2 L of 5 mol/L aqueous solution of NaOH was added at 75° C. over 5 minutes with stirring, and allowed to react for 60 minutes to obtain a solution of sodium behenate. On the other hand, 206.2 L of an aqueous solution containing 40.4 kg of silver nitrate (pH 4.0) was prepared and kept at 10° C. in the tank 111. Further, 600 L of pure water was measured in the tank 120, and circulated via the pump 117 through the pipeline mixer 118 (Model PM-20 produced by Mizuho Kogyo Co., Ltd., FIG. 8(a)) from a reaction field solution addition inlet C' (inner diameter: 56.5 mm) shown in FIG. 8(a) at a flow rate of 100 L/minute. While stirring was performed by operating the pipeline mixer at 2,400 rpm (corresponding to a peripheral speed of 13 m/minute), the aqueous solution of silver nitrate was added from a silver ion-containing solution addition inlet A' (inner diameter: 10 mm) shown in FIG. 8(a) at a constant flow rate of 2.9 L/minute, and after 5 seconds, addition of the aqueous solution of sodium behenate was started from an organic acid silver salt solution addition inlet B' (inner diameter: 13.3 mm) shown in FIG. 8(a) at a constant flow rate of 9.8 L/minute, so that the solutions were stored in the tank 120 via a heat exchanger 119. The distance between the silver ion-containing solution addition inlet A' and the organic acid silver salt solution addition inlet B' was adjusted to 400 mm. Cooling water at 10° C. was supplied to the heat exchanger and a jacket of the tank 120 at a flow rate of 200 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 μS/cm. The solid content obtained as described above was stored as a wet cake without being dried.

Thereafter, dispersion operation was performed in the same manner as that for Organic acid silver salt grain dispersion FF to obtain Organic acid silver salt grain dispersion HH.

Preparation of Organic Acid Silver Salt Grain Dispersion II

Organic acid silver salt grain dispersion II was prepared in such a large scale crystallization facility as shown in FIG. 4 by using the addition section and mixing unit shown in FIG. 8(b) as the pipeline mixer 118. That is, to the tank 111, 87.6 kg of behenic acid (Edenor C22-85R, trade name, manufactured by Henkel Co.), 423 L of distilled water and 120 L of tert-butanol were added. To the mixture, 49.2 L of 5 mol/L aqueous solution of NaOH was added at 75° C. over 5 minutes with stirring, and allowed to react for 60 minutes to obtain a solution of sodium behenate. On the other hand, 206.2 L of an aqueous solution containing 404 kg of silver nitrate (pH 4.0) was prepared and kept at 10° C. in the tank 112. Further, 600 L of pure water was measured in the tank 120, and circulated via the pump 117 through the pipeline mixer 118 (Model PM-20 produced by Mizuho Kogyo Co., Ltd., FIG. 8(b)) from a reaction field solution addition inlet C' (inner diameter: 56.5 mm) shown in FIG. 8(b) at a flow rate of 100 L/minute. While stirring was performed by operating the pipeline mixer at 2,400 rpm, addition of the aqueous solution of sodium behenate was started from an organic acid silver salt solution addition inlet B' (inner diameter: 13.3 mm) shown in FIG. 8(b) at a constant flow rate of 9.8 L/minute, and after 5 seconds, the aqueous solution of silver nitrate was added from a silver ion-containing solution addition inlet A' (inner diameter: 10 mm) shown in FIG. 8(b) at a constant flow rate of 2.9 L/minute, so that the solutions were stored in the tank 120 via the heat exchanger 119. The distance between the organic acid silver salt solution addition inlet B' and the silver ion-containing solution addition inlet A' was adjusted to 400 mm. Cooling water at 10° C. was supplied to the heat exchanger and a jacket of the tank 120 at a flow rate of 200 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 μS/cm. The solid content obtained as described above was stored as a wet cake without being dried.

Thereafter, dispersion operation was performed in the same manner as that for Organic acid silver salt grain dispersion FF to obtain Organic acid silver salt grain dispersion II.

Preparation of Organic Acid Silver Salt Grain Dispersion JJ

Figure 9:
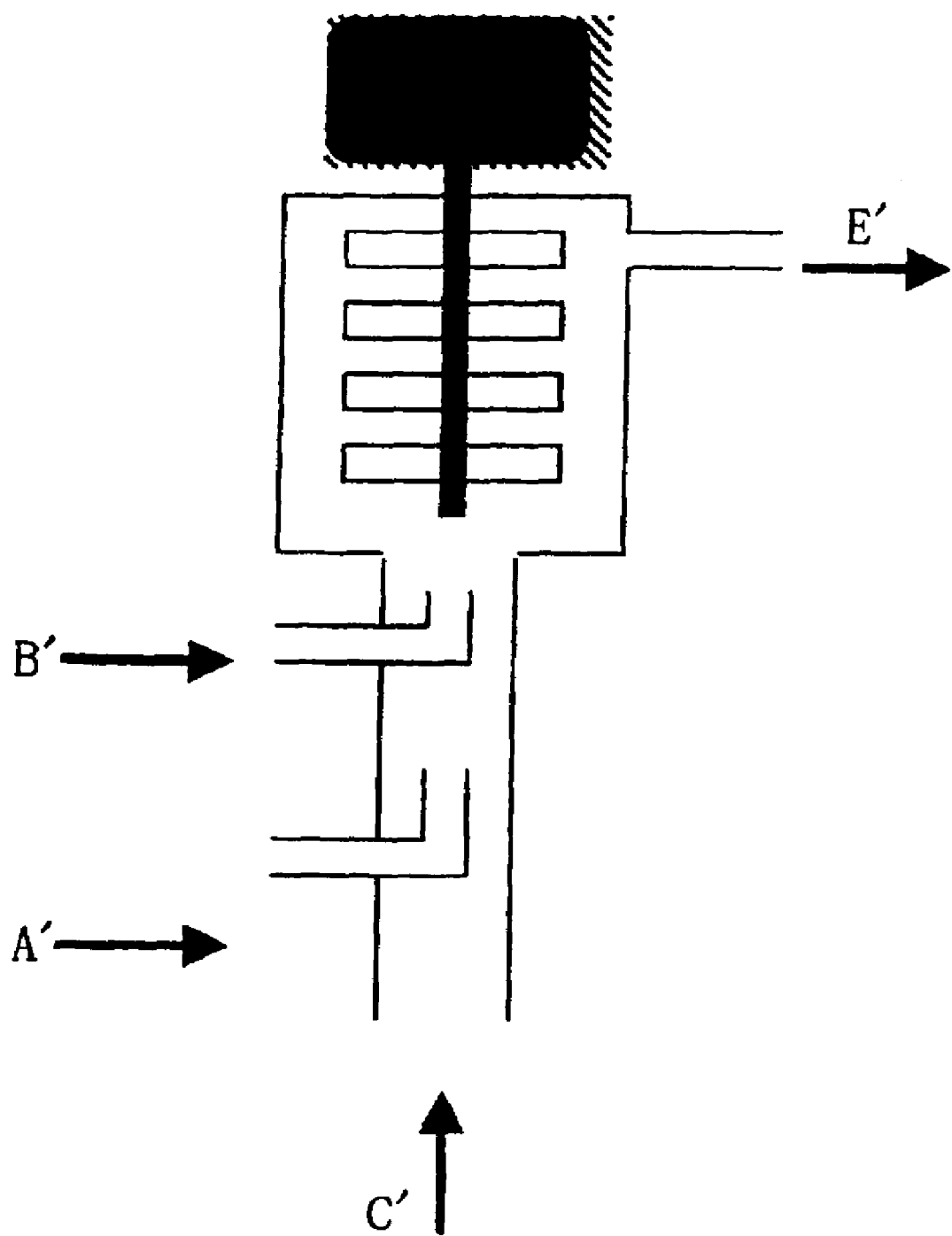
FIG. 9 is a schematic view showing a mixing vessel and its pipelines used in Example 2.

Organic acid silver salt grain dispersion JJ was prepared in such a large scale crystallization facility as shown in FIG. 4 by using the addition section and mixing unit shown in FIG. 9 as the pipeline mixer 118. That is, to the tank 112, 87.6 kg of behenic acid (Edenor C22-85R, trade name, manufactured by Henkel Co.), 423 L of distilled water and 120 L of tert-butanol were added. To the mixture, 49.2 L of 5 mol/L aqueous solution of NaOH was added at 75° C. over 5 minutes with stirring, and allowed to react for 60 minutes to obtain a solution of sodium behenate. On the other hand, 206.2 L of an aqueous solution containing 40.4 kg of silver nitrate (pH 4.0) was prepared and kept at 10° C. in the tank 111. Further, 600 L of pure water was measured in the tank 120, and circulated via the pump 117 through the pipeline mixer 118 (Model PM-20 produced by Mizuho Kogyo Co., Ltd., FIG. 9) from a reaction field solution addition inlet C' (inner diameter: 150 mm) shown in FIG. 9 at a flow rate of 100 L/minute. While stirring was performed by operating the pipeline mixer at 2,400 rpm, the aqueous solution of silver nitrate was added from a silver ion-containing solution addition inlet A' (inner diameter: 10 mm) shown in FIG. 9 at a constant flow rate of 2.9 L/minute, and after 5 seconds, addition of the aqueous solution of sodium behenate was started from an organic acid silver salt solution addition inlet B' (inner diameter: 13.3 mm) shown in FIG. 9 at a constant flow rate of 9.8 L/minute, so that the solutions were stored in the tank 120 via the heat exchanger 119. The distance between the silver ion-containing solution addition inlet A' and the organic acid silver salt solution addition inlet B' was adjusted to 400 mm. Cooling water at 10° C. was supplied to the heat exchanger and a jacket of the tank 120 at a flow rate of 200 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 μS/cm. The solid content obtained as described above was stored as a wet cake without being dried.

Thereafter, dispersion operation was performed in the same manner as that for Organic acid silver salt grain dispersion FF to obtain Organic acid silver salt grain dispersion JJ.

Preparation of Organic Acid Silver Salt Grain Dispersion KK

Organic acid silver salt grain dispersion KK was prepared in such a large scale crystallization facility as shown in FIG. 4 by using the addition section and mixing unit shown in FIG. 9 as the pipeline mixer 118. That is, to the tank 112, 876 kg of behenic acid (Edenor C22-85R, trade name, manufactured by Henkel Co.), 4230 L of distilled water and 1200 L of tert-butanol were added. To the mixture, 49.2 L of 5 mol/L aqueous solution of NaOH was added with stirring at 75° C. over 5 minutes, and allowed to react for 60 minutes to obtain a solution of sodium behenate. On the other hand, 2062 L of an aqueous solution containing 404 kg of silver nitrate (pH 4.0) was prepared and kept at 10° C. in the tank 111. Further, 600 L of pure water was measured in the tank 120, and circulated via the pump 117 through the pipeline mixer 118 (Model LR-1 produced by Mizuho Kogyo Co., Ltd., FIG. 9) from a reaction field solution addition inlet C' (inner diameter: 13.3 mm) shown in FIG. 9 at a flow rate of 1000 mL/minute. While stirring was performed by operating the pipeline mixer at 10,000 rpm (corresponding to a peripheral speed of 13 m/minute) the aqueous solution of silver nitrate was added from a silver ion-containing solution addition inlet A' (inner diameter: 5 mm) shown in FIG. 9 at a constant flow rate of 29 mL/minute, and after 5 seconds, addition of the aqueous solution of sodium behenate was started from an organic acid silver salt solution addition inlet B' (inner diameter: 5 mm) shown in FIG. 9 at a constant flow rate of 98 mL/minute, so that the solutions were stored in the tank 120 via the heat exchanger 119. The distance between the silver ion-containing solution addition inlet A' and the organic acid silver salt solution addition inlet B' was adjusted to 100 mm. Cooling water at 10° C. was supplied to the heat exchanger and a jacket of the tank 120 at a flow rate of 20 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 µS/cm. The solid content obtained as described above was stored as a wet cake without being dried.

Distilled water and polyvinyl alcohol were added to the obtained wet cake according to the composition mentioned below, and centrifuged by using T. K. Homodisper Model 2M-5 (Tokushu Kika Kogyo Co., Ltd.) at 5,000 rpm for 15 minute to obtain a crude dispersion.

Composition of Crude Dispersion:

| | |
|---|---|
| Distilled water | 424 g |
| Organic acid silver salt (wet cake having solid content of 40%) | 560 g |
| Polyvinyl alcohol (PVA-205, Kuraray Co., Ltd.) | 22 g |

The obtained crude dispersion was treated once by using Microfluidizer (M110S-EH, using G10Z interaction chamber produced by Mizuho Kogyo Co., Ltd.) with a pressure of 1600 kg/cm$^2$ to obtain Organic acid silver salt grain dispersion KK. In this operation, the inlet temperature immediately before the dispersion and the outlet temperature immediately after the dispersion were controlled to be 5° C. and 30° C., respectively.

The obtained grains had a mean grain size of 5.36 µm.

Preparation of Organic Acid Silver Salt Grain Dispersion LL

Organic acid silver salt grain dispersion LL was prepared in such a large scale crystallization facility as shown in FIG. 4 by using the addition section and mixing unit shown in FIG. 9 as the pipeline mixer 118. That is, to the tank 112, 87.6 kg of behenic acid (Edenor C22-85R, trade name, manufactured by Henkel Co.), 423 L of distilled water and 120 L of tert-butanol were added. To the mixture, 49.2 L of 5 mol/L aqueous solution of NaOH was added with stirring at 75° C. over 5 minutes, and allowed to react for 60 minutes to obtain a solution of sodium behenate. On the other hand, 206.2 L of an aqueous solution containing 40.4 kg of silver nitrate (pH 4.0) was prepared and kept at 10° C. in the tank 111. Further, 600 L of pure water was measured in the tank 120, and circulated via the pump 117 through the pipeline mixer 118 (Model PM-20 produced by Mizuho Kogyo Co., Ltd., FIG. 9) from a reaction field solution addition inlet C' (inner diameter: 56.5 mm) shown in FIG. 9 at a flow rate of 100 L/minute. While stirring was performed by operating the pipeline mixer at 2,400 rpm, the aqueous solution of silver nitrate was added from a silver ion-containing solution addition inlet A' (inner diameter: 10 mm) shown in FIG. 9 at a constant flow rate of 2.9 L/minute, and after 5 seconds, addition of the aqueous solution of sodium behenate was started from an organic acid silver salt solution addition inlet B' (inner diameter: 13.3 mm) shown in FIG. 9 at a constant flow rate of 9.8 L/minute, so that the solutions were stored in the tank 120 via a heat exchanger 119. The distance between the silver ion-containing solution addition inlet A' and the organic acid silver salt solution addition inlet B' was adjusted to 400 mm. Cooling water at 10° C. was supplied to the heat exchanger and a jacket of the tank 120 at a flow rate of 200 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 µS/cm. The solid content obtained as described above was stored as a wet cake without being dried.

Thereafter, dispersion operation was performed in the same manner as that for Organic acid silver salt grain dispersion FF to obtain Organic acid silver salt grain dispersion LL.

Preparation of Organic Acid Silver Salt Grain Dispersion MM

Figure 10:
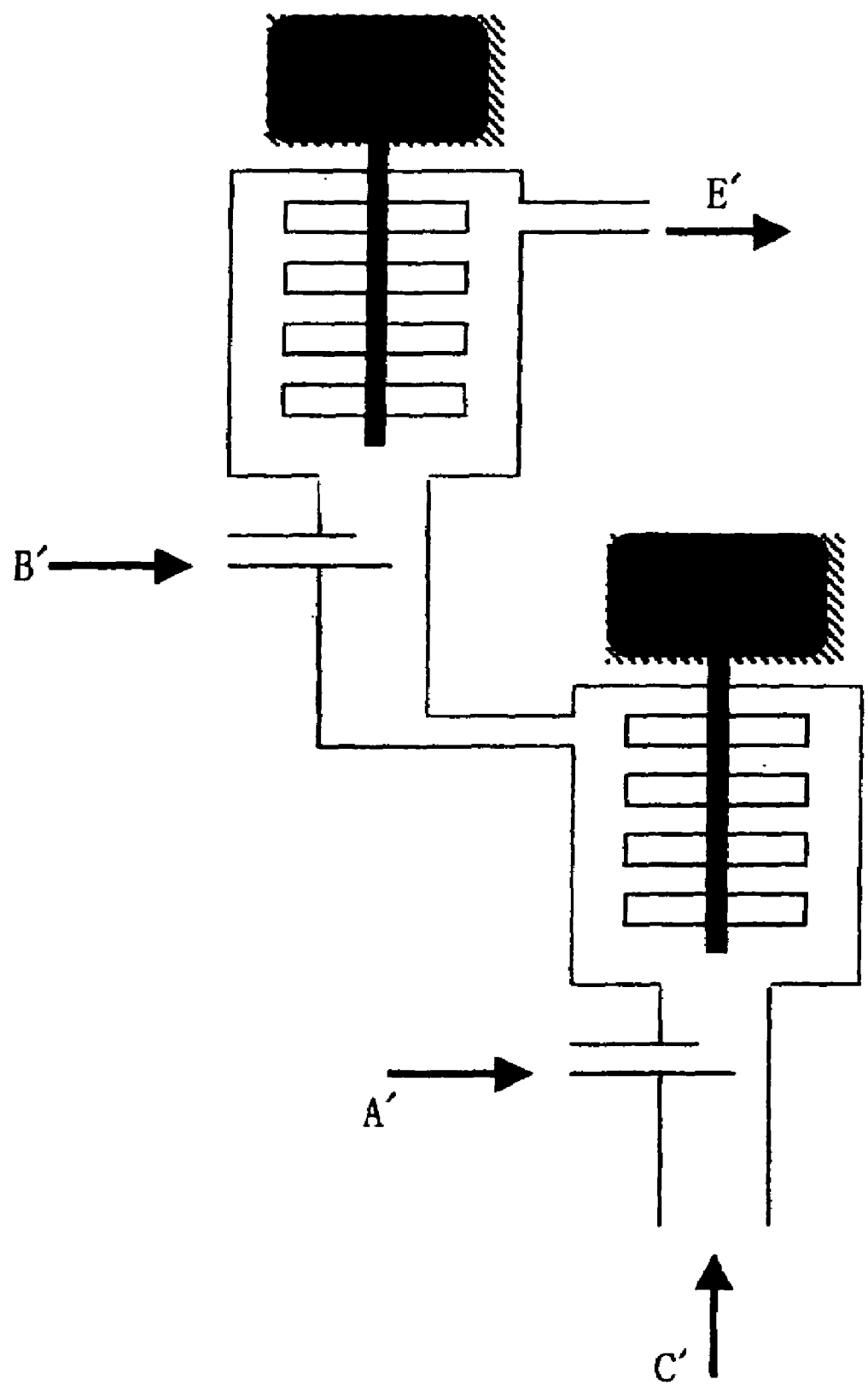
FIG. 10 is a schematic view showing a mixing vessel and its pipelines used in Example 2.

Organic acid silver salt grain dispersion MM was prepared in such a large scale crystallization facility as shown in FIG. 4 by using the addition section and mixing unit shown in FIG. 10 as the pipeline mixer 118. That is, to the tank 112, 87.6 kg of behenic acid (Edenor C22-85R, trade name, manufactured by Henkel Co.), 423 L of distilled water and 120 L of tert-butanol were added. To the mixture, 49.2 L of 5 mol/L aqueous solution of NaOH was added at 75° C. over 5 minutes with stirring, and allowed to react for 60 minutes to obtain a solution of sodium behenate. On the other hand, 206.2 L of an aqueous solution containing 40.4 kg of silver nitrate (pH 4.0) was prepared and kept at 10° C. in the tank 111. Further, 600 L of pure water was measured in the tank 120, and circulated via the pump 117 through the pipeline mixer 118 (Model PM-20 produced by Mizuho Kogyo Co., Ltd., FIG. 10) from a reaction field solution addition inlet C' shown in FIG. 10 at a flow rate of 100 L/minute. While stirring was performed by operating the pipeline mixer at 2,400 rpm, the aqueous solution of silver nitrate was added from a silver ion-containing solution addition inlet A' shown in FIG. 10 at a constant flow rate of 2.9 L/minute, and after 5 seconds, addition of the aqueous solution of sodium behenate was started from an organic acid silver salt solution addition inlet B' shown in FIG. 10 at a constant flow rate of 9.8 L/minute, so that the solutions were stored in the tank 120 via a heat exchanger 119. Cooling water at 10° C. was supplied to the heat exchanger and a jacket of the tank 120 at a flow rate of 200 L/minute, and as a result, the average temperature in the tank was measured to be 30° C. The mixture was left with stirring for 20 minutes as it was to lower the temperature to 25° C. Then, the solid content was separated by suction filtration and washed with water until electric conductivity of the filtrate became 30 µS/cm. The solid content obtained as described above was stored as a wet cake without being dried.

Thereafter, dispersion operation was performed in the same manner as that for Organic acid silver salt grain dispersion FF to obtain Organic acid silver salt grain dispersion MM.

Measurement

Physical properties including grain size, viscosity and so forth of Organic acid silver salt grain dispersions AA to MM obtained as described above and increase of filtration pressure during their preparation are shown in Table 2. In this example, grain size was measured by using a laser diffraction type particle size measurement apparatus (SALD-200J, Shimadzu Corp.). The viscosity was measured at 25° C. by using RFS fluid spectrometer produced by Rheometric Far East Co., Ltd. Further, increase of filtration pressure was measured as a difference of final pressure and initial pressure in filtration of 2 kg of each dispersion using Epocel Filter EC having a diameter of 1.5 cm (produced by Pall Corp.) at a flow rate of 50 ml/minute.

Evaluation of Photographic Performance

Thermally processed image recording materials were produced by using Organic acid silver salt grain dispersions AA to MM as described in Example 4 mentioned later and evaluated by the following method.

Each thermally processed image recording materials was light-exposed and heat-developed (at about 120° C.) by using Fuji Medical Dry Laser Imager FM-DP L (equipped with a semiconductor laser of 660 nm and maximum output of 60 mW (IIIB)), and the obtained image was evaluated by a densitometer. Sensitivity was evaluated as a reciprocal of exposure that gave a density higher than Dmin by 1.0, and represented with a relative value based on the value of the thermally processed image recording material using Organic acid silver salt grain dispersions AA, which was taken as 100. Higher sensitivity means higher image reproducing ability of the thermally processed image recording materials.

Evaluation of Storability After Forced Time Lapse

Thermally processed image recording materials were produced by using Organic acid silver salt grain dispersions AA to MM as described in Example 4 mentioned later and evaluated by the following method.

Each thermally processed image recording material was cut into a piece of 30.5 cm×25.4 cm, of which corners were cut into round corners having a radius of 0.5 cm, and left under conditions of 25° C. and relative humidity of 50% for 1 days. Then, 10 sheets of each thermally processed image recording material were sealed into a bag made of a moisture-proof material, and the bag was left for 5 days in an oven at 50° C. (high temperature storage) or a refrigerator at 4° C. (low temperature storage). Light exposure and heat development were performed in the same manner as in the above evaluation of photographic performance, and density and Dmin of unexposed area were used as values representing fog.

Fog increase ratio=[{(Fog of sample subjected to high temperature storage)−(Fog of sample subjected to low temperature storage)}/{(Maximum concentration of sample subjected to low temperature storage)−(Fog of sample subjected to low temperature storage)}]×100

A lower fog increase ratio indicates better storability after time lapse. When two of addition and mixing lines are used in the same scale, a dispersion of equivalent grain size and photographic performance compared with Dispersion CC can be prepared by using a flow rate of ½ order for each line and a smaller mixing vessel and controlling rotation number as shown in Dispersion AA.

TABLE 2

| Organic acid silver salt grain Dispersion | Grain size | | Viscosity (mPA · s) | Increase of filtration pressure (kg/cm$^2$) | Photographic performance | | Fog increase ratio |
|---|---|---|---|---|---|---|---|
| | Average (µm) | Variation coefficient (%) | | | Dmin | Sensitivity | |
| AA (Invention) | 0.38 | 16 | 19 | 0.18 | 100 | 105 | 1.1 |
| BB (Invention) | 0.38 | 17 | 19 | 0.18 | 100 | 105 | 1.1 |
| CC (Invention) | 0.39 | 16 | 19 | 0.18 | 100 | 105 | 1.1 |
| DD (Invention) | 0.43 | 18 | 18 | 0.21 | 102 | 101 | 1.4 |
| EE (Invention) | 0.37 | 16 | 21 | 0.19 | 101 | 106 | 1.2 |
| FF (Comparative) | 0.62 | 28 | 18 | 0.23 | 100 | 100 | 1.5 |
| GG (Comparative) | 0.55 | 24 | 19 | 0.22 | 100 | 103 | 1.3 |
| GG (Invention) | 0.41 | 16 | 18 | 0.18 | 101 | 105 | 1.1 |
| II (Comparative) | 0.89 | 31 | 22 | 0.27 | 100 | 101 | 1.4 |
| JJ (Invention) | 0.39 | 16 | 19 | 0.18 | 101 | 105 | 1.1 |
| KK (Comparative) | 0.59 | 26 | 19 | 0.22 | 100 | 101 | 1.3 |
| LL (Invention) | 0.37 | 16 | 20 | 0.18 | 100 | 105 | 1.1 |
| MM (Invention) | 0.32 | 16 | 23 | 0.10 | 100 | 105 | 1.0 |

As a comparative experiment, it was attempted to prepare a dispersion in such a large scale crystallization facility as shown in FIG. 4 by using the addition section and mixing unit shown in FIG. 9 as the pipeline mixer 118. In this experiment, when it was attempted to add a silver nitrate aqueous solution at a constant flow rate of 2.9 L/minute from the silver ion-containing solution addition inlet A' having an inner diameter of 5 mm, pressure inside the pipeline exceeded the capacity of the pump, and hence addition at the desired flow rate could not be realized. The Reynolds number at this time was about 22,000. Therefore, improvement of the facility itself, for example, increase of pressure limit of pump used for feeding liquids, is required in order to obtain a Reynolds number exceeding 20,000. However, it is not practical.

EXAMPLE 3

Preparation of Organic Acid Silver Salt Grain Dispersion AAA

In an amount of 876 g of behenic acid (Edenor C22-85R, trade name, manufactured by Henkel Co.), 4230 mL of distilled water and 1200 mL of tert-butanol were added with 492 mL of 5 mol/L aqueous solution of NaOH at 75° C. over 5 minutes with stirring, and allowed to react for 60 minutes to obtain a solution of sodium behenate. Separately, 2062 mL of an aqueous solution containing 404 g of silver nitrate (pH 4.0) was prepared and kept at 10° C. Further, a reaction vessel containing 6350 mL of distilled water and 300 mL of tert-butanol was maintained at 30° C., and added with the whole volume of the aqueous silver nitrate solution at a constant flow rate with stirring. After 7 minutes, the whole volume of the sodium behenate solution was added. The addition times of the aqueous silver nitrate solution and the sodium behenate solution in this operation were 60 minutes and 62 minute, respectively. Therefore, during the last 9 minutes, only the aqueous sodium behenate solution was added. After completion of the addition, 216 ml of 20 weight % aqueous solution of sodium diisobutylnaphthalene-sulfonate was added. The mixture was left as it was with stirring for 20 minutes to lower the temperature to 25° C. The obtained aqueous dispersion of organic acid silver salt showed pH of 6.3.

Figure 11:
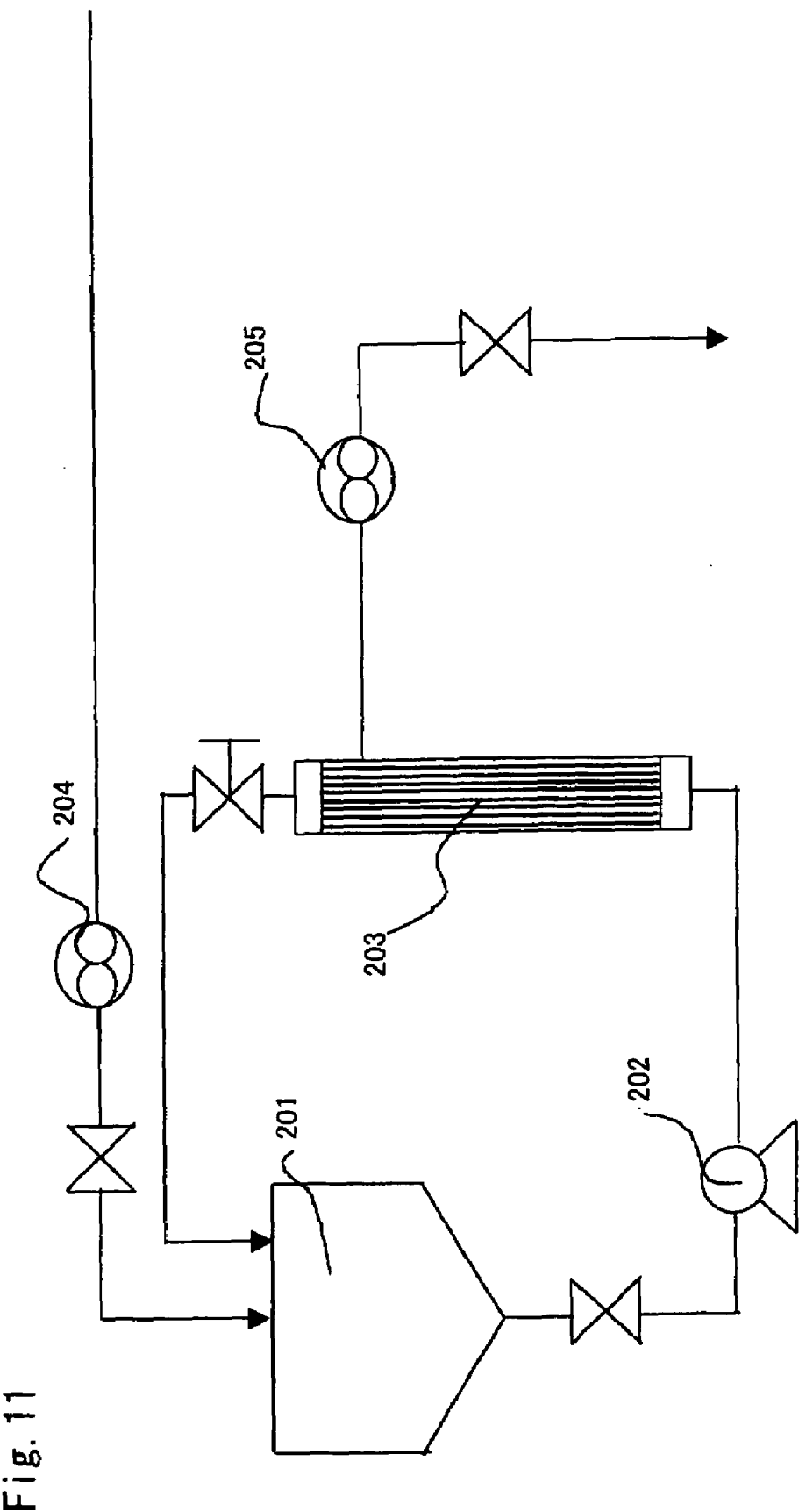
FIG. 11 is a schematic view showing the apparatus used in Example 3.

The obtained aqueous dispersion of organic acid silver salt was transferred to the ultrafiltration unit shown in FIG. 11 to subject it to desalting treatment. The ultrafiltration module used was ACP-1050 produced by Asahi Chemical Industry Co., Ltd. (hollow-fiber membrane). As the filtration scheme, cross flow method was used. The feeding flow rate was 12 L/minute, average filtration pressure was 1.5 kgf/cm$^2$, and operation temperature was 20° C. While the organic acid silver salt concentration was about 5.4 weight % at the start of the desalting treatment, it increased to 10 weight % as the treatment advanced. When the concentration reached 10 weight %, addition of water for constant volume dilution was started. As a solution for constant volume dilution, an aqueous solution of sodium diisobutyl-naphthalenesulfonate (concentration: 0.3 weight %) was used in such a manner that the concentration of dispersing agent should be constant. During the desalting treatment, pH was continuously monitored and maintained at the predetermined level. When the electric conductivity became less than 300 μS/cm, the pH adjustment and supplementation of water were stopped, and concentration operation was started. The concentration operation was performed until the solid content concentration reached 25 weight %. The filtration rate at the endpoint of the concentration was measured. Further, viscosity of Organic acid silver salt dispersion AAA obtained after the concentration was measured by using a B-type viscometer. The solid content was measured by using a digital specific gravimeter, Model DA-300, produced by Kyoto Electronics Manufacturing Co., Ltd., and finally determined based on absolute dry weight.

Preparation of Organic Acid Silver Salt Grain Dispersion BBB

Addition of solutions of sodium behenate and silver nitrate was performed in the same manner as that for Organic acid silver salt aqueous dispersion AAA.

The obtained aqueous dispersion of organic acid silver salt was treated in a dispersing machine (Microfluidizer M-110S-EH; trade name, manufactured by Microfluidex International Corporation, using G10Z interaction chamber) at a pressure controlled to be 600 kg/cm$^2$.

Then, the dispersion was transferred to the ultrafiltration unit shown in FIG. 11, and subjected to desalting and concentration treatments in the same manner as that for Organic acid silver salt aqueous dispersion AAA to obtain Organic acid silver salt aqueous dispersion BBB.

Preparation of Organic Acid Silver Salt Grain Dispersion CCC

Addition of solutions of sodium behenate and silver nitrate was performed in the same manner as that for Organic acid silver salt aqueous dispersion AAA.

Figure 12:
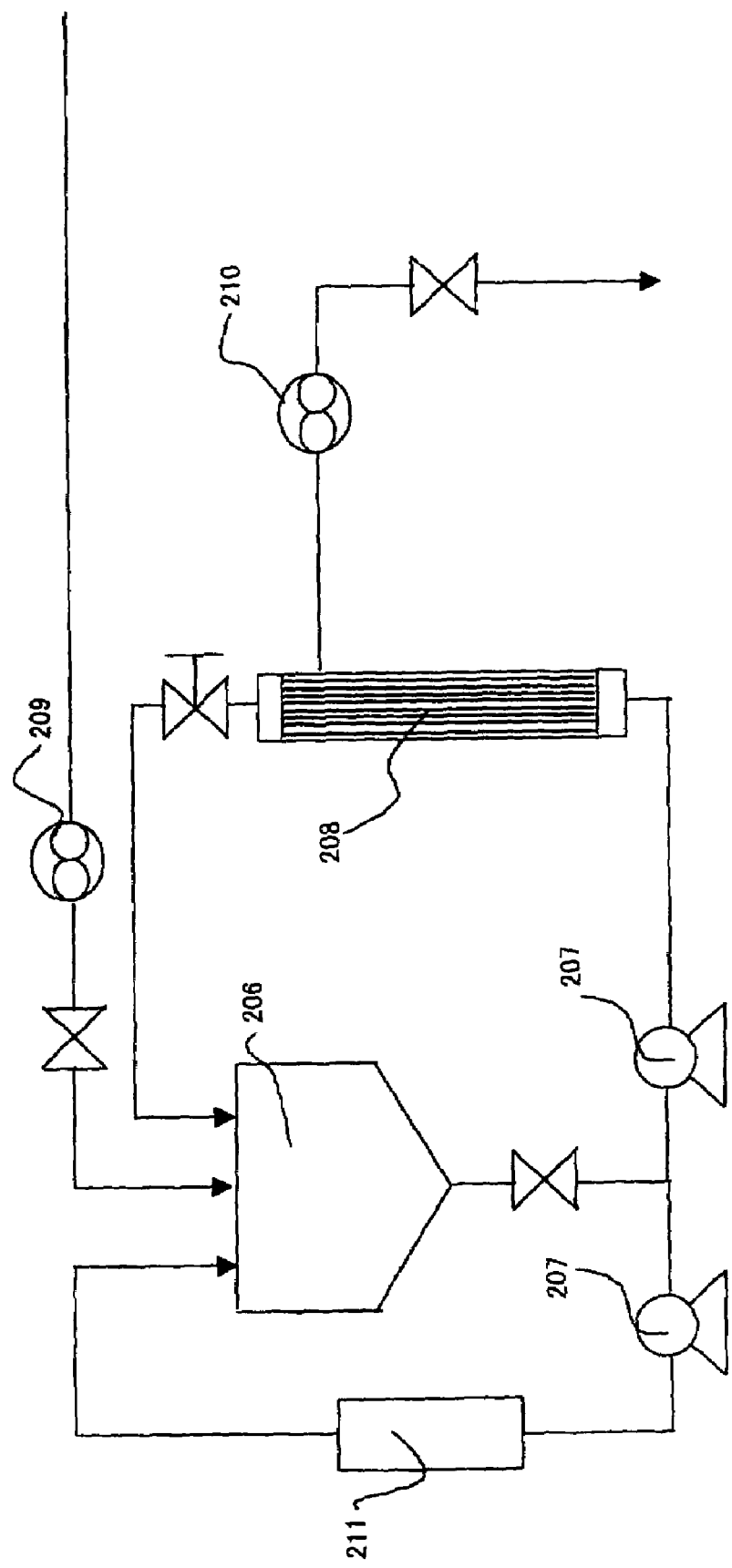
FIG. 12 is a schematic view showing the apparatus used in Example 3.

The obtained aqueous dispersion of organic acid silver salt was simultaneously subjected to dispersion and desalting by ultrafiltration in the apparatus shown in FIG. 12. The dispersing machine used was a rotary type dispersing machine (Milder MDN 303V produced by Ebara Corp.), and the treatment was performed at a rotation number of 15,000 rpm with cooling of the outside with cooling water at 10° C. The feeding flow rate was 4 L/minute.

By using exactly the same ultrafiltration module, filtration conditions and conditions for the subsequent concentration as those for Organic acid silver salt aqueous dispersion AAA, Organic acid silver salt aqueous dispersion CCC was obtained.

The preparation conditions of Organic acid silver salt aqueous dispersions AAA to CCC and so forth are summarized in Table 3. As seen from the results shown in Table 3 below, it was confirmed that the viscosity at the endpoint of the concentration could be suppressed to a low level and the filtration rate could be maintained at a high level by performing

TABLE 3

| Organic acid silver salt dispersion | Dispersing machine | Status at endpoint of concentration | | Status of organic acid silver salt | |
|---|---|---|---|---|---|
| | | Viscosity (PA · s) | Filtration rate (L/m$^2$h) | Grain morphology | Average grain size (μm) |
| AAA (Comparative) | — | 0.113 | 5 | Scaly | 0.68 |
| BBB (Invention) | High pressure homogenizer | 0.012 | 20 | Scaly | 0.61 |
| CCC (Invention) | Rotary type dispersing machine | 0.011 | 22 | Scaly | 0.62 |

EXAMPLE 4

Structures of the compounds used for the production of thermally processed image recording material in this example are shown below.

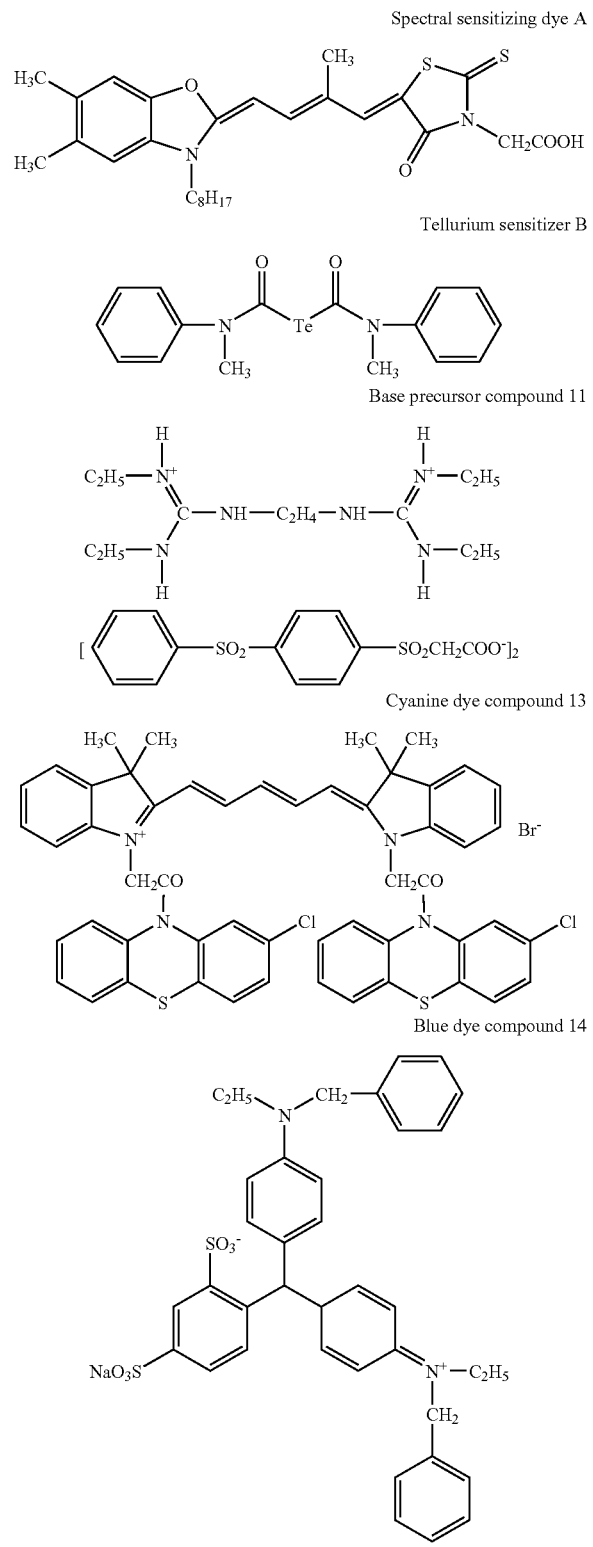

Spectral sensitizing dye A

Tellurium sensitizer B

Base precursor compound 11

Cyanine dye compound 13

Blue dye compound 14

Preparation of Undercoated PET Support (Preparation of PET Support)

Using terephthalic acid and ethylene glycol, polyethylene terephthalate having an intrinsic viscosity of 0.66 (measured in phenol/tetrachloroethane=6/4 (weight ratio) at 25° C.) was obtained in a conventional manner. This was pelletized, and the pellets were dried at 130° C. for 4 hours, melted at 300° C., extruded from a T-die, and quenched to prepare an unstretched film having such a thickness that the film thickness after thermal fixation should become 175 μm.

The film was stretched along the longitudinal direction by 3.3 times at 110° C. using rollers having different peripheral speeds and then stretched along the transverse direction at 130° C. by 4.5 times using a tenter. Thereafter, the film was subjected to thermal fixation at 240° C. for 20 seconds and relaxed by 4% along the transverse direction at the same temperature. Then, after chucks of the tenter were released, the both edges of the film were knurled, and the film was rolled up at 4 kg/cm$^2$ to provide a roll of the film having a thickness of 175 μm.

(Surface Corona Discharging Treatment)

Using a solid state corona discharging treatment machine Model 6KVA manufactured by Piller Inc., both surfaces of the support were treated at room temperature at 20 m/minute. In this case, from the read out values of the electric current and voltage, it was seen that the treatment of 0.375 kV·A·minute/m$^2$ was applied to the support. The treated frequency in this case was 9.6 kHz and the gap clearance between the electrode and the dielectric roll was 1.6 mm.

(Preparation of Undercoated Support)

(1) Preparation of Coating Solutions for Undercoat Layers

Formulation 1 (For Undercoat Layer on Photo Sensitive Layer Side)

| | |
|---|---|
| Pesresin A-515GB made by Takamatsu Yushi K.K. (30 weight % solution) | 234 g |
| Polyethylene glycol monononylphenyl ether (mean ethylene oxide number = 8.5, 10 weight % solution) | 21.5 g |
| MP-1000 made by Soken Kagaku K.K. (polymer microparticles, mean particle size: 0.4 μm) | 0.91 g |
| Distilled water | 744 ml |

Formulation 2 (For First Layer on Back Surface)

| | |
|---|---|
| Styrene-butadiene copolymer latex (solid content: 40 weight %, weight ratio of styrene/butadiene = 68/32) | 158 g |
| 2,4-Dichloro-6-hydroxy-S-triazine sodium salt (8 weight % aqueous solution) | 20 g |
| 1 weight % Aqueous solution of sodium laurylbenzenesulfonate | 10 ml |
| Distilled water | 854 ml |

Formulation 3 (For Second Layer on Back Surface Side)

| | |
|---|---|
| SnO$_2$/SbO (weight ratio: 9/1, mean particle size: 0.038 μm, 17 weight % dispersion) | 84 g |
| Gelatin (10% aqueous solution) | 89.2 g |
| Metorose TC-5 made by Shin-Etsu Chemical Co., Ltd. (2% aqueous solution) | 8.6 g |
| MP-1000 (polymer microparticles) made by Soken Kagaku K.K. | 0.01 g |
| 1 weight % Aqueous solution of sodium dodecylbenzenesulfonate | 10 ml |
| NaOH (1%) | 6 ml |
| Proxel (made by ICI Co.) | 1 ml |
| Distilled water | 805 ml |

(Preparation of Undercoated Support)

After applying the aforementioned corona discharging treatment to both surfaces of the aforementioned biaxially stretched polyethylene terephthalate support having a thickness of 175 μm, one surface (photosensitive layer side) thereof was coated with the undercoating solution of Formulation 1 by a wire bar in a wet coating amount of 6.6 ml/m$^2$ (per one surface) and dried at 180° C. for 5 minutes. Then, the back surface thereof was coated with the undercoating solution of Formulation 2 by a wire bar in a wet coating amount of 5.7 ml/m$^2$ and dried at 180° C. for 5 minutes. The back surface thus coated was further coated with the undercoating solution of Formulation 3 by a wire bar in a wet coating amount of 7.7 ml/m$^2$ and dried at 180° C. for 6 minutes to prepare an undercoated support.

Preparation of Coating Solution for Back Surface (Preparation of Solid Microparticle Dispersion (a) of Base Precursor)

In an amount of 64 g of Base precursor compound 11, 28 g of diphenylsulfone and 10 g of a surface active agent, Demor N (manufactured by Kao Corporation), were mixed with 220 ml of distilled water, and the mixture was beads-dispersed using a sand mill (¼ Gallon Sand Grinder Mill, manufactured by Imex Co.) to obtain Solid microparticle dispersion (a) of the base precursor compound having a mean particle size of 0.2 μm.

(Preparation of Dye Solid Microparticle Dispersion)

In an amount of 9.6 g of Cyanine dye compound 13 and 5.8 g of sodium p-dodecylbenzenesulfonate were mixed with 305 ml of distilled water and the mixture was beads-dispersed using a sand mill (¼ Gallon Sand Grinder Mill, manufactured by Imex Co.) to obtain a dye solid microparticle dispersion having a mean particle size of 0.2 μm.

(Preparation of Coating Solution for Antihalation Layer)

In an amount of 17 g of gelatin, 9.6 g of polyacrylamide, 70 g of the aforementioned Solid microparticle dispersion (a) of the base precursor, 56 g of the aforementioned dye solid microparticle dispersion, 1.5 g of monodispersed polymethyl methacrylate microparticles (mean particle size: 8 μm, standard deviation of particle size: 0.4), 0.03 g of benzoisothiazolinone, 2.2 g of sodium polyethylenesulfonate, 0.2 g of Blue dye compound 14 and 844 ml of water were mixed to prepare a coating solution for antihalation layer.

(Preparation of Coating Solution for Back Surface Protective Layer)

In a container kept at 40° C., 50 g of gelatin, 0.2 g of sodium polystyrenesulfonate, 2.4 g of N,N-ethylenebis(vinylsulfonacetamide), 1 g of sodium t-octylphenoxyethoxyethanesulfonate, 30 mg of benzoisothiazolinone, 37 mg of N-perfluorooctylsulfonyl-N-propylalanine potassium salt, 0.15 g of polyethylene glycol mono(N-perfluorooctylsulfonyl-N-propyl-2-aminoethyl) ether [average polymerization degree of ethylene oxide: 15], 32 mg of $C_8F_{17}SO_3K$, 64 mg of $C_8F_{17}SO_2N(C_3H_7)$ $(CH_2CH_2O)_4(CH_2)_4$—$SO_3Na$, 8.8 g of an acrylic acid/ethyl acrylate copolymer (copolymerization ratio (weight ratio): 5/95), 0.6 g of Aerosol OT (manufactured by American Cyanamid Company), 1.8 g (as liquid paraffin) of a liquid paraffin emulsion and 950 ml of water were mixed to form a coating solution for back surface protective layer.

Preparation of Silver Halide Emulsion 1

In an amount of 1421 ml of distilled water was added with 3.1 ml of 1 weight % potassium bromide solution, and further added with 3.5 ml of 0.5 mol/L sulfuric acid and 31.7 g of phthalized gelatin. Separately, Solution A was prepared by adding distilled water to 22.22 g of silver nitrate to dilute it to 95.4 ml, and Solution B was prepared by diluting 15.9 g of potassium bromide with distilled water to a volume of 97.4 ml. To the aforementioned mixture maintained at 34° C. and stirred in a titanium-coated stainless steel reaction vessel, the whole volume of Solution A and Solution B was added over 45 seconds at constant flow rates. Then, the mixture was added with 10 ml of 3.5 weight % aqueous hydrogen peroxide solution, and further added with 10.8 ml of a 10 weight % aqueous solution of benzimidazole. Further, Solution C was prepared by adding distilled water to 51.86 g of silver nitrate to dilute it to 317.5 ml, and Solution D was prepared by diluting 45.8 g of potassium bromide with distilled water to a volume of 400 ml. The whole volume of Solution C was added to the mixture over 20 minutes at a constant flow rate. Solution D was added by the control double jet method while pAg was maintained at 8.1. Hexachloroiridic acid (III) potassium salt in an amount of $1 \times 10^{-4}$ mole per mole of silver was added at one time 10 minutes after the addition of Solutions C and D was started. Further, an aqueous solution of potassium iron (II) hexacyanide in an amount of $3 \times 10^{-4}$ mole per mole of silver was added at one time 5 seconds after the addition of Solution C was completed. Then, the mixture was adjusted to pH 3.8 using 0.5 mol/L sulfuric acid, and the stirring was stopped. Then, the mixture was subjected to precipitation, desalting and washing with water, adjusted to pH 5.9 with 1 mol/L sodium hydroxide to form a silver halide dispersion having pAg of 8.0.

The aforementioned silver halide dispersion was added with 5 ml of a 0.34 weight % methanol solution of 1,2-benzisothiazolin-3-one with stirring at 38° C., and after 40 minutes since then, added with a methanol solution of Spectral sensitizing dye A in an amount of $1 \times 10^{-3}$ mole per mole of silver. After 1 minutes, the mixture was warmed to 47° C., and 20 minutes after the warming, added with $7.6 \times 10^{-5}$ mole of sodium benzenethiosulfonate per mole of silver as a methanol solution. Further after 5 minutes, the mixture was added with Tellurium sensitizer B as a methanol solution in an amount of $1.9 \times 10^{-4}$ mole per mole of silver followed by ripening for 91 minutes. The mixture was added with 1.3 ml of a 0.8 weight % methanol solution of N,N'-dihydroxy-N"-diethylmelamine, and 4 minutes later, added with $3.7 \times 10^{-3}$ mole per mole of silver of 5-methyl-2-mercaptobenzimidazole and $4.9 \times 10^{-3}$ mole per mole of silver of 1-phenyl-2-heptyl-5-mercapto-1,3,4-triazole as a methanol solution to prepare Silver halide emulsion 1.

The grains in the prepared silver halide emulsion were pure silver bromide grains having a mean diameter as spheres of 0.046 μm and a variation coefficient of 20% for mean diameter as spheres. The grain size and others were obtained from averages for 1000 grains by using an electron microscope. The [100] face ratio of these grains was determined to be 80% by the Kubelka-Munk method.

Preparation of Silver Halide Emulsion 2

Silver halide emulsion 2 was prepared in the same manner as the preparation of Silver halide emulsion 1 except that the liquid temperature upon grain formation was changed from 34° C. to 49° C., addition time of Solution C was changed to 30 minutes and potassium iron (II) hexacyanide was not used. Then, as in the case of Silver halide emulsion 1, the steps of precipitation, desalting, washing with water and dispersion were performed. Furthermore, in the same manner as in the case of Silver halide emulsion 1 except that the addition amount of Spectral sensitizing dye A was changed to $7.5 \times 10^{-4}$ mole per mole of silver, the addition amount of Tellurium sensitiser B was changed to $1.1 \times 10^{-4}$ mole per mole of silver, and the addition amount of 1-phenyl-2-heptyl-5-mercapto-1,3,4-triazole was changed to $3.3 \times 10^{-3}$ mole of per mole of silver, spectral sensitization, chemical sensitization, and addition of 5-methyl-2-mercaptobenzimidazole and 1-phenyl-2-heptyl-5-mercapto-1,3,4-traizole were performed to obtain Silver halide emulsion 2. Emulsion grains of Silver halide emulsion 2 were pure silver bromide cubic grains having a mean grain diameter of 0.080 μm as spheres and a variation coefficient of 20% for diameter as spheres.

Preparation of Silver Halide Emulsion 3

Silver halide emulsion 3 was prepared in the same manner as the preparation of Silver halide emulsion 1 except that the liquid temperature upon grain formation was changed from 34° C. to 27° C. Further, as in the case of Silver halide emulsion 1, the steps of precipitation, desalting, washing with water and dispersion were performed. Then, Silver halide emulsion 3 was obtained in the same manner as in the case of Silver halide emulsion 1 except that the addition amount of Spectral sensitizing dye A solid dispersion (gelatin aqueous solution) was changed to $6 \times 10^{-3}$ mole per mole of silver and the addition amount of Tellurium sensitizer B was changed to $5.2 \times 10^{-4}$ mole per mole of silver. Emulsion grains of Silver halide emulsion 3 were pure silver bromide cubic grains having a mean grain diameter of 0.038 μm as spheres and a variation coefficient of 20% for diameter as spheres.

Preparation of Mixed Emulsion A for Coating Solution

In an amount of 70% by weight of Silver halide emulsion 1, 15% by weight of Silver halide emulsion 2 and 15% by weight of Silver halide emulsion 3 were mixed and added with benzothiazolium iodide in an amount of $7 \times 10^{31\ 3}$ mole per mole of silver as a 1 weight % aqueous solution to form Mixed emulsion A for coating solution.

Preparation of 25 Weight % Dispersion of Reducing Agent Complex

In an amount of 10 kg of 1:1 complex of 2,2-methylenebis-(4-ethyl-6-tert-butylphenol) and triphenyl-phosphine oxide, and 10 kg of a 20 weight % aqueous solution of denatured polyvinyl alcohol (Poval MP203, manufactured by Kuraray Co., Ltd.) were added with 16 kg of water, and mixed sufficiently to form slurry. The slurry was fed by a diaphragm pump to a sand mill of horizontal type (UVM-2, manufactured by Imex Co.) containing zirconia beads having a mean diameter of 0.5 mm, and dispersed for 3 hours and 30 minutes. Then, the slurry was added with 0.2 g of benzothiazolinone sodium salt and water so that the concentration of the reducing agent should become 25 weight % to obtain a solid microparticule dispersion of reducing agent complex. The reducing agent complex particles contained in the dispersion of reducing agent complex obtained as described above had a median diameter of 0.46 μm and the maximum particle size of 2.0 μm or less. The obtained reducing agent complex dispersion was filtered through a polypropylene filter having a pore size of 10.0 μm to remove dusts and so forth, and stored.

Preparation of 10 Weight % Dispersion of Mercapto Compound

In an amount of 5 kg of 1-phenyl-2-heptyl-5-mercapto-1,3,4-triazole and 5 kg of a 20 weight % aqueous solution of denatured polyvinyl alcohol (Poval MP203, manufactured by Kuraray Co., Ltd.) were added with 8.3 kg of water, and mixed sufficiently to form slurry. The slurry was fed by a diaphragm pump to a sand mill of horizontal type (UVM-2, manufactured by Imex Co.) containing zirconia beads having a mean diameter of 0.5 mm, and dispersed for 6 hours. Then, the slurry was added with water so that the concentration of the mercapto compound should become 10 weight % to obtain a mercapto compound dispersion. The mercapto compound particles contained in the mercapto compound dispersion obtained as described above had a median diameter of 0.40 μm and the maximum particle size of 2.0 μm or less. The obtained mercapto compound dispersion was filtered through a polypropylene filter having a pore size of 10.0 μm to remove dusts and so forth, and stored. The dispersion was filtered again through a polypropylene filter having a pore size of 10.0 μm immediately before use.

Preparation of 26 Weight % Dispersion of Organic Polyhalogenated Compound 1

In an amount of 5 kg of tribromomethylphenylsulfone, 5 kg of a 20 weight % aqueous solution of denatured polyvinyl alcohol (Poval MP203, manufactured by Kuraray Co., Ltd.) and 213 g of 20 weight % aqueous solution of sodium triisopropylnaphthalene-sulfonate were added with 10 kg of water, and mixed sufficiently to form slurry. The slurry was fed by a diaphragm pump to a sand mill of horizontal type (UVM-2, manufactured by Imex Co.) containing zirconia beads having a mean diameter of 0.5 mm, and dispersed for 5 hours. Then, the slurry was added with 0.2 g of benzisothiazolinone sodium salt and water so that the concentration of the organic polyhalogenated compound should become 26 weight % to obtain an organic polyhalogenated compound dispersion. The organic polyhalogenated compound particles contained in the polyhalogenated compound dispersion obtained as described above had a median diameter of 0.41 μm and the maximum particle size of 2.0 μm or less. The obtained organic polyhalogenated compound dispersion was filtered through a polypropylene filter having a pore size of 3.0 μm to remove dusts and so forth, and stored. Then, the dispersion was stored at 10° C. or lower until use.

Preparation of 25 Weight % Dispersion of Organic Polyhalogenated Compound 2

In an amount of 5 kg of tribromomethyl-3-pentanoylaminophenylsulfone, 2.5 kg of 20 weight % aqueous solution of denatured polyvinyl alcohol (Poval MP203, manufactured by Kuraray Co., Ltd.), 213 g of 20 weight % aqueous solution of sodium triisopropylnaphthalenesulfonate and 10 kg of water were mixed sufficiently to form slurry. The slurry was fed by a diaphragm pump to a sand mill of horizontal type (UVM-2, manufactured by Imex Co.) containing zirconia beads having a mean particle size of 0.5 mm, and dispersed for 5 hours. Then, the slurry was added with 0.2 g of benzisothiazolinone sodium salt and water so that the concentration of the organic polyhalogenated compound should become 25 weight % to obtain organic polyhalogenated compound dispersion. The organic polyhalogenated compound particles contained in the organic polyhalogenated compound dispersion obtained as described above had a median particle size of 0.41 μm and the maximum particle size of 2.0 μm or less. The obtained organic polyhalogenated compound dispersion was filtered through a polypropylene filter having a pore size of 3.0 μm to remove dusts and so forth, and stored.

Preparation of 5 Weight % Solution of Phthalazine Compound

In an amount of 8 kg of denatured polyvinyl alcohol (MP-203, manufactured by Kuraray Co., Ltd.) was dissolved in 174.57 kg of water and then added with 3.15 kg of 20 weight % aqueous solution of sodium triisopropylnaphthalenesulfonate and 14.28 kg of 70 weight % aqueous solution of 6-isopropylphthalazine to obtain a 5 weight % solution of 6-isopropylphthalazine.

Preparation of 20 Weight % Dispersion of Pigment

In an amount of 64 g of C.I. Pigment Blue 60 and 6.4 g of Demor N manufactured by Kao Corporation, and 250 g of water were mixed sufficiently to provide slurry. Then, 800 g of zirconia beads having a mean particle size of 0.5 mm were placed in a vessel together with the slurry and the slurry was dispersed by a dispersing machine (¼G Sand Grinder Mill; manufactured by Imex Co.) for 25 hours to obtain a pigment dispersion. The pigment particles contained in the dispersion obtained as described above had a mean particle size of 0.21 μm.

Preparation of 40 Weight % SBR Latex

SBR latex purified by ultrafiltration (UF) was obtained as follows.
The SBR latex mentioned below diluted by 10 times with distilled water was diluted and purified by using an UF-purification module FS03-FC-FUYO3A1 (manufactured by Daisen Membrane System K.K.) until the ion conductivity became 1.5 mS/cm, and added with Sandet-BL (manufactured by SANYO CHEMICAL INDUSTRIES, LTD.) to a concentration of 0.22 weight %. Further, the latex was added with NaOH and NH$_4$OH so that the ratio of Na$^+$ ion:NH$_4^+$ ion should become 1:2.3 (molar ratio) to adjust pH to 8.4. At this point, the concentration of the latex was 40 weight %.

(SBR latex: a latex of -St(71)-Bu(26)-AA(3)-,
wherein the numerals in the parentheses indicate the contents in terms of weight %, St represents styrene, Bu represents butadiene and AA represents acrylic acid)

The latex had the following characteristics: mean particle size of 0.1 μm, concentration of 45%, equilibrated moisture content of 0.6 weight % at 25° C. and 60% RH, and ion conductivity of 4.2 mS/cm (measured for the latex stock solution (40%) at 25° C. by using a conductometer, CM-30S, manufactured by To a Electronics, Ltd.), pH 8.2.

Preparation of Coating Solution for Image-forming Layer

In an amount of 103 g of organic acid silver salt dispersion, which was one of those prepared in Examples 1–3, 1.1 g of the 20 weight % aqueous dispersion of pigment, 5 g of 20 weight % of aqueous solution of polyvinyl alcohol PVA-205 (Kraray Co., Ltd.), 26 g of the 25 weight % dispersion of the reducing agent complex, 8.2 g in total of the dispersions of Organic polyhalogenated compound 1 and 2 (weight ratio=1:3), 6.2 g of the 10 weight % dispersion of mercapto compound, 106 g of the 40 weight % aqueous solution of SBR latex (Tg: 24° C.) undergone the ultrafiltration (UF) purification and pH adjustment and 18 ml of the 5 weight % solution of phthalazine compound were combined, and mixed sufficiently with 10 g of Silver halide mixed emulsion A immediately before coating to prepare a coating solution for image-forming layer (photosensitive layer, emulsion layer). The coating solution was fed as it was to a coating die in such a feeding amount giving a coating amount of 70 ml/m$^2$ and coated.

The viscosity of the obtained coating solution for image-forming layer was measured by a B-type viscometer manufactured by Tokyo Keiki K.K. and found to be 85 [mPa·s] at 40° C. (Rotor No. 1, 60 rpm).

The viscosity of the coating solution was measured at 25° C. by RFS fluid spectrometer produced by Rheometric Far East Co., Ltd., and found to be 1500, 220, 70, 40 and 20 [mPa·s] at shear rates of 0.1, 1, 10, 100 and 1000 [1/second], respectively.

Preparation of Coating Solution for Intermediate Layer on Image-forming Layer Side In an amount of 772 g of a 10 weight % aqueous solution of polyvinyl alcohol, PVA-205 (manufactured by Kuraray Co., Ltd.), 5.3 g of the 20 weight % dispersion of pigment, 226 g of 27.5 weight % solution of methyl methacrylate/styrene/butyl acrylate/hydroxyethyl methacrylate/acrylic acid copolymer (copolymerization ratio (by weight): 64/9/20/5/2) latex, 2 ml of 5 weight % aqueous solution of Aerosol OT (manufactured by American Cyanamid Company), 10.5 ml of 20 weight % aqueous solution of phthalic acid diammonium salt and water in such an amount giving a total amount of 880 g were mixed and adjusted to pH 7.5 with NaOH to form a coating solution for intermediate layer. This coating solution was fed to a coating die in such an amount that gave a coating amount of 10 ml/m$^2$.

The viscosity of the coating solution measured by a B-type viscometer at 40° C. (Rotor No. 1, 60 rpm) was 21 [mPa·s].

Preparation of Coating Solution for 1st Protective Layer on Image-forming Layer Side In an amount of 64 g of inert gelatin was dissolved in water, added with 80 g of 27.5 weight % latex solution of methyl methacrylate/styrene/butyl acrylate/hydroxyethyl methacrylate/acrylic acid copolymer (copolymerization ratio (by weight): 64/9/20/5/2), 23 ml of 10 weight % methanol solution of phthalic acid, 23 ml of 10 weight % aqueous solution of 4-methylphthalic acid, 28 ml of 0.5 mol/L sulfuric acid, 5 ml of 5 weight % aqueous solution of Aerosol OT (manufactured by American Cyanamid Company), 0.5 g of phenoxyethanol, 0.1 g of benzoisothiazolinone, and water in such an amount that gave a total amount of 750 g to form a coating solution. The coating solution was mixed with 26 ml of 4 weight % chromium alum by a static mixer immediately before coating, and fed to a coating die in such an amount that gave a coating amount of 18.6 ml/m$^2$.

The viscosity of the coating solution measured by a B-type viscometer (Rotor No. 1, 60 rpm) at 40° C. was 17 [mPa·s].

Preparation of Coating Solution for 2nd Protective Layer on Image-forming Layer Side In an amount of 80 g of inert gelatin was dissolved in water, added with 102 g of 27.5 weight % latex solution of methyl methacrylate/styrene/butyl acrylate/hydroxyethyl methacrylate/acrylic acid copolymer (copolymerization ratio (by weight): 64/9/20/5/2), 3.2 ml of 5 weight % solution of N-perfluorooctylsulfonyl-N-propylalaninepotassium salt, 32 ml of 2 weight % aqueous solution of polyethylene glycol mono(N-perfluorooctylsulfonyl-N-propyl-2-aminoethyl) ether [average polymerization degree of ethylene oxide=15], 23 ml of 5 weight % aqueous solution of Aerosol OT (manufactured by American Cyanamid Company), 4 g of polymethyl methacrylate microparticles (mean particle size: 0.7 µm), 21 g of polymethyl methacrylate microparticles (mean particle size: 4.5 µm), 1.6 g of 4-methylphthalic acid, 4.8 g of phthalic acid, 44 ml of 0.5 mol/L sulfuric acid, 10 mg of benzoisothiazolinone and water in such an amount that gave a total amount of 650 g were mixed to form a coating solution. The coating solution was further mixed with 445 ml of an aqueous solution containing 4 weight % of chromium alum and 0.67 weight % of phthalic acid by a static mixer immediately before coating to form a coating solution for protective layer, and fed to a coating die in such an amount that gave a coating amount of 8.3 ml/m$^2$.

The viscosity of the coating solution measured by a B-type viscometer (Rotor No. 1, 60 rpm) at 40° C. was 9 [mPa·s].

Preparation of Thermally Processed Image Forming Material

On the back surface side of the aforementioned support having undercoat layers, the coating solution for antihalation layer and the coating solution for back surface protective layer were simultaneously applied as stacked layers so that the applied solid content of the solid microparticle dye in the antihalation layer should be 0.04 g/m$^2$, and the applied amount of gelatin in the back surface protective layer should be 1.7 g/m$^2$, and dried to form a back layer.

Then, on the side opposite to the back side, an image-forming layer (coated silver amount of the silver halide was 0.14 g/m$^2$), intermediate layer, first protective layer and second protective layer were simultaneously coated in this order from the undercoat layer by the slide bead coating method as stacked layers to form a sample of thermally processed image recording material. The conditions of coating and drying were as follows.

The coating was performed at a speed of 160 m/min. The gap between the tip of coating die and the support was set to be 0.10 to 0.30 mm, and the pressure in the reduced pressure chamber was adjusted to be lower than the atmospheric pressure by 196–882 Pa. Electrostatic charge of the support was eliminated by ionized wind before the coating.

In the subsequent chilling zone, the coating solutions were cooled with air blow showing a dry-bulb temperature of 10–20° C. Then, the material was transported without contact, and dried with drying air showing a dry-bulb temperature of 23–45° C. and a wet-bulb temperature of 15–21° C. in a coil-shaped non-contact type drier.

After the drying, the material was conditioned for its moisture content at 25° C. and relative humidity of 40–60%, and heated so that the temperature of film surface should become 70–90° C. After the heating, the material was cooled to 25° C. as a temperature of film surface.

The prepared thermally processed image recording material showed matting degree of 550 seconds for the photosensitive layer side, and 130 seconds for the back surface, in terms of Beck's smoothness. The film surface pH on the photosensitive layer side was measured to be 6.0.

Evaluation of Thermally Image Recording Material

Coated surface condition of the image-forming layers of the thermally image recording materials produced by using the organic acid silver salt grain dispersions prepared in Examples 1–3 was evaluated by visual inspection. As a result, it was found that the thermally image recording materials produced by using the organic acid silver salt grain dispersions prepared by the preparation methods of the present invention showed extremely good coated surface condition.

What is claimed is:

1. A method for producing a thermally processed image recording material comprising a silver salt of an organic acid, a reducing agent for silver ions and a binder on at least one surface of a support, which comprises:
    (a) providing a dispersion of grains of silver salt of an organic acid which have been prepared by reacting a solution containing silver ions and a solution containing an alkali metal salt of an organic acid in sealed mixing means and which have been prepared by supplying the solution containing silver ions into a reaction field solution before being introduced into the sealed mixing means, and supplying the solution containing an alkali metal salt of an organic acid into the reaction field solution or sealed mixing means to which the solution containing silver ions has been supplied; and
    (b) applying a coating solution containing the dispersion of grains of silver salt of an organic acid prepared by step (a), a reducing agent for silver ions and a binder to form an image-forming layer on at least one surface of a support.

2. The method for producing a thermally processed image recording material according to claim 1, wherein, in step (a), Reynolds number of the solution containing silver ions is in the range of 500–20000 when the solution containing silver ions is supplied to the reaction field solution.

3. The method for producing a thermally processed image recording material according to claim 1, wherein step (b) comprises applying a coating solution containing an aqueous dispersion of the grains of silver salt of an organic acid prepared by step (a) on at least one surface of the support.

4. The method for producing a thermally processed image recording material according to claim 3, wherein the coating solution contains a photosensitive silver halide and a polymer showing an equilibrated moisture content of 2 weight % or less at 25° C. and relative humidity of 60% in the form of latex as the binder, and 30 weight % or more of the solvent of the coating solution consists of water.

5. A method for producing a thermally processed image recording material comprising a silver salt of an organic acid, a reducing agent for silver ions and a binder on at least one surface of a support, which comprises:
   (a) providing a dispersion of grains of silver salt of an organic acid which have been prepared by mixing a solution containing silver ions and a solution containing an alkali metal salt of an organic acid to conduct a reaction in sealed mixing means and removing by-product salts contained in the reaction mixture by filtration through an ultrafiltration membrane during or after the reaction; and
   (b) applying a coating solution containing the dispersion of grains of silver salt of an organic acid prepared by step (a), a reducing agent for silver ions and a binder to form an image-forming layer on at least one surface of a support.

6. The method for producing a thermally processed image recording material according to claim 5, wherein, in step (a), at least a part of a mixture obtained after the reaction of the solution containing silver ions and the solution containing an alkali metal salt of an organic acid mixed in the sealed mixing means is circulated and returned to the sealed mixing means.

7. The method for producing a thermally processed image recording material according to claim 5, wherein, in step (a), at least one kind of dispersing agent is added before starting the reaction or before finishing the purification utilizing an ultrafiltration membrane.

8. The method for producing a thermally processed image recording material according to claim 7, wherein, in step (a), a nonionic macromolecular dispersing agent having a molecular weight 5–50 times larger than a fractional molecular weight of the ultrafiltration membrane is used as the dispersing agent.

9. The method for producing a thermally processed image recording material according to claim 8, wherein, in step (a), the nonionic macromolecular dispersing agent is used at a concentration of 0.1–30 weight % of solid content of the silver salt of an organic acid.

10. The method for producing a thermally processed image recording material according to claim 7, wherein, in step (a), at least one of polyvinyl alcohol, polyvinylpyrrolidone, hydroxyethyl cellulose and hydroxypropyl cellulose is used as the dispersing agent.

11. The method for producing a thermally processed image recording material according to claim 5, wherein, in step (a), the by-product salts are removed by ultrafiltration in which 2- to 20-fold constant volume dilution is attained, and then the dispersion is concentrated to a concentration of 10–50 weight %.

12. The method for producing a thermally processed image recording material according to claim 5, wherein step (b) comprises applying a coating solution containing an aqueous dispersion of the grains of silver salt of an organic acid prepared by step (a) on at least one surface of the support.

13. The method for producing a thermally processed image recording material according to claim 12, wherein the coating solution contains a photosensitive silver halide and a polymer showing an equilibrated moisture content of 2 weight % or less at 25° C. and relative humidity of 60% in the form of latex as the binder, and 30 weight % or more of the solvent of the coating solution consists of water.

14. A method for producing a thermally processed image recording material comprising a silver salt of an organic acid, a reducing agent for silver ions and a binder on at least one surface of a support, which comprises:
   (a) providing an aqueous dispersion of grains of silver salt of an organic acid prepared by reacting a solution containing silver ions and a solution containing an alkali metal salt of an organic acid to obtain silver salt of an organic acid, dispersing the silver salt of an organic acid by a high pressure homogenizer or high speed rotary homomixer in the presence of a dispersing agent, and removing by-product salts by ultrafiltration after or during the dispersing operation; and
   (b) applying a coating solution containing the aqueous dispersion of grains of silver salt of an organic acid prepared in step (a), a reducing agent for silver ions and a binder to form an image-forming layer on at least one surface of a support.

15. The method for producing a thermally processed image recording material according to claim 14, wherein, in step (a), the dispersing agent is used at a concentration of 1–30 weight % of dispersoid.

16. The method for producing a thermally processed image recording material according to claim 14, wherein, in step (a), concentration of the grains of silver salt of an organic acid is 1–10 weight % immediately after the reaction.

17. The method for producing a thermally processed image recording material according to claim 14, wherein, in step (a), after the by-product salts are removed by the ultrafiltration, concentration operation is performed by the ultrafiltration.

18. The method for producing a thermally processed image recording material according to claim 14, wherein, in step (a), after electric conductivity reached within the range of from 20 µS/cm to less than 300 µS/cm as a result of the removal of the by-product salts by the ultrafiltration, the dispersion is concentrated to a concentration of 10–70 weight % by the ultrafiltration.

19. The method for producing a thermally processed image recording material according to claim 14, wherein step (b) comprises applying a coating solution containing an aqueous dispersion of the grains of silver salt of an organic acid prepared by step (a) on at least one surface of the support.

20. The method for producing a thermally processed image recording material according to claim 19, wherein the coating solution contains a photosensitive silver halide and a polymer showing an equilibrated moisture content of 2 weight % or less at 25° C. and relative humidity of 60% in the form of latex as the binder, and 30 weight % or more of the solvent of the coating solution consists of water.

* * * * *